US012559544B2

(12) United States Patent
Mousa et al.

(10) Patent No.: US 12,559,544 B2
(45) Date of Patent: Feb. 24, 2026

(54) ANTIBODIES THAT BIND HUMAN METAPNEUMOVIRUS FUSION PROTEIN AND THEIR USE

(71) Applicant: University of Georgia Research Foundation, Inc., Athens, GA (US)

(72) Inventors: Jarrod Mousa, Athens, GA (US); Ralph A. Tripp, Watkinsville, GA (US); Jiachen Huang, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1048 days.

(21) Appl. No.: 17/612,954

(22) PCT Filed: May 20, 2020

(86) PCT No.: PCT/US2020/033865
§ 371 (c)(1),
(2) Date: Nov. 19, 2021

(87) PCT Pub. No.: WO2020/236974
PCT Pub. Date: Nov. 26, 2020

(65) Prior Publication Data
US 2023/0085439 A1 Mar. 16, 2023

Related U.S. Application Data

(60) Provisional application No. 62/851,020, filed on May 21, 2019.

(51) Int. Cl.
| | |
|---|---|
| *C07K 16/00* | (2006.01) |
| *A61K 39/00* | (2006.01) |
| *A61P 31/14* | (2006.01) |
| *C07K 16/10* | (2006.01) |
| *C12N 5/071* | (2010.01) |
| *C12N 15/62* | (2006.01) |
| *C12N 15/85* | (2006.01) |
| *G01N 33/569* | (2006.01) |

(52) U.S. Cl.
CPC .......... *C07K 16/1027* (2013.01); *A61P 31/14* (2018.01); *C12N 5/0686* (2013.01); *C12N 15/62* (2013.01); *C12N 15/85* (2013.01); *G01N 33/56983* (2013.01); *A61K 39/00* (2013.01); *C07K 2317/21* (2013.01); *C07K 2317/31* (2013.01); *C12N 2510/02* (2013.01); *C12N 2800/107* (2013.01); *G01N 2333/08* (2013.01)

(58) Field of Classification Search
None
See application file for complete search history.

(56) References Cited

U.S. PATENT DOCUMENTS

2015/0322137 A1 11/2015 Takada et al.

FOREIGN PATENT DOCUMENTS

| CN | 104350069 A | 2/2015 |
|---|---|---|
| WO | WO 2008/043052 A2 | 4/2008 |
| WO | WO 2013/140247 A1 | 9/2013 |
| WO | WO 2018/075378 A1 | 4/2018 |
| WO | WO 2018/118754 A1 | 6/2018 |
| WO | WO 2018/140242 A1 | 8/2018 |

OTHER PUBLICATIONS

Shafagati N, Williams J. Human metapneumovirus—what we know now. F1000Res. Feb. 1, 2018;7:135. doi: 10.12688/f1000research. 12625.1. (Year: 2018).*

Bar-Peled et al., "A potent neutralizing site III-specific human antibody neutralizes human metapneumovirus In Vivo," *Journal of Virology* 93(19): e00342-19, 15 pages (published on-line Jul. 10, 2019).

Alvarez et al., "Human metapneumovirus persists in BALB/c mice despite the presence of neutralizing antibodies," *Journal of Virology*, 78(24): 14003-14011, Dec. 2004.

Alvarez and Tripp, "The immune response to human metapneumovirus is associated with aberrant immunity and impaired virus clearance in BALB/c mice," *Journal of Virology*, 79(10): 5971-5978, May 2005.

Brochet et al., "IMGT/V-QUEST: the highly customized and integrated system for IG and TR standardized V-J and V-D-J sequence analysis," *Nucleic Acids Research*, 36: W503-W508, May 23, 2008.

Cane et al., "Human metapneumovirus in a haematopoietic stem cell transplant recipient with fatal lower respiratory tract disease," *Bone Marrow Transplantation*, 36: 309-310, 2003.

Chang et al., "Human metapneumovirus (HMPV) binding and infection are mediated by interactions between the HMPV fusion protein and heparan sulfate," *Journal of Virology*, 86:3230-3243, Jan. 11, 2012.

Cox et al., "Human metapneumovirus is capable of entering cells by fusion with endosomal membranes," *PLOS Pathogens*, pp. 1-29, Dec. 2, 2015.

Cox et al., "The human metapneumovirus fusion protein mediates entry via an interaction with RGD-Binding integrins," *Journal of Virology*, 86(22):12148-12160, Nov. 2012.

De Swart et al., "Immunization of macaques with formalin-inactivated human metapneumovirus induces hypersensitivity to hMPV infection," *Vaccine* 25:8518-8528, 2007.

Dokos et al., "Fatal human metapneumovirus infection following allogeneic hematopoietic stem cell transplantation," *Transplant Infectious Disease*, 15:E97-E101, 2013.

(Continued)

*Primary Examiner* — Peter J Reddig
*Assistant Examiner* — Estella M. Gustilo
(74) *Attorney, Agent, or Firm* — Klarquist Sparkman, LLP; Susan Alpert Siegel; Gregory K. Scott

(57) ABSTRACT

Antibodies and antigen binding fragments that specifically bind to human metapneumovirus (hMPV) F protein and neutralize hMPV are disclosed. Nucleic acids encoding these antibodies, vectors and host cells are also provided. The disclosed antibodies, antigen binding fragments, nucleic acids and vectors can be used, for example, to inhibit an hMPV infection or detect a hMPV infection.

27 Claims, 31 Drawing Sheets

Specification includes a Sequence Listing.

(56) References Cited

OTHER PUBLICATIONS

Edwards et al., "Burden of human metapneumovirus infection in young children," *The New England Journal of Medicine*, 368:633-643, Feb. 14, 2013.

Englund et al., "Brief communication: fatal human metapneumovirus infection in stem-cell transplant recipients," *Annals of Internal Medicine*, 144:344-349, Mar. 7, 2006.

Falsey et al., "Human metapneumovirus infections in young and elderly adults," *The Journal of Infectious Diseases*, 187:785-790, Mar. 1, 2003.

Gilman et al., "Rapid profiling of RSV antibody repertoires from the memory B cells of naturally infected adult donors," *Sci. Immunol.* 1(6): 1-21, Dec. 16, 2016.

Groome et al., "Human metapneumovirus-associated severe acute respiratory illness hospitalization in HIV-infected and HIV-uninfected South African children and adults," *Journal of Clinical Virology*, 69:125-132, 2015.

"Palivizumab, a humanized respiratory syncytial virus monoclonal antibody, reduces hospitalization from respiratory syncytial virus infection in high-risk infants," *Pediatrics*, 102(3):531-537, Sep. 1998.

Haas et al., "Human metapneumovirus in adults," *Viruses* 5:87-110, Jan. 8, 2013.

Kan-o et al., "Human metapneumovirus infection in chronic obstructive pulmonary disease: Impact of glucocorticosteroids and interferon," *The Journal of Infectious Diseases*, 215:1536-1545, Apr. 4, 2017.

Klein et al., "Viral pathogens including human metapneumovirus are the primary cause of febrile respiratory illness in HIV-infected adults receiving antiretroviral therapy," *The Journal of Infectious Diseases*, 201(2):297-301, Jan. 15, 2010.

Krarup et al., "A highly stable prefusion RSV F vaccine derived from structural analysis of the fusion mechanism," *Nature Communications*, 6:1-12, Sep. 3, 2015.

Larcher et al., "Human metapneumovirus infection in lung transplant recipients: Clinical presentation and epidemiology," *The Journal of Heart and Lung Transplantation*, 24(11):1891-1901, Nov. 2005.

Liu et al., "Human metapneumovirus establishes persistent infection in the lungs of mice and is reactivated by glucocorticoid treatment," *Journal of Virology*, 83(13):6837-6848, Jul. 2009.

Madhi et al., "Human metapneumovirus-associated lower respiratory tract infections among hospitalized human immunodeficiency virus type 1 (HIV-1)-infected and HIV-1-uninfected African infants," *Clinical Infectious Diseases*, 37:1705-1710, Dec. 15, 2003.

Más et al., "Engineering, structure and immunogenicity of the human metapneumovirus F protein in the postfusion conformation," *PLOS Pathogens*, pp. 1-21, Sep. 9, 2016.

McLellan et al., "Structure of a major antigenic site on the respiratory syncytial virus fusion glycoprotein in complex with neutralizing antibody 101F," *Journal of Virology*, 84(23):12236-12244, Sep. 29, 2010.

McLellan et al., "Structure of respiratory syncytial virus fusion glycoprotein in the postfusion conformation reveals preservation of neutralizing epitopes," *Journal of Virology*, 85(15):7788-7796, Aug. 2011.

McLellan et al., "Structure of RSV fusion glycoprotein trimer bound to a prefusion-specific neutralizing antibody," *Science*, 340:1113-1117, May 31, 2013.

Mousa et al., "A novel pre-fusion conformation-specific neutralizing epitope on the respiratory syncytial virus fusion protein," *Nature Microbiology*, 2, 1-8, article 16271, Jan. 30, 2017.

Mousa et al., "Structural basis for nonneutralizing antibody competition at antigenic site II of the respiratory syncytial virus fusion protein," *PNAS*, E6849-E6858, Oct. 17, 2016.

Murphy et al., "Formalin-inactivated respiratory syncytial virus vaccine induces antibodies to the fusion glycoprotein that area deficient in fusion-inhibiting activity," *Journal of Clinical Microbiology*, 26(8):1595-1597, Aug. 1988.

Ngwuta et al., "Prefusion F-specific antibodies determine the magnitude of RSV neutralizing activity in human sera," *Science Transl. Med.*, 7(309):1-19, Oct. 14, 2015.

Panda et al., "Human metapneumovirus: review of an important respiratory pathogen," *International Journal of Infectious Diseases*, 25:45-52, 2014.

Peña et al., "Severe respiratory illness associated with human metapneumovirus in nursing home, New Mexico, USA," *Emerging Infectious Diseases*, 25(2):383-384, Feb. 2019.

Schildgen et al., "Human metapneumovirus: Lessons learned over the first decade," *Clinical Microbiology Reviews*, 24(4):734-754, Oct. 2011.

Schowalter et al., "Characterization of human metapneumovirus F protein-promoted membrane fusion: Critical roles for proteolytic processing and low pH," *Journal of Virology*, 80(22):10931-10941, Nov. 2006.

Schuster et al., "A broadly neutralizing human monoclonal antibody exhibits in vivo efficacy against both human metapneumovirus and respiratory syncytial virus," *Journal of Infectious Diseases*, 211:1-34, May 26, 2014.

Shafagati et al., "Human metapneumovirus—what we know now," *F1000Research*, 7(F1000 Faculty Rev.):135, pp. 1-11, 2018, updated Jul. 17, 2019.

Shah et al., "Human metapneumovirus infections in hematopoietic cell transplant recipients and hematologic malignancy patients: a systematic review," *Cancer Letters* 379:100-106, 2016.

Biacchesi et al., "Recombinant human metapneumovirus lacking the small hydrophobic SH and/or attachment G glycoprotein: deletion of G yields a promising vaccine candidate," *Journal of Virology*, 78(23):12877-12887, Dec. 2004.

Smith et al., "Rapid generation of fully human monoclonal antibodies specific to a vaccinating antigen," *Nature Protocols*, 4(3):372-384, 2009.

Stewart-Jones, "Structure-based design of a quadrivalent fusion glycoprotein vaccine for human parainfluenza virus types 1-4," *Proceedings of the National Academy of Sciences of the United States of America*, 115(48):12265-12270, Nov. 27, 2018.

Thornburg et al., "H7N9 influenza virus neutralizing antibodies that possess few somatic mutations," *The Journal of Clinical Investigation*, 126(4):1482-1494, Apr. 2016.

Tripp et al., "Respiratory syncytial virus: Targeting the G protein provides a new approach for an old problem," *Journal of Virology*, 92(3):1-8, Feb. 2018.

Van Den Hoogen et al., "A newly discovered human pneumovirus isolated from young children with respiratory tract disease," *Nature Medicine*, 7(6):719-724, Jun. 2001.

Van Den Hoogen et al., "Antigenic and genetic variability of human metapneumoviruses," *Emerging Infectious Diseases*, 10(4):658-666, Apr. 2004.

Van Den Hoogen et al., "Prevalence and clinical symptoms of human metapneumovirus infection in hospitalized patients," *The Journal of Infectious Diseases*, 188:1571-1577, Oct. 27, 2003.

Wen et al., "Structural basis for antibody cross-neutralization of respiratory syncytial virus and human metapneumovirus," *Nature Microbiology*, 2(16272):1-7, article 16272, Jan. 30, 2017.

Wen et al., "Structure of the human metapneumovirus fusion protein with neutralizing antibody identifies a pneumovirus antigenic site," *Nature Structural and Molecular Biology*, 19(4):461-463, Mar. 4, 2012.

Wu et al., "Characterization of the epitope for anti-human respiratory syncytial virus F protein monoclonal antibody 101F using synthetic peptides and genetic approaches," *Journal of General Virology*, 88:2719-2723, 2007.

Battles et al., "Structure and immunogenicity of pre-fusion-stabilized human metapneumovirus F glycoprotein," *Nature Communications* 8(1):1528, 11 pages (Nov. 16, 2017).

Corti et al., "Cross-neutralization of four paramyxoviruses by a human monoclonal antibody," *Nature* 501: 439-443 (2013).

Huang et al., "Antibody epitopes of Pneumovirus fusion proteins," *Frontiers in Immunology* 10(2778) 8 pages (Nov. 29, 2019).

International Search Report and Written Opinion for parent PCT Application No. PCT/US2020/033865 29 pages (mailed Sep. 22, 2020).

(56) References Cited

OTHER PUBLICATIONS

Mousa et al., "A potently neutralizing site III-specific human antibody prevents human metapneumovirus replication in vivo," *Journal of Immunology* 202(1 Supplement): 198.1 (May 1, 2019)(Abstract).

Mousa et al., "Human antibody recognition of antigenic site IV on Pneumovirus fusion proteins," *PLoS* 14(2):e1006837 19 pages (Feb. 22, 2018).

Ulbrandt et al., "Identification of antibody neutralization epitopes on the fusion protein of human metapneumovirus," *Journal of General Virology* 89(Pt 12):3113-3118 (Dec. 2008).

Ulbrandt et al., "Isolation and characterization of monoclonal antibodies which neutralize human metapneumovirus in vitro and in vivo," *Journal of Virology* 80(16):7799-7806 (Aug. 2006).

Williams et al., "A recombinant human monoclonal antibody to human metapneumovirus fusion protein that neutralizes virus in vitro and is effective therapeutically in vivo," *Journal of Virology* 81(15): 8315-8324 (ePUB May 23, 2007).

* cited by examiner

FIG. 2A

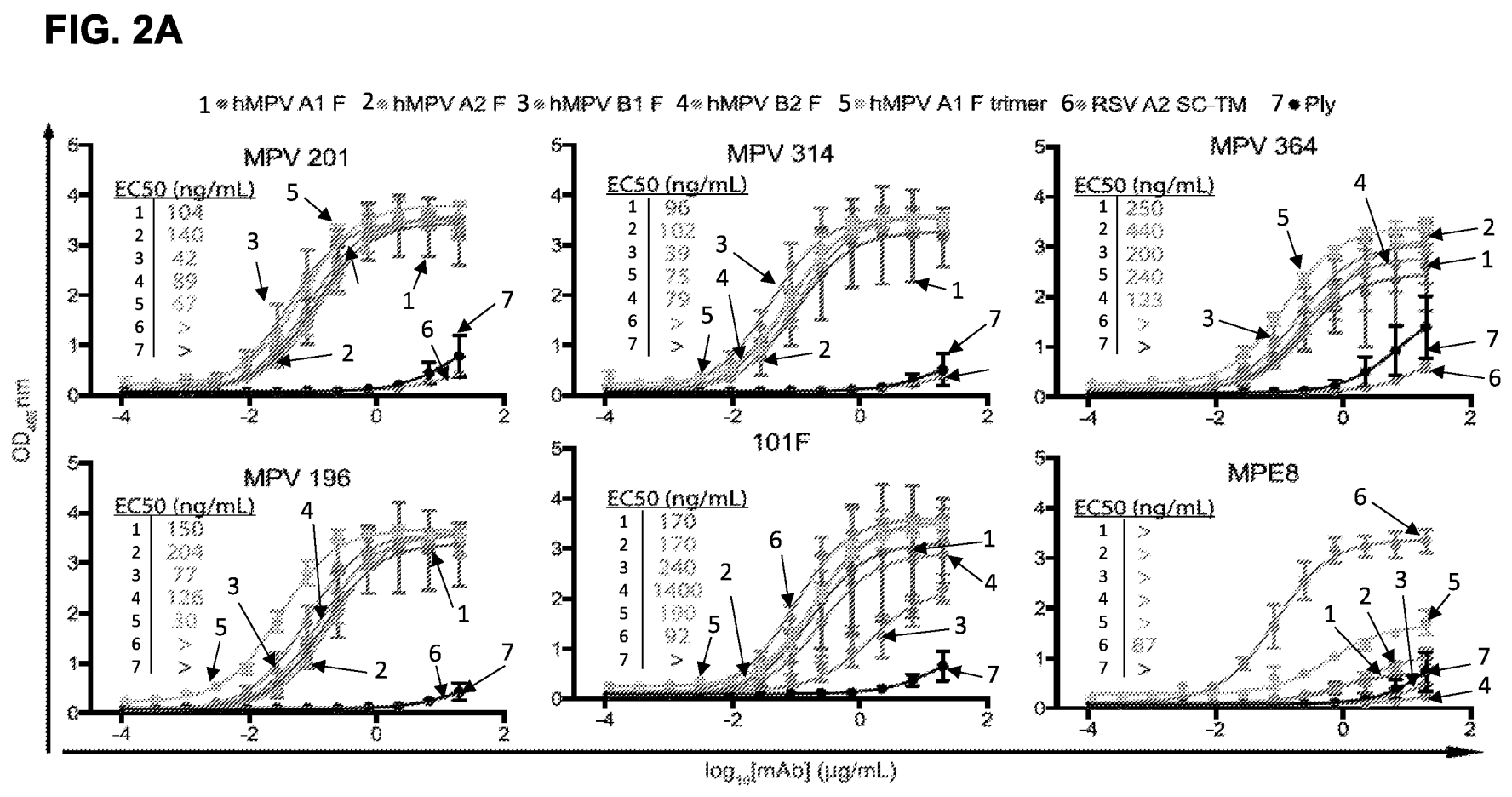

1 = hMPV A1 F   2 = hMPV A2 F   3 = hMPV B1 F   4 = hMPV B2 F   5 = hMPV A1 F trimer   6 = RSV A2 SC-TM   7 = Ply

MPV 201

EC50 (ng/mL)

| | |
|---|---|
| 1 | 104 |
| 2 | 140 |
| 3 | 42 |
| 4 | 89 |
| 5 | 97 |
| 6 | > |
| 7 | > |

MPV 314

EC50 (ng/mL)

| | |
|---|---|
| 1 | 96 |
| 2 | 102 |
| 3 | 39 |
| 5 | 75 |
| 4 | 79 |
| 6 | > |
| 7 | > |

MPV 364

EC50 (ng/mL)

| | |
|---|---|
| 1 | 250 |
| 2 | 440 |
| 3 | 200 |
| 5 | 240 |
| 4 | 123 |
| 6 | > |
| 7 | > |

MPV 196

EC50 (ng/mL)

| | |
|---|---|
| 1 | 150 |
| 2 | 200 |
| 3 | 77 |
| 4 | 135 |
| 5 | 98 |
| 6 | > |
| 7 | > |

101F

EC50 (ng/mL)

| | |
|---|---|
| 1 | 170 |
| 2 | 170 |
| 3 | 240 |
| 4 | 1400 |
| 5 | 180 |
| 6 | 92 |
| 7 | > |

MPE8

EC50 (ng/mL)

| | |
|---|---|
| 1 | > |
| 2 | > |
| 3 | > |
| 5 | > |
| 4 | > |
| 6 | 67 |
| 7 | > |

$OD_{450}$ nm $\log_{10}[mAb]$ ($\mu$g/mL)

FIG. 4B

```
391   395   399   403   407
      SIGSNRVGIIKQLNKGCSY
hMPV F

TASNKNRGIIKTFSNGCDY
RSV F
423   427   431   434   438
```

FIG. 4A hMPV A1 F hMPV B2 F

FIG. 6A

| Antibody | HC isotype | HC nucleotide |
|---|---|---|
| MPV196 | IgG1 | CAGGTGCAGCTACAGCAGTGGGGCGCAGGACTCTTGAAGCCTTCGGAGACCCTGTCCCTCACCTGCGCTGTCTATGGTGGGTCCTTCAGTGGTTACTCTTGGACCTGGATTCGCCAGCCCCCAGGGAAGGGGCTGGAGTGGATTGGGGAAATCAATCATAGTGGAAGCACCAACTACAACCCGTCCCTCCTCAAGAGTCGAGTCACCATATCAATAGACACGTCCAGGAACCAGTTCTCCCTGAAGCTGATCTCTGTGACCGCCGCGGACACGGCTGTATATTATTGTGCGAGAGGCGTGCGTGGTGGCTACAATTTGTGGCACTTTGACGTCTGGGGCCAGGGAACCCTGGTCACCGTCTCCTCAG (SEQ ID NO: 3) |
| MPV201 | IgG1 | CAGGTGCAGCTGGTGCAGTCTGGGGGAGGCGGGGTCCAGCCTGGGGAGGTCCCTGAGACTCTCCTGTGCAGCCTCTGGATTCATCTTCAGTGACTATGGCATGCACTGGGTCCGCCAGGCTCCAGGCAAGGGGCTGGAGTGGGTGGCAGTTATATCATATGATGGAAGTAATCAATACTATGCAGACTCCGTGAAGGGCCGATTCACCATCTCCAGAGACAATTCCAAGAACACGCTGTATCTGCAAATGAACAGTCTGAGAGTTGAGGACACGGCTGTATATTACTGTGCGAAGATCAAGGGAGGAGGTACTATTATATAGTAGTGGTTATCTAGACTACTGGGGCCAGGGAACCCTGGTCACCGTCTCCTCA (SEQ ID NO: 13) |
| MPV314 | IgG1 | CAGGTGCAGCTGGTGCAGTCTGGGGGAGGCGTGGTCCAGCCTGGGGAGGTCCCTGAGACTCTCCTGTGCAGCCTCTGGATTCAGTTCAGTGACTATGGCATGGACTGGGTCCGCCAGGCTCCAGGCAAGGGACTGGAGTGGGTGGCAGTTATATCATATGATGGAAGTAATCAATACTATGCAGACTCCGTGAAGGGCCGATTCACCGTCTCCAGAGACAATTCCAAGAACACGGTATATCTGCAAATGAACAGCCTGAGAGCTGAGGACACGGCTGTGTATTACTGTGCAAAGATGAAGTCGTAGGTATTATTAGTTCAGGGGTTATCTAGACTACTGGGGCCAGGGAACCCTGGTCACCGTCTCCTCA (SEQ ID NO: 23) |
| MPV364 | IgG1 | CAGGTGCAGCTGGTGCAGTCTGGGGGCTGAGGTGAAGAAGCCTGGGGCCTCAGTGAAGGTTCCTGCCAAGGCTTCTGGATACACCTTCACTGATTCTATCATCATGGGGTGCGCCAGGATCCCCGGACAAAGGCTTGAGTGGATGGGATGGATCAACGCTGGCAATGGTGACACAAATTACGCGCAGAAGTTCAGGAGCAGAGTCACAATTACCAGGACACATCTGCGAACAGCCTACAGGAGGTCAAGAAGCCTGAAATATGAAGATACGGCTATGTATTTCTGTGCAGAGTGGACCAATATTGTATTGGTGGTCTGCTATGGGGGAAAGAATTGGTTCGACCCCTGGGCAGGGAACCCTGGTCACCGTCTCCTCA (SEQ ID NO: 33) |
| MPV458 | IgG3 | CAGGGGAAGTTGGTGGAGTCTGGGGGAGGCGTGGTCCAACCTGGGGAGGTCCCTAAGACTCTCTTGTGCAGCCTCTGGATTCGACTTCAGTCGTTATGGTGCTCCACTGGGTCCGCCAGGCTCCAGGCAAGGGGCTGGAGTGGGTGGCAGTTATTGTATACGCTGGAAGTAATAAATATTATGCAGACTCCGTGAAGGGCCGATTCACCATCTCCAAAGATAATTCTAAGAACACGACGATGCATCTGCAAATGAGCGACCTGAGAGACGCAACTGAGAACTGGACCGTCGTTTATTACTGTGCGAGAGACCAGGCTTTTGATCTCTGGGGCCAAGGGACCACGGTCACCGTCTCCTCA (SEQ ID NO: 51) |
| MPV465 | IgG1 | GAAGTGCAGCTGGTGGAGTCTGGGGGAGGCGTGGTCCAGCCTGGGAGGTCCCTGAGACTCTCCTGTGTAGCGTCTGGATTCACCATTCACATTCGGGTACTTATGGCATGGCATTACTGGGTCCGCCAGTGTCCGCCAGGCTCCAGGCAAGGGGCTGGAGTGGGTGGCTTTTATATGGCTTGATGGAAGTAAGACTTACTATGCCGCCATATCGCTGTGGCCATATCGCTGTGGCCATATGAAAGGGCCAGATTCACCGTCTCGAAGGGACGCACGGCGATGTACTACTGTGCGAGAGCCCCAGGCTCGGTTGGTATGACACTCTGAAAGGGTGGTTCGACCCCTGGGGCCAGGGAACCCTGGTCACCGTCGCCCTCAG (SEQ ID NO: 61) |

FIG. 6B

| Antibody | HC isotype | HC AA |
|---|---|---|
| MPV196 | IgG1 | QVQLQQWGAGLLKPSETLSLTCAVYGGSFSGYSWTWIRQPPGKGLEWI GEINHSGSTNYNPSLKSRVTISIDTSRNQFSLKLISVTAADTAVYYCARGV RGGYNLWHFDVWGQGTLVTVSS (SEQ ID NO: 1) |
| MPV201 | IgG1 | QVQLVQSGGGVQPGRSLRLSCAASGFIFSDYGMHWVRQAPGKGLE WVAVISYDGSNQYYADSVKGRFTISRDNSRNTLYLQMNSLRVEDTAVYY CAKDQGRRYYYSSGYLDYWGQGTLVTVSS (SEQ ID NO: 11) |
| MPV314 | IgG1 | QVQLVQSGGGVVQPGRSLRLSCAASGFSFSDYGMDWVRQAPGKGLE WVAVISYDGSNQYYADSVKGRFTVSRDNSKNTVYLQMNSLRAEDTAVY FCAKDESRRYYYSSGIHSHWGQGTLVTVSS (SEQ ID NO: 21) |
| MPV364 | IgG1 | QVQLVQSGAEVKKPGASVKVSCKASGYTFTHDSIHWVRQAPGQRLEW MGWINVGNGDTKSSQKFQDRLTITRDTSANTAYMEVRSLKYEDTAMYF CARVDQYCIGGVCYGGKNWFDPWGQGTLVTVSS (SEQ ID NO:31) |
| MPV458 | IgG3 | QGKLVESGGGVIQPGRSLRLSCAASGFDFSRYGLHWVRQAPGKGLEW VAVIVYAGSNKYYADSVKGRFTISKDNSKNTMHLQMSDLRTEDTAVYYC ARDQAFDLWGQGTMVTVSS (SEQ ID NO: 49) |
| MPV465 | IgG1 | EVQLVESGGGVVQPGTSLRLTCVASGFTFGTYGMYWLRQSPGKGLEW VAFIWLDGSKTYYADSVKGRFTVSRDNSKNKLYLEMNSLSAEDTAMYY CARAPGSVWYDTRGHMKGWFDPWGQGTLVTVAS (SEQ ID NO: 59) |

FIG. 6C

| Antibody | LC isotype | LC nucleotide |
|---|---|---|
| MPV196 | lamda | TCCTATGAGCTGAGTCAGTCACCCTCAGTGTCCGTGTCTCCAGGACAGACAGCCAGAATCACCTGCTCTGGAGATAAATTGGGGAATAAATATGCTTCCTGGTATCAGCAGAAACCAGGCCAGTCCCCTGTGCTGGTCATCTATCAGGATGAGAAGCGGCCCTCAGGGATCCCTGAGCGATTCTCTGGCTCCAACTCTGGGAACACAGCCACTCTGACCATCGGCGGGACCCAGGCTATGAGGATGAGGCTGACTATTCCTGTCAGCGGTGGGACGGCAGAACTGCTGTGGTTTCGGCGGAGGGACCAAGCTGACCGTCCTAG (SEQ ID NO: 4) |
| MPV201 | kappa | GACATTGTGATGACCCAGTCTCCAGCGCGCCCGTCTGTGTCTCCAGGGGAACGAGCCACCCTCTCCTGCAGGGCCAGTCACAGTGTTGCCAGCAACCTGGCCTGGTACCAGCAGAAACCTGGCCAGGCTCCCAGGCTCCTCATCTCTGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTATAATAGGTGGCCTCCGTGGACGTTCGGCCAAGGGACCAAGGTGGAAATCAAAC (SEQ ID NO: 14) |
| MPV314 | kappa | GACATTGTGATGACCCAGTCTCCAGCACCCTCTCTGTCTGTGTCTCCAGGGGAAAGAGCCACCCTCTCCTGCAGGGCCAGTCAGAGTGTTAGCCGCGAACTTAGCCTGGTACCAGCAGAAACCTGGCCAGGCTCCCAGGCTCCTCATCTTTGGTGCGTCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCACCAGTATAATAATACTGGCCTCCGGGGACTTTTGGCCAGGGGACCAAGGCTGGAGATCAAA (SEQ ID NO: 24) |
| MPV364 | lamda | TCCTATGAGCTGAATCAGCCACCCTCCGGTGTCGGTGGCCACCCCAGGGCAGGGCAGACGGCCATGATTACCTGTGGGGGATATTATGTCGGAGTTAAAAGTTTGCACTGGTACCAACAGAAGCCAGGCCAGGCCCCTGTGCTGGTCGTCATGATGATAGGCGACCGGCCCTCTGGGATCCCTGAGCGATTCTCTGGCTCCAACTCTGGGAACATCTGGGATAGGGTGTGGGACAACTGATCATCAGTAGGGTCGAAGCCGGGGATGAGGCCGACTATTACTGTCAGGTGTGTGGGGATAGTGATCATCCTTATGTCTTTCGGAACTGGGACCACGGGTCACCGTCCTG (SEQ ID NO: 34) |
| MPV458 | kappa | GACATCCAGATGACCCAGTCTCCTCCCTCTGTCTGCATCTGTAGGAGACAGAGTCACCATCACTTGCCAGGCGAGTCAGGGCATTAGCAGTTATTTAGCCTGTTATCAGCAGAAACCAGGGAAAGCCCCTAAACTCCTGATCTTCGATGCATCCCATTTGGAAAGAGGGGTCCCATCAAGGTTCAGTGGCAGTGGATATGGGACAGATTTTACTTTCACCATCAGCAGCCTGCAGCCTGAAGATATTGCAACAATATTACTGTCAACAGTATGTGAATCTCCGGATCAGCTTCGGCCAAGGGACACGACTGGAGATCGAGATCAAAA (SEQ ID NO: 52) |
| MPV465 | lamda | CAGTCTGTGCTGACTCAGACACCCTCAGTGTCTGGGACCCCCGGGCAGAGGGTCACCATCTCTTGTTCTGGAAGCAGCTCCAACATCGAAAATAATTATTATACTGGTACCAGCAGCTCCCAGGAACGGCCCCAGACTCCTCATCTATGGTGATAATCGGCGGCCCTCAGGGGTCCCTGACCGATTCTCCGGCTCCAAGTCTGGCACCTCAGCCTCCCTGGCCATCAGTGGGCTCCGGTCCGAAGATGAGGCTGATTATTACTGTGCAACATGGGATGACAACCTGAGTGGTCCGGTGTTCGGCGGAGGGACCAAGGTGACCGTCCTAG (SEQ ID NO: 62) |

FIG. 6D

| Antibody | LC isotype | LC AA |
|---|---|---|
| MPV196 | lamda | SYELSQSPSVSVSPGQTARITCSGDKLGNKYASWYQQKPGQSPVLVIYQDDKRPSGIPERFSGSNSGNTATL TIGGTQAMDEADYSCQAWDGRTAVVFGGGTKLTVL (SEQ ID NO: 2) |
| MPV201 | kappa | DIVMTQSPAALSVSPGERATLSCRASHSVASNLAWYQQKPGQAPRLLISGASTRATGIPARFSGSGSGTEFT LTISSLQSEDFAVYYCQQYNRWPPWTFGQGTKVEIK (SEQ ID NO: 12) |
| MPV314 | kappa | DIVMTQSPATLSVSPGERATLSCRASQSVSRNLAWYQQKPGQAPRLLIFGASTRATGIPARFSGSASGTEFT LTISSLQSEDFAVYYCHQYNYWPPGTFGQGTRLEIK (SEQ ID NO: 22) |
| MPV364 | lamda | SYELNQPPSVSVAPGQTAMITCGGYYVGVKSLHWYQQKQAPVLVVHDDSDRPSGIPERFSGSKSGDTA TLIISRVEAGDEADYYCQVWDRDSDHPYVFGTGTTVTVL (SEQ ID NO: 32) |
| MPV458 | kappa | DIQMTQSPASLSASVGDRVTITCQASQGISRSVNWYQQKPGKAPKLLIFDASHLERGVPSRFSGSGSGYGTDFT FTISSLQPEDIATYYCQQYDNLRISFGQGTRLEIK (SEQ ID NO: 50) |
| MPV465 | lamda | QSVLTQTPSVSGTPGQRVTISCSGSSSNIENNYLYWYQQLPGTAPKLLIYGDNRRPSGVPDRFSGSKSGTSA SLAISGLRSEDEADYYCATWDDNLSGPVFGGGTKVTVL (SEQ ID NO: 60) |

FIG. 6E

| Antibody | HC isotype | HC CDR1 | HC CDR2 | HC CDR3 |
|----------|-----------|---------|---------|---------|
| MPV196 | IgG1 | GGSFSGYS (SEQ ID NO: 5) | INHSGST (SEQ ID NO: 6) | ARGVRGGYNLWHFDV (SEQ ID NO: 7) |
| MPV201 | IgG1 | GFIFSDYG (SEQ ID NO:15) | ISYDGSNQ (SEQ ID NO: 16) | AKDQGRRYYYSSGYLDY (SEQ ID NO: 17) |
| MPV314 | IgG1 | GFSFSDYG (SEQ ID NO: 25) | ISYDGSNQ (SEQ ID NO: 26) | AKDESRRYYYSSGIHSH (SEQ ID NO: 27) |
| MPV364 | IgG1 | GYTFTHDS (SEQ ID NO: 35) | INVGNGDT (SEQ ID NO: 36) | ARVDQYCIGGVCYGGKNWFDP (SEQ ID NO: 37) |
| MPV458 | IgG3 | GFDFSRYG (SEQ ID NO: 53) | IVYAGSNK (SEQ ID NO: 54) | ARDQAFDL (SEQ ID NO: 55) |
| MPV465 | IgG1 | GFTFGTYG (SEQ ID NO: 63) | IWLDGSKT (SEQ ID NO: 64) | ARAPGSVWYDTRGHMKGWFDP (SEQ ID NO: 65) |

FIG. 6F

| Antibody | LC isotype | LC CDR1 | LC CDR2 | LC CDR3 |
|----------|-----------|---------|---------|---------|
| MPV196 | lamda | KLGNKY (SEQ ID NO: 8) | QDD (SEQ ID NO: 9) | QAWDGRTAVV (SEQ ID NO: 10) |
| MPV201 | kappa | HSVASN (SEQ ID NO: 18) | GAS (SEQ ID NO: 19) | QQYNRWPPWT (SEQ ID NO: 20) |
| MPV314 | kappa | QSVSRN (SEQ ID NO: 28) | GAS (SEQ ID NO: 29) | HQYNYWPPGT (SEQ ID NO: 30) |
| MPV364 | lamda | YVGVKS (SEQ ID NO: 38) | DDS (SEQ ID NO: 39) | QVWDRDSDHPYV (SEQ ID NO: 40) |
| MPV458 | kappa | QGISRS (SEQ ID NO: 56) | DAS (SEQ ID NO: 57) | QQYDNLRIS (SEQ ID NO: 58) |
| MPV465 | lamda | SSNIENNY (SEQ ID NO: 66) | GDN (SEQ ID NO: 67) | ATWDDNLSGPV (SEQ ID NO: 68) |

FIG. 7A

| | | IV | DS7 | | 66-87 | | III | |
| --- | --- | --- | --- | --- | --- | --- | --- | --- |
| | | 101F | DS7 | 196 | 465 | 458 | 364 | MPE8 |
| IV | 101F | -2 | 37 | 77 | 60 | 81 | 89 | 37 |
| DS7 | DS7 | 104 | 13 | 23 | 101 | 105 | 104 | 71 |
| | 196 | 82 | 3 | 3 | 81 | 81 | 78 | 1 |
| 66-87 | 465 | 105 | 77 | 109 | 3 | 22 | 133 | 78 |
| | 458 | 95 | 66 | 93 | -14 | 8 | 116 | 64 |
| III | 364 | 73 | 34 | 58 | 70 | 74 | 22 | 10 |
| | MPE8 | 90 | 36 | 30 | 89 | 92 | 52 | 2 |

FIG. 19
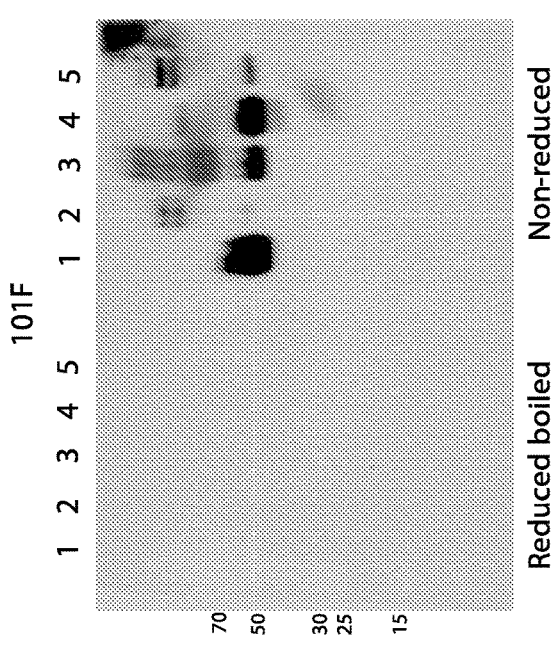
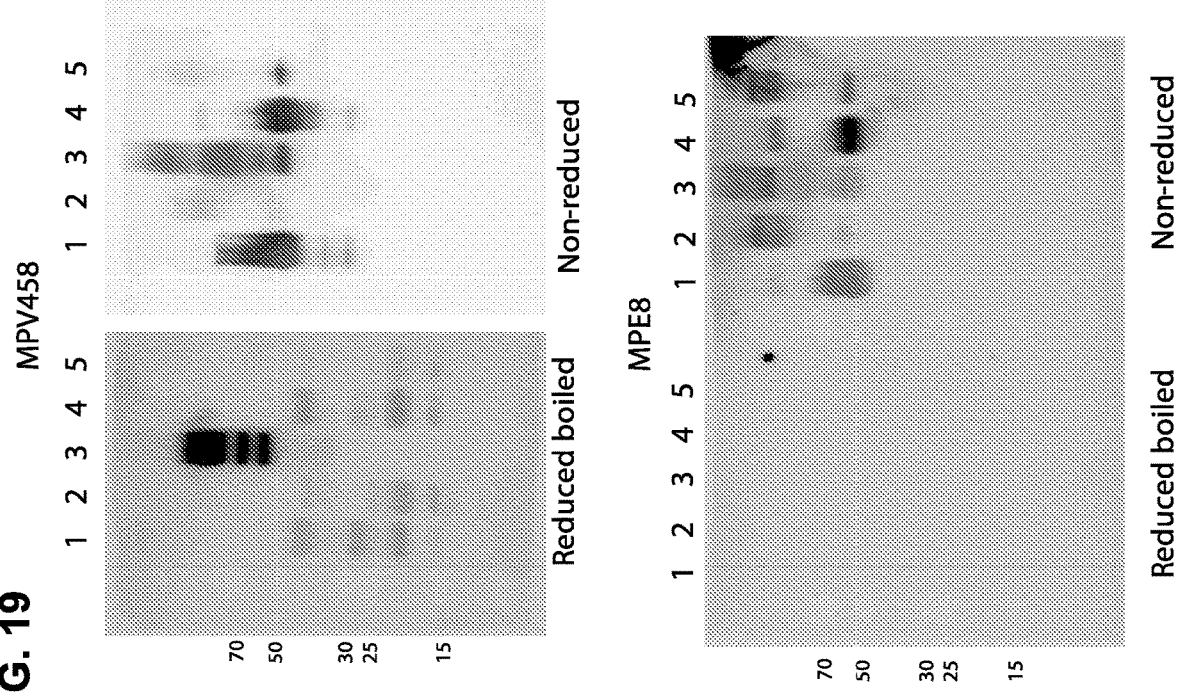
1. hMPV B2 F monomer (trypsin)
2. hMPV B2 F trimer (trypsin)
3. hMPV B2 F trimer
4. hMPV A1 F monomer
5. hMPV A1 F trimer hMPV infected cells

FIG. 20B
hMPV infected cells
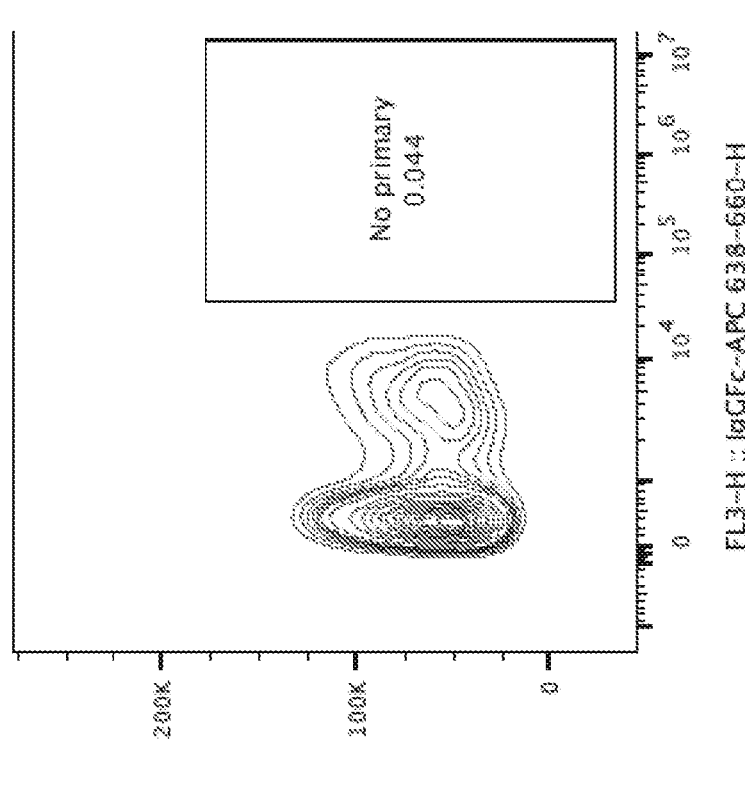
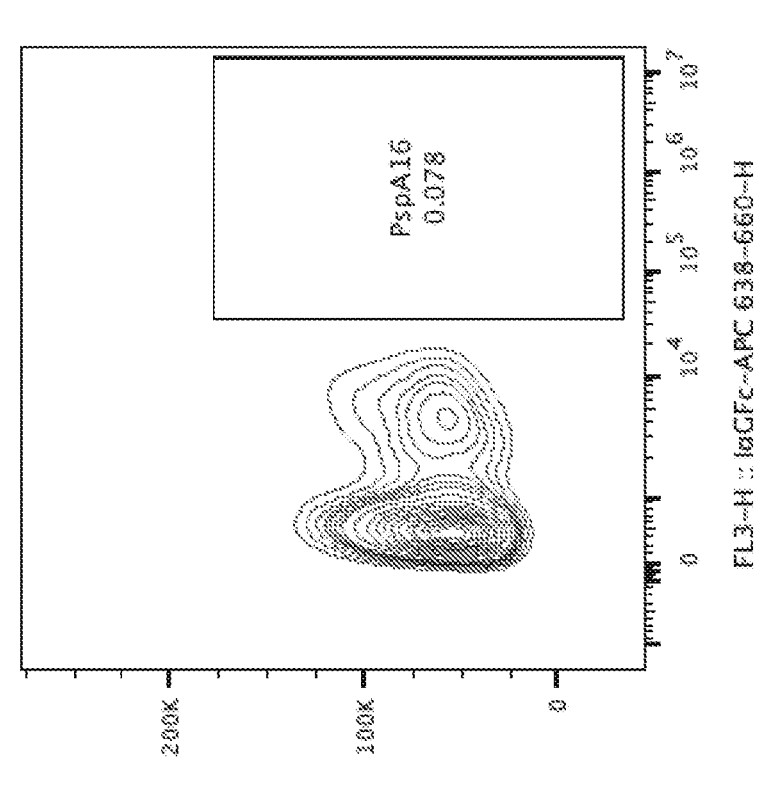

FIG. 20D
uninfected cells
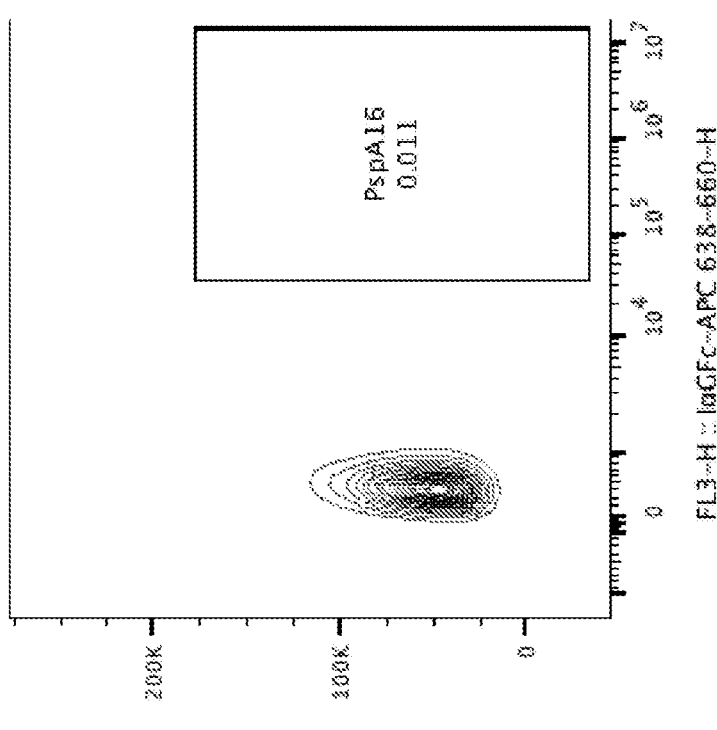
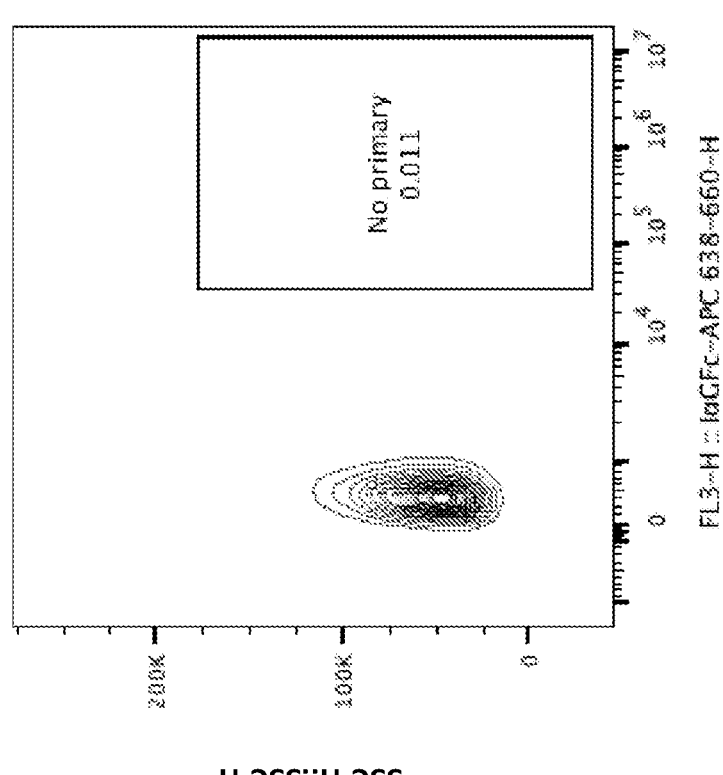

ANTIBODIES THAT BIND HUMAN METAPNEUMOVIRUS FUSION PROTEIN AND THEIR USE

CROSS REFERENCE TO RELATED APPLICATIONS

This is a § 371 U.S. national stage of International Application No. PCT/US2020/033865, filed May 20, 2020, which claims the benefit of U.S. Provisional Application No. 62/851,020, filed May 21, 2019, which is incorporated herein by reference.

STATEMENT OF GOVERNMENT SUPPORT

This invention was made with government support under grant nos. 1R01AI143865, K01OD026569 and UL1TR002378 awarded by National Institutes of Health of the United States government. The government has certain rights in the invention.

FIELD OF THE DISCLOSURE

This related to the field of metapneumoviruses, specifically to monoclonal antibodies and antigen binding fragments thereof that specifically bind the human metapneumovirus F protein.

BACKGROUND

Human metapneumovirus (hMPV) is a significant respiratory pathogen and is a member of the order Mononegavirales and the Pneumoviridae family of viruses, which also includes respiratory syncytial virus (RSV). The members of this family are single-stranded, non-segmented, negative-sense RNA viruses, and have similar life cycles (Schildgen et al. 2011. Clin Microbiol Rev 24:734-754). Infants and the elderly are the major groups for which hMPV infection may require hospitalization (Panda et al. 2014. Int J Infect Dis 25:45-52; Falsey et al. 2003. J Infect Dis 187:785-790; van den Hoogen et al. 2003. J Infect Dis 188:1571-1577; Madhi et al. 2003. Clin Infect Dis 37:1705-1710; Haas et al. 2013. Clin Infect Dis 5:87-110.). In addition, hMPV infection is frequent in immunocompromised patients including lung transplant (Larcher et al. J Hear Lung Transpl 24:1891-1901) and hematopoietic stem-cell transplant recipients (Cane et al. 2003. Bone Marrow Transplant 31:309-310; Englund et al. 2013. Ann Intern Med 144:344-34: Dokos et al. 2013. Transpl Infect Dis 15:97-101; Shah et al. 2016. Cancer Lett 379:100-106), with several deaths associated with viral infection (Cane et al. 2003. Bone Marrow Transplant 31:309-310; Englund et al. 2013. Ann Intern Med 144:344-34; Dokos et al. 2013. Transpl Infect Dis 15:97-101; Shah et al. 2016. Cancer Lett 379:100-106)). hMPV is a significant cause of febrile respiratory illness in HIV-infected patients (Klein et al. 2010. J Infect Dis 201:297-301.), and has increased incidence in several HIV-infected age groups (Groome et al. 2015. J Clin Virol 69:125-132). hMPV has also been linked to exacerbations of chronic obstructive pulmonary disease (Kan-o et al. 2018. J Infect Dis 215:1536-1545). hMPV was initially identified in 2001 (van den Hoogen et al. 2001. Nat Med 7:719-724), and the clinical features of hMPV infection display as mid-to-upper respiratory tract infection, and can be severe enough to cause life-threatening bronchiolitis and pneumonia. A nursing home outbreak of hMPV supports the need for effective vaccines and therapeutics in the elderly (Pefla et al. 2019.

Emerg Infect Dis 25:https://doi.org/10.3201/eid2502.181298). There are no licensed vaccines to protect against hMPV, but several candidates have been examined in animal models, including live-attenuated viruses, recombinant viruses, vectored vaccines, and recombinant surface proteins (Shafagati and Williams. 2018. F1000Res 7:135). Currently, only one vaccine has been tested in clinical trials (NCT01255410), however, results of the trial are not yet available. A need remains for additional agents that target hMPV.

SUMMARY OF THE DISCLOSURE

Disclosed is an isolated monoclonal antibody or antigen binding fragment thereof, that includes:

a) a heavy chain variable region and a light chain variable region comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 1 and 2, respectively;

b) a heavy chain variable region and a light chain variable region comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 11 and 12, respectively;

c) a heavy chain variable region and a light chain variable region comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 21 and 22, respectively;

d) a heavy chain variable region and a light chain variable region comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 31 and 32, respectively;

e) a heavy chain variable region and a light chain variable region comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 49 and 50, respectively; or f) a heavy chain variable region and a light chain variable region comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 59 and 60, respectively, wherein the monoclonal antibody specifically binds to human metapneumovirus (hMPV) F protein and neutralizes hMPV. In specific non-limiting examples, the CDRs can be identified using the e Kabat, Chothia or IMGT numbering scheme.

In some embodiments, a) the HCDR1, the HCDR2, the HCDR3, the LCDR1, the LCDR2, and the LCDR3 comprise the amino acids sequences set forth as SEQ ID NOs: 5, 6, 7, 8, 9 and 10, respectively; b) the HCDR1, the HCDR2, the HCDR3, the LCDR1, the LCDR2, and the LCDR3 comprise the amino acids sequences set forth as SEQ ID NOs: 15, 16, 17, 18, 19 and 20, respectively; c) the HCDR1, the HCDR2, the HCDR3, the LCDR1, the LCDR2, and the LCDR3 comprise the amino acids sequences set forth as SEQ ID NOs: 25, 26, 27, 28, 29 and 30, respectively; or d) the HCDR1, the HCDR2, the HCDR3, the LCDR1, the LCDR2, and the LCDR3 comprise the amino acids sequences set forth as SEQ ID NOs: 35, 36, 37, 38, 39 and 40, respectively;

e) the HCDR1, the HCDR2, the HCDR3, the LCDR1, the LCDR2, and the LCDR3 comprise the amino acids sequences set forth as SEQ ID NOs: 53, 54, 55, 56, 57, and 58, respectively; or the HCDR1, the HCDR2, the HCDR3, the LCDR1, the LCDR2, and the LCDR3 comprise the amino acids sequences set forth as SEQ ID NOs: 63, 64, 65, 66, 67, and 68, respectively.

In some embodiments, the antibody or antigen binding fragment is conjugated to an effector molecule or a detectable marker.

Bispecific antibodies comprising the antibody or antigen binding fragment are also disclosed In further embodiments, nucleic acids and vectors encoding the antibody, antigen binding fragment, or a $V_H$ or $V_L$ of the antibody or antigen binding fragment.

In more embodiments, pharmaceutical compositions are disclosed for use in inhibiting an hMPV infection that includes an effective amount of the antibody, antigen binding fragment, nucleic acid molecule, or vector, and a pharmaceutically acceptable carrier.

In further embodiments, disclosed is a method of producing an antibody or antigen binding fragment that specifically binds to hMPV F protein In some embodiments, methods are also disclosed for detecting the presence of hMPV in a biological sample from a human subject.

In additional embodiments, methods are disclosed for inhibiting an hMPV infection in a subject, comprising administering an effective amount of the antibody, antigen binding fragment, nucleic acid molecule, vector, or pharmaceutical composition to the subject, wherein the subject has or is at risk of an hMPV infection.

The foregoing and other features and advantages of the invention will become more apparent from the following detailed description of several embodiments which proceeds with reference to the accompanying figures.

BRIEF DESCRIPTION OF THE FIGURES

FIGS. 2A-2B. Binding affinity of the hMPV F protein-specific mAbs. (A) ELISA binding curves of the isolated mAbs with controls to the four subtypes of the hMPV F protein, including a trypsin-cleaved trimeric hMPV A1 F protein. Pre-fusion RSV F protein (SC-TM) was utilized to determine if any mAb cross-reacts with RSV F. No cross-reactivity was observed except for mAbs 101F and MPE8. The pneumolysin toxin from Streptococcus pneumoniae was used as a negative binding control. Each point represents the average of three replicates, and error bars represent 95% confidence intervals. Data are representative of two independent experiments. $EC_{50}$ values are inlaid in each graph and are color coded with the legend at the top of the curves. (B) Association and dissociation curves for MPV364, MPV196, and MPV314 using biolayer interferometry. The hMPV B2 F protein was loaded onto anti-penta-HIS biosensors. Curves include the association for 120 s followed by dissociation for 600 s. $K_{on}$, $K_{off}$, and $K_D$ values are displayed below each curve and were calculated as the average of values calculated from each binding curve. Antibody concentrations for each experiment are 666 nM, 333 nM, 167 nM, 83 nM, and 42 nM. A reference curve containing buffer only was subtracted from each curve.

FIGS. 4A-4B. Epitope binning analysis for mAbs binding hMPV F protein. (A) Epitope binning for mAbs binding hMPV B2 F and hMPV A1 F proteins. Data indicate the percent binding of the competing antibody in the presence of the primary antibody, compared with the competing antibody alone. Cells filled in black indicate full competition, in which ≤33% of the un-competed signal was observed, intermediate competition (gray) if signal was between 33% and 66%, and noncompeting (white) if signal was ≥66%. Antigenic sites are highlighted at the top and side based on competition-binding with the control mAbs MPE8 and 25P13 (site III), DS7, and 101F (site IV). (B) The crystal structure of the RSV F protein in complex with MPE8 (PDB ID: 5U68) is overlaid with the crystal structure of the hMPV F protein in complex with DS7 Fab (PDB: 4DAG). Based on the competition profile of MPV364, the mAb likely binds at an angle shifted away from DS7, since no competition was observed between DS7 and MPV364. This is in contrast to site III mAbs MPE8 and 25P13, which both compete at least one-directionally with DS7. Site III is defined by binding to MPE8. Site IV is shown below in FIG. 4B (MPV is SEQ ID NO: 45; RSV is SEQ ID NO: 46).

FIGS. 6A-6F are tables of sequences. (A) heavy chain (HC) nucleotide, SEQ ID NOs: 3, 13, 23 33, 51 and 61(B) HC amino acid (AA), SEQ ID NOs: 1, 11, 21, 31, 49 and 59 (C) light chain (LC) nucleotide, SEQ ID NOs: 4, 14, 24, 34, 52 and 62 (D) LC AA, SEQ ID NOs: 2, 12, 22, 32, 50 and 60, (E) HC complementarity determining region (CDR)1, HC CDR2 and HC CDR3, SEQ ID NOs: 5, 6, and 7, SEQ ID NOs: 15, 16 and 17, SEQ ID NOs: 25, 26 and 27 and SEQ ID NOs: 35, 36 and 37, SEQ ID NOs: 53, 54 and 55; and SEQ ID NOs: 63, 64 and 65 (F) LC CDR1, LC CDR2 and LC CDR3, SEQ ID NOs: 8, 9, and 10, SEQ ID NOs: 18, 19, and 20, SEQ ID NOs: 28, 29, and 30, SEQ ID NOs: 38, 39, and 40, SEQ ID NOs: 56, 57 and 58, and SEQ ID NOs: 66, 67 and 68. The CDRs were determined using IMGT.

FIGS. 7A-7D. Binding and neutralizing properties of MPV458 and MPV465. (A) Epitope binning of the hMPV F-specific mAb panel. Epitope control mAbs include 101F (site IV), DS7 and MPV196 (DS7 epitope), and MPV364 and MPE8 (site III). MPV465 and MPV458 do not compete with known mAbs, and compete with each other for binding, suggesting both mAbs bind at a previously undiscovered antigenic site. Data indicate the percent binding of the competing antibody in the presence of the primary antibody, compared with the competing antibody alone. Cells filled in black indicate full competition, in which ≤33% of the uncompeted signal was observed; cells in gray indicate intermediate competition, in which the signal was between 33% and 66%; and cells in white indicate noncompetition, where the signal was ≥66%. Antigenic sites are highlighted at the top and side based on competition binding with the control mAbs. (B) Plaque neutralization curves for MPV458 and MPV465 with controls. Both MPV458 and MPV465 are neutralizing, while MPV458 has neutralizing properties similar to MPE8 and 101F. $IC_{50}$ values are inlaid in each curve. The pneumococcal-specific antibody Ply34 was used as a negative control. Data points are the average of three replicates and error bars are 95% confidence intervals. Data are shown from one experiment and are representative of two independent experiments. (C) ELISA binding curves for hMPV F-specific mAbs against monomeric and trimeric hMPV B2 F protein that was treated with trypsin. MPV458 and MPV465 have lower $EC_{50}$ values (higher affinity) for monomeric hMPV B2 F than trimeric hMPV B2 F. Binding curves and $EC_{50}$ values are colored according to the legend. Each data point is the average of four replicates and error bars represent 95% confidence intervals. Data are representative of one experiment from two independent replicates. (D) Binding curves from biolayer interferometry. hMPV 130-BV coated anti-penta-HIS biosensors were exposed to mAbs for 120 s before dissociating in buffer for 600 s. Binding constants are displayed within each graph. For mAbs that exhibited limited dissociation, only association constants are displayed.

FIG. 19. Western blot analysis of MPV458 binding to the 66-87 epitope. A panel of hMPV F protein constructs were subjected to SDS-PAGE separation before transfer to a PVDF membrane. Specific mAbs listed above each panel were used as primary antibodies. MPV458 bound to all constructs tested including boiled samples, while MPE8 and 101F bound only to samples with limited treatment.

FIGS. 20A-20D. Flow cytometric analysis of hMPV F infected LLC-MK2 cells. Twenty-four hours after infection, cells were harvested and stained with mAbs indicated. MPV458 and MPE8 induced a fluorescent shift in infected cells as compared to the pneumococcal-specific mAb PspA16.

SEQUENCES

Figures 1A, 1B, 1C:
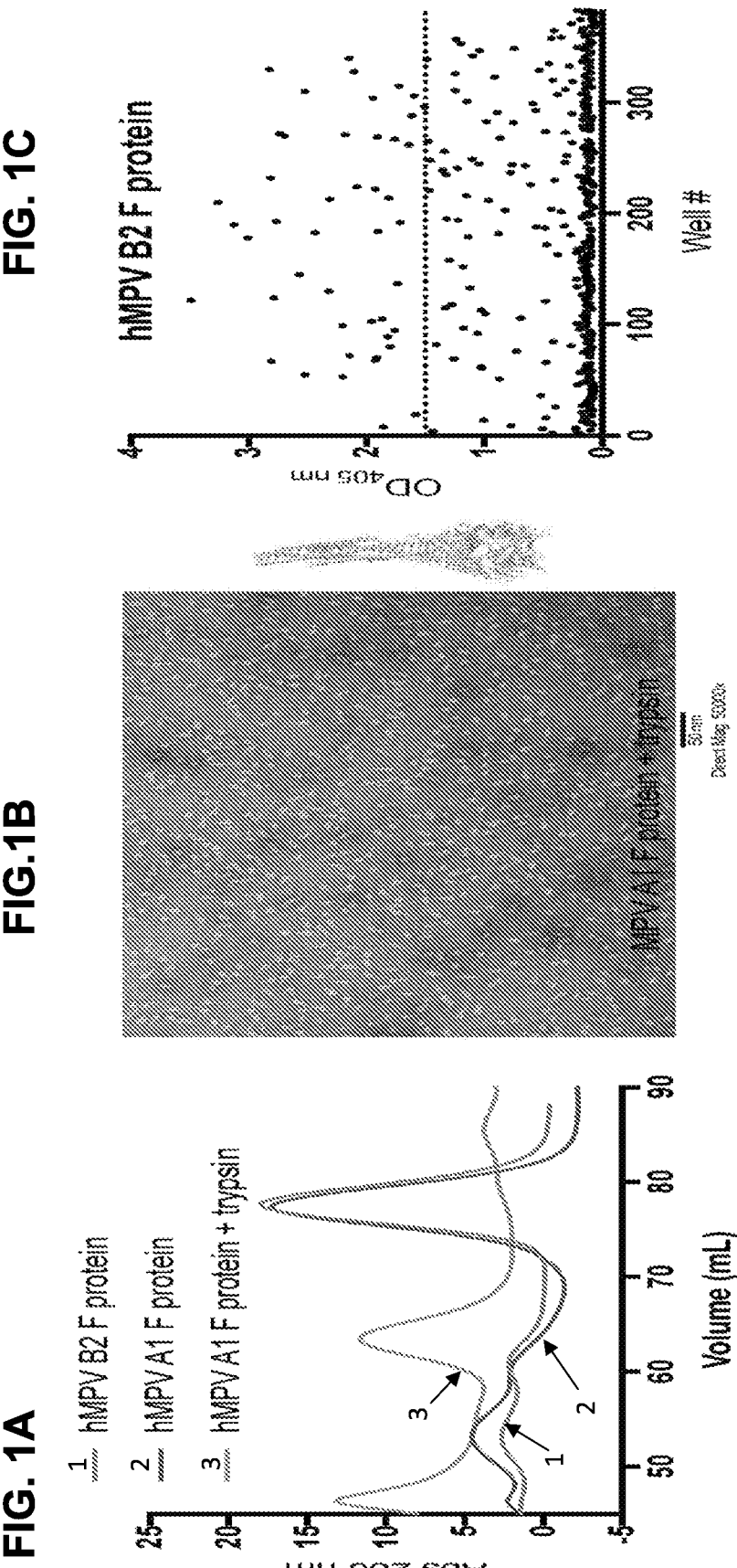
FIGS. 1A-1C. Characterization of recombinantly expressed hMPV F proteins, and hMPV F-specific B cell frequency. (A) Size exclusion chromatogram of hMPV F proteins. hMPV B2 F and hMPV A1 F proteins are monomeric based on elution volumes. Upon trypsin cleavage, hMPV A1 F forms trimers as determined by a shift in the elution profile. (B) Negative-stain electron microscopy image of the MPV A1 F protein after trypsin cleavage. The protein resembles the crystal structure of post-fusion hMPV F protein (PDB: 5L1X), which is displayed for reference next to the EM image. (C) ELISA binding data of bulk B cell supernatants binding to the hMPV B2 F protein from Donor 5. Select wells with signal greater than 1.5 Abs units were chosen for electrofusion for hybridoma generation.

The sequences are presented in FIG. 6A-6 F. The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named Sequence_Listing.txt, created Nov. 17, 2021, 30.3 KB, which is incorporated by reference herein. In the accompanying sequence listing:

SEQ ID NO: 1 is the amino acid sequence of the heavy chain variable domain of MPV196.

SEQ ID NO: 2 is the amino acid sequence of the light chain variable domain of MPV196.

SEQ ID NO: 3 is a nucleic acid sequence encoding the heavy chain variable domain of MPV196.

SEQ ID NO: 4 is a nucleic acid sequence encoding the light chain variable domain of MPV196.

SEQ ID NOs: 5, 6, and 7 are the IMGT HCDR1, HCDR2 and HCDR3, respectively, of MPV196.

SEQ ID NOs: 8, 9, and 10 are the IMGT LCDR1, LCDR2 and LCDR3, respectively of MPV196.

SEQ ID NO: 11 is the amino acid sequence of the heavy chain variable domain of MPV201.

SEQ ID NO: 12 is the amino acid sequence of the light chain variable domain of MPV201.

SEQ ID NO: 13 is a nucleic acid sequence encoding the heavy chain variable domain of MPV201.

SEQ ID NO: 14 is a nucleic acid sequence encoding the light chain variable domain of MPV201.

SEQ ID NOs: 15, 16, and 17 are the HCDR1, HCDR2 and HCDR3, respectively, of MPV201.

SEQ ID NOs: 18, 19, and 20 are the LCDR1, LCDR2 and LCDR3, respectively, of MPV201.

SEQ ID NO: 21 is the amino acid sequence of the heavy chain variable domain of MPV314.

SEQ ID NO: 22 is the amino acid sequence of the light chain variable domain of MPV314.

SEQ ID NO: 23 is a nucleic acid sequence encoding the heavy chain variable domain of MPV314.

SEQ ID NO: 24 is a nucleic acid sequence encoding the light chain variable domain of MPV314.

SEQ ID NOs: 25, 26, and 27 are the IMGT HCDR1, HCDR2 and HCDR3, respectively, of MPV314.

SEQ ID NOs: 28, 29, and 30 are the IMGT LCDR1, LCDR2 and LCDR3, respectively of MPV314.

SEQ ID NO: 31 is the amino acid sequence of the heavy chain variable domain of MPV364.

SEQ ID NO: 32 is the amino acid sequence of the light chain variable domain of MPV364.

SEQ ID NO: 33 is a nucleic acid sequence encoding the heavy chain variable domain of MPV364.

SEQ ID NO: 34 is a nucleic acid sequence encoding the light chain variable domain of MPV364.

SEQ ID NOs: 35, 36, and 37 are the IMGT HCDR1, HCDR2 and HCDR3, respectively, of MPV364.

SEQ ID NOs: 38, 39, and 40 are the IMGT LCDR1, LCDR2 and LCDR3, respectively, of MPV364.

SEQ ID NOs: 41 and 42 are the amino acid sequences of the V$_H$ and V$_L$ of the DS7 antibody.

SEQ ID NOs: 43 and 44 are the amino acid sequences of the V$_H$ and V$_L$ of the MPE8 antibody.

SEQ ID NO: 45 is the amino acid sequence of site IV of MPV F protein.

SEQ ID NO: 46 is the amino acid sequence of site IV of RSV F protein.

SEQ ID NO: 47 and 48 are partial heavy chain sequences.

SEQ ID NO: 49 is the amino acid sequence of the heavy chain variable domain of MPV458.

SEQ ID NO: 50 is the amino acid sequence of the light chain variable domain of MPV458.

SEQ ID NO: 51 is a nucleic acid sequence encoding the heavy chain variable domain of MPV458.

SEQ ID NO: 52 is a nucleic acid sequence encoding the light chain variable domain of MPV458.

SEQ ID NOs: 53, 54, and 55 are the IMGT HCDR1, HCDR2 and HCDR3, respectively, of MPV458.

SEQ ID NOs: 56, 57, and 58 are the IMGT LCDR1, LCDR2 and LCDR3, respectively of MPV458.

SEQ ID NO: 59 is the amino acid sequence of the heavy chain variable domain of MPV465.

SEQ ID NO: 60 is the amino acid sequence of the light chain variable domain of MPV465.

SEQ ID NO: 61 is a nucleic acid sequence encoding the heavy chain variable domain of MPV465.

SEQ ID NO: 62 is a nucleic acid sequence encoding the light chain variable domain of MPV465.

SEQ ID NOs: 63, 64, and 65 are the IMGT HCDR1, HCDR2 and HCDR3, respectively, of MPV465.

SEQ ID NOs: 66, 67, and 68 are the IMGT LCDR1, LCDR2 and LCDR3, respectively, of MPV465.

SEQ ID NOs: 69, 70, and 71 are cleavage sites.

SEQ ID NO: 72 is the amino acid sequence of the 66-87 epitope.

DETAILED DESCRIPTION OF SEVERAL EMBODIMENTS

Recent progress in understanding the human immune response to respiratory syncytial virus has paved the way for new vaccine antigens and therapeutics to prevent and treat disease. Progress toward understanding the immune response to hMPV has lagged behind, although hMPV is a leading cause of lower respiratory tract infection in children. Disclosed are human monoclonal antibodies (mAbs) that specifically bind an hMPV F protein, and methods of using these antibodies to inhibit a hMPV infection or o detect an hMPV infection.

Exemplary monoclonal antibodies are disclosed herein. Three of these antibodies, called MPV196, MPV201, and MPV314 have high affinity for the hMPV F protein. These antibodies do not cross react with the RSV F protein. In some embodiments, these antibodies neutralize both genotypes A and B of hMPV. An additional monoclonal antibody, called MPV364, had the weakest binding affinity of all of the identified antibodies, yet was the most potently neutralizing in vitro. This antibody targeted antigenic site III on the hMPV F protein but was different from previously discovered mAbs because it did not cross-react with the RSV F protein. MPV196, MPV201, and MPV314 bind near the same site as the DS7 antibody, but neutralize both genotype A and genotype B MPV. Two additional antibodies, MPV458 and MPV465 bind to a unique antigenic site on the hMPV F protein. MPV458 is potently neutralizing, and both MPV458 and MPV465 bind to hMPV F proteins from all four hMPV F subgroups, and bind at a newly defined epitope on the hMPV F protein defined by the alpha helix 66-87, which is on the head of the MPV F-protein.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Unless context indicated otherwise, "about" refers to plus or minus 5% of a reference value. For example, "about" 100 refers to 95 to 105.

Administration: The introduction of a composition into a subject by a chosen route. Administration can be local or systemic. For example, if the chosen route is intravenous, the composition (such as a composition including a disclosed antibody or antigen binding fragment) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for inhibiting an hMPV infection in a subject. Agents include proteins, nucleic acid molecules, compounds, small molecules, organic compounds, inorganic compounds, or other molecules of interest. An agent can include a therapeutic agent (such as an anti-retroviral agent), a diagnostic agent or a pharmaceutical agent. In some embodiments, the agent is an antibody that specifically bind hMPV, optionally combined with an anti-viral agent. The skilled artisan will understand that particular agents may be useful to achieve more than one result.

Amino acid substitutions: The replacement of one amino acid in a polypeptide with a different amino acid or with no amino acid (i.e., a deletion). In some examples, an amino acid in a polypeptide is substituted with an amino acid from a homologous polypeptide, for example, and amino acid in a recombinant group A MPV F polypeptide can be substituted with the corresponding amino acid from a group B MPV F polypeptide.

Antibody and Antigen Binding Fragment: An immunoglobulin, antigen-binding fragment, or derivative thereof, that specifically binds and recognizes an analyte (antigen) such as an hMPV F polypeptide. The term "antibody" is used herein in the broadest sense and encompasses various antibody structures, including but not limited to monoclonal antibodies, polyclonal antibodies, multispecific antibodies (e.g., bispecific antibodies), and antigen binding fragments, so long as they exhibit the desired antigen-binding activity.

Non-limiting examples of antibodies include, for example, intact immunoglobulins and variants and fragments thereof that retain binding affinity for the antigen. Examples of antigen binding fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dübel (Eds.), *Antibody Engineering*, Vols. 1-2, $2^{nd}$ ed., Springer-Verlag, 2010).

Antibodies also include genetically engineered forms such as chimeric antibodies (such as humanized murine antibodies) and heteroconjugate antibodies (such as bispecific antibodies).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lamda, alpha, gamma, delta, epsilon and mu constant region genes, as well as the myriad immunoglobulin variable domain genes. There are two types of light chain, lamda (k) and kappa (u). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain). In combination, the heavy and the light chain variable regions specifically bind the antigen.

References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, $5^{th}$ ed., NIH Publication No. 91-3242, Public Health Service, National Institutes of Health, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. (*Sequences of Proteins of Immunological*

*Interest,* 5<sup>th</sup> ed., NIH Publication No. 91-3242, Public Health Service, National Institutes of Health, U.S. Department of Health and Human Services, 1991; "Kabat" numbering scheme), Al-Lazikani et al., ("Standard conformations for the canonical structures of immunoglobulins," *J. Mol. Bio.,* 273(4):927-948, 1997; "Chothia" numbering scheme), and Lefranc et al. ("IMGT unique numbering for immunoglobulin and T cell receptor variable domains and Ig superfamily V-like domains," *Dev. Comp. Immunol.,* 27(1):55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

In some embodiments, a disclosed antibody includes a heterologous constant domain. For example, the antibody includes a constant domain that is different from a native constant domain, such as a constant domain including one or more modifications (such as the "LS" mutations) to increase half-life.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Greenfield (Ed.), *Antibodies: A Laboratory Manual,* 2<sup>nd</sup> ed. New York: Cold Spring Harbor Laboratory Press, 2014.)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manual.* 1<sup>st</sup> Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

Antibody or antigen binding fragment that neutralizes MPV: An antibody or antigen binding fragment that specifically binds to an hMPV antigen, such as hMPV (for example, an F protein) in such a way as to inhibit a biological function associated with that inhibits the hMPV infection. The antibody can neutralize the activity of hMPV at various points during the lifecycle of the pathogen.

Biological sample: A sample obtained from a subject. Biological samples include all clinical samples useful for detection of disease or infection (for example, an hMPV infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a hMPV infection.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains but does not necessarily include a constant domain.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual,* 2<sup>nd</sup> ed. Cold Spring Harbor Publications, New York (2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Conjugate: A complex of two molecules linked together, for example, linked together by a covalent bond. In one embodiment, an antibody is linked to an effector molecule; for example, an antibody that specifically binds to an hMPV F protein covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, a MPV-specific antibody can include up to 1, 2, 3, 4, 5, 6, 7, 8, 9, or up to 10 conservative substitutions compared to a reference antibody sequence and retain specific binding activity for MPV, and/or MPV neutralization activity. The term conservative variation also includes the use of a substituted amino acid in place of an unsubstituted parent amino acid.

Individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the hMPV specific antibody, such as the ability to specifically bind to hMPV F protein or neutralize hMPV. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

Control: A reference standard. In some embodiments, the control is a negative control sample obtained from a healthy patient. In other embodiments, the control is a positive control sample obtained from a patient diagnosed with MPV infection. In still other embodiments, the control is a historical control or standard reference value or range of values (such as a previously tested control sample, such as a group of MPV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide (such as a recombinant MPV F protein or immunogenic fragment thereof) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning. A Laboratory Manual*, $4^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something.

DS7 Antibody: A neutralizing monoclonal antibody that specifically binds to an epitope on hMPV F protein that is present on the pre- and post-fusion conformations of the hMPV F protein. The DS7 antibody does not specifically bind to hMPV F in its postfusion conformation. The DS7 antibody and methods for its production are described, for example, in Wen et al., *Nat. Struct. Mol. Biol.*, 19, 461-463, 2012, which is incorporated by reference herein in its entirety. The amino acid sequences of the heavy and light variable regions of the DS7 antibody are provided as SEQ ID NOs: 41 and 42, and have been deposited in PDB as Nos. 4DAG_H (DS7 $V_H$) and 4DAG_L (DS7 $V_L$), each of which is incorporated by reference herein as present in the database on Nov. 10, 2014).

DS7 V$_H$-

(SEQ ID NO: 41)

EVQLLESGGGLVQPGGSRRLSCAASGFTVSSSYMSWVRQTPGKGLEWIS
VFYSGGTTYYADAVKGRFSISMDTSKNTLHLQMNSLRVEDTAIYYCARV
LSRASGMPDAFDIWGPGTMVTVSS

DS7 V$_L$-

(SEQ ID NO: 42)

ELALIQPASVSVSPGQTASITCSGDKLGDKYASWYQQKPGQSPVLVIYQ
DSERPSGIPERFSGSNSGNTATLTISGTQAMDEADYYCQAWDSSTAVFG
GGTTLTVLGQ

Effective amount: A quantity of a specific substance sufficient to achieve a desired effect in a subject to whom the substance is administered. For instance, this can be the amount of an antibody necessary to inhibit an hMPV infection, or to measurably alter outward symptoms of the hMPV infection.

In some embodiments, administration of an effective amount of a disclosed antibody or antigen binding fragment that binds to an hMPV F protein can reduce or inhibit an MPV infection (for example, as measured by infection of cells, or by number or percentage of subjects infected by the hMPV, or by an increase in the survival time of infected subjects, or reduction in symptoms associated with the hMPV) by a desired amount, for example by at least 10%, at least 20%, at least 50%, at least 60%, at least 70%, at least 80%, at least 90%, at least 95%, at least 98%, or even at least 100% (elimination or prevention of detectable hMPV infection), as compared to a suitable control.

The effective amount of an antibody or antigen binding fragment that specifically binds to the hMPV F protein that is administered to a subject to inhibit an hMPV infection will vary depending upon a number of factors associated with that subject, for example the overall health and/or weight of the subject. An effective amount can be determined by varying the dosage and measuring the resulting response, such as, for example, a reduction in pathogen titer. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on hMPV F protein.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lamda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc region: The constant region of an antibody excluding the first heavy chain constant domain. Fc region generally refers to the last two heavy chain constant domains of IgA, IgD, and IgG, and the last three heavy chain constant domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region is typically understood to include immunoglobulin domains C$\gamma$2 and C$\gamma$3 and optionally the lower part of the hinge between C$\gamma$1 and C$\gamma$2. Although the boundaries of the Fc region may vary, the human IgG heavy chain Fc region is usually defined to include residues following C226 or P230 to the Fc carboxyl-terminus, wherein the numbering is according to Kabat. For IgA, the Fc region includes immunoglobulin domains C$\alpha$2 and C3 and optionally the lower part of the hinge between C$\alpha$1 and C$\alpha$2.

Heterologous: Originating from a different genetic source. A nucleic acid molecule that is heterologous to a cell originated from a genetic source other than the cell in which it is expressed. In one specific, non-limiting example, a heterologous nucleic acid molecule encoding a protein, such as an scFv, is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgG: A polypeptide belonging to the class or isotype of antibodies that are substantially encoded by a recognized immunoglobulin gamma gene. In humans, this class comprises IgG$_1$, IgG$_2$, IgG$_3$, and IgG$_4$.

Immune complex: The binding of antibody or antigen binding fragment (such as a scFv) to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance that can stimulate the production of antibodies or a T cell response in an animal, including compositions that are injected or absorbed into an animal, such as hMPV. An immunogen reacts with the products of specific humoral or cellular immunity.

Inhibiting a disease or condition: Reducing the full development of a disease or condition in a subject, for example, reducing the full development of an MPV infection, such as a hMVP infection, in a subject who is at risk of an MPV infection. This includes neutralizing, antagonizing, prohibiting, restraining, slowing, disrupting, stopping, or reversing progression or severity of the disease or condition.

Inhibiting a disease or condition can refer to a prophylactic intervention administered before the disease or condition has begun to develop (for example a treatment initiated in a subject at risk of an hMPV infection, but not infected by hMPV) that reduces subsequent development of the disease or condition and/or ameliorates a sign or symptom of the disease or condition following development. The term "ameliorating," with reference to inhibiting a disease or condition refers to any observable beneficial effect of the prophylactic intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters that are specific to the particular disease or condition.

In some embodiments, the disclosed hMPV F protein-specific antibodies and antigen binding fragments inhibit the growth of the hMPV in a subject, for example, the antibodies and antigen binding fragments inhibit the multiplication of hMPV in the subject, resulting in a reduction in pathogen load in the subject compared to a relevant control. For example, the disclosed hMPV F protein-specific antibodies and antigen binding fragments can inhibit the hMPV infection in a subject, or inhibit viral replication, by at least 20%, at least 30%, at least 40%, or at least 50%, compared to a suitable control.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Kabat position: A position of a residue in an amino acid sequence that follows the numbering convention delineated by Kabat et al. (*Sequences of Proteins of Immunological Interest*, 5$^{th}$ Edition, Department of Health and Human Services, Public Health Service, National Institutes of Health, Bethesda, NIH Publication No. 91-3242, 1991).

Linker: A bi-functional molecule that can be used to link two molecules into one contiguous molecule, for example, to link an effector molecule to an antibody, or a detectable marker to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. The linkage can be either by chemical or recombinant means. "Chemical means" refers to a reaction between the antibody moiety and the effector molecule such that there is a covalent bond formed between the two molecules to form one molecule.

Metapneumovirus (MPV): An enveloped non-segmented negative-sense single-stranded RNA virus of the family Paramyxoviridae. It is a common cause of lower respiratory track infections, including bronchiolitis and pneumonia, among children and adults and infects nearly all humans by five years of age. MPV causes repeated infections including severe lower respiratory tract disease, which may occur at any age, especially among the elderly or those with compromised cardiac, pulmonary, or immune systems. A hMPV can infect humans.

The MPV genome includes eight genes encoding nine proteins, including the glycoproteins SH, G and F. The F protein mediates fusion, allowing entry of the virus into the cell cytoplasm. Two groups of human MPV strains have been described, the A and B groups, which are further divided into subgroups A1, A2, B1, and B2. Exemplary MPV strain sequences are known to the person of ordinary skill in the art. Further, several models of human MPV infection are available, including model organisms infected with hMPV (see, e.g., Herfst et al., J General Virol., 88, 2702-2709, 2007; Bayon et al., Rev. Med. Virol., 2, 15-34, 2013; and Liu et al., Clinical Vaccine Immunol., 20, 1246-1254, 2013). The F protein has a head and a tail; the head is the top 50% of the pre-fusion state, and the tail is the bottom 50% of the pre-fusion state.

Methods of diagnosing MPV infection are known, including use of Direct Fluorescent Antibody detection (DFA), Chromatographic rapid antigen detection, and detection of viral RNA using RT PCR. Quantification of viral load can be determined, for example, by Plaque Assay, antigen capture enzyme immunoassay (EIA), or PCR. Quantification of antibody levels can be performed by subgroup-specific neutralization assay or ELISA. Current MPV treatment includes use of the anti-viral Ribaviran and passive administration of experimental monoclonal antibodies such as MPE8 (see, e.g., Corti et al., *Nature,* 501, 439-443, 2013) and mAb338 (Medimmune, Inc., see Hamelin et al., *Antiviral Res.,* 88, 31-37, 2010), which recognize the MPV F protein and reduces incidence of MPV infection and disease in animal models.

There are several subgroups of MPV, including groups A and B, and subgroups A1, A2, B1, and B2 in human MPV. Within the subgroups of MPV, there are individual strains of each subgroup. Sequences of F proteins from particular MPV strains are known and provided herein (see, e.g., Table 1).

MPV Fusion (F) protein: An MPV envelope glycoprotein that facilitates fusion of viral and cellular membranes. In nature, the MPV F protein is initially synthesized as a single polypeptide precursor approximately 540 amino acids in length, designated $F_0$. $F_0$ includes an N-terminal signal peptide that directs localization to the endoplasmic reticulum, where the signal peptide (approximately the first 18 residues of $F_0$) is proteolytically cleaved. The remaining $F_0$ residues oligomerize to form a trimer which is again processed at a protease site (between approximately $F_0$ positions 102 and 103; for example, $RQSR_{102}$ (residues 99-102) to generate two disulfide-linked fragments, $F_1$ and $F_2$. The smaller of these fragments, $F_2$, originates from the N-terminal portion of the $F_0$ precursor and includes approximately residues 20-102 of $F_0$. The larger of these fragments, $F_1$, includes the C-terminal portion of the $F_0$ precursor (approximately residues 103-540) including an extracellular/lumenal region (~residues 103-490), a transmembrane domain (~residues 491-513), and a cytoplasmic domain (~residues 514-540) at the C-terminus.

Three $F_2$-$F_1$ protomers oligomerize in the mature F protein, which adopts a metastable "prefusion" conformation that is triggered to undergo a conformational change (to a "postfusion" conformation) upon contact with a target cell membrane. This conformational change exposes a hydrophobic sequence, known as the fusion peptide, which is located at the N-terminus of the $F_1$ polypeptide, and which associates with the host cell membrane and promotes fusion of the membrane of the virus, or an infected cell, with the target cell membrane.

The extracellular portion of the MPV F protein is the MPV F ectodomain, which includes the $F_2$ protein (approximately MPV F positions 20-102) and the $F_1$ ectodomain (approximately MPV F positions 103-490). An MPV F ectodomain trimer includes a protein complex of three MPV F ectodomains.

FIG. 4 shows the antigenic sites of F, protein, which are based on competition-binding with the control mAbs MPE8 and 25P13 (site III), DS7, and 101F (site IV). An antibody that binds Site III completes with antibody MPE8 for binding to the MPV F protein.

MPV F prefusion conformation: A structural conformation adopted by the MPV F protein prior to triggering of the fusogenic event that leads to transition of MPV F to the postfusion conformation and following processing into a mature MPV F protein in the secretory system. The prefusion conformation of MPV F is similar in overall structure to the prefusion conformation of the F protein of other paramyxoviruses (such as RSV.

MPE8 Antibody: A neutralizing monoclonal antibody that specifically binds to an epitope on MPV F protein that is present on the prefusion, but not the postfusion conformation, of the MPV F protein. The MPE8 antibody and methods for its production are described, for example, in Corti et al. (Nature, 501, 439-443, 2013), which is incorporated by reference herein. MPE8 binds to site III of MPV F protein; site III can be identified by MPE8 binding. The amino acid sequences of the heavy and light variable regions of the MPE8 antibody used herein are provided as SEQ ID NOs: 43 and 44 MPE8 heavy and light chain sequences have been deposited in GenBank as Nos. AGU13651.1 (MPE8 $V_H$) and AGU13652.1 (MPE8 $V_L$), each of which is incorporated by reference herein as present in the database on Nov. 10, 2014).

```
MPE8 VH-
                             (SEQ ID NO: 43)
EVQLVESGGGLVKPGGSLRLSCAASGFTFSSYSMNWVRQAPGKGLEWVS
SISASSSYSDYADSAKGRFTISRDNAKTSLFLQMNSLRAEDTAIYFCAR
ARATGYSSITPYFDIWGQGTLVTVSS

MPE8 VL-
                             (SEQ ID NO: 44)
QSVVTOPPSVSGAPGORVTISCTGSSSNIGAGYDVHWYOOLPGTAPKLL
IYDNNNRPSGVPDRFSASKSGTSASLAITGLQAEDEADYYCQSYDRSLS
GVFGTGTKVTVL
```

Neutralizing antibody: An antibody which reduces the infectious titer of an infectious agent by binding to a specific antigen on the infectious agent. In some examples the infectious agent is a virus. In some examples, an antibody that is specific for MPV F neutralizes the infectious titer of hMPV. A "broadly neutralizing antibody" is an antibody that binds to and inhibits the function of related antigens, such as antigens that share at least 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen. For example, with regard to MPV, the antibody can bind to and inhibit the function of an antigen, such as MPV F from more than one group.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T." "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first sequence is an "antisense" with respect to a second sequence if a polynucleotide whose sequence is the first sequence specifically hybridizes with a polynucleotide whose sequence is the second sequence.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed antibodies and antigen binding fragments thereof.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Polypeptide modifications: Polypeptides and peptides, such as the antibodies disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Respiratory Syncytial Virus (RSV): An enveloped non-segmented negative-sense single-stranded RNA virus of the family Paramyxoviridae. It is the most common cause of bronchiolitis and pneumonia among children in their first year of life and infects nearly all children by 3 years of age. RSV also causes repeated infections including severe lower respiratory tract disease, which may occur at any age, especially among the elderly or those with compromised cardiac, pulmonary, or immune systems. In the United States, RSV bronchiolitis is the leading cause of hospitalization in infants and a major cause of asthma and wheezing throughout childhood (Shay et al., *JAMA*, 282, 1440 (1999); Hall et al., *N. Engl. J. Med.*, 360, 588 (2009)). Globally, RSV is responsible for 66,000-199,000 deaths each year for children younger than five years of age (Nair et al., *Lancet*, 375, 1545 (2010)), and accounts for 6.7% of deaths among infants one month to one year old-more than any other single pathogen except malaria (Lozano et al., *Lancet*, 380, 2095 (2013)).

The RSV genome is ~15,000 nucleotides in length and includes 10 genes encoding 11 proteins, including the glycoproteins SH, G and F. The F protein mediates fusion, allowing entry of the virus into the cell cytoplasm and also promoting the formation of syncytia. Two subtypes of human RSV strains have been described, the A and B subtypes, based on differences in the antigenicity of the G glycoprotein. RSV strains for other species are also known, including bovine RSV. Exemplary RSV strain sequences are known to the person of ordinary skill in the art. Further, several models of human RSV infection are available, including model organisms infected with hRSV, as well as model organisms infected with species specific RSV, such as use of bRSV infection in cattle (see, e.g., Bern et al., *Am J, Physiol. Lung Cell Mol. Physiol.*, 301: L 148-L 156, 2011).

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence ($1166\div1554*100=75.0$). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Natl. Acad. Sci.* USA 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, 4th ed, Cold Spring Harbor, New York, 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 80% identity" refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence. As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Specifically bind: When referring to an antibody or antigen binding fragment, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a pathogen, for example MPV F protein) and does not bind in a significant amount to other proteins present in the sample or subject. Specific binding can be determined by standard methods. See Harlow & Lane, *Antibodies, A Laboratory Manual*, 2nd ed., Cold Spring Harbor Publications, New York (2013), for a description of immunoassay formats and conditions that can be used to determine specific immunoreactivity.

With reference to an antibody-antigen complex, specific binding of the antigen and antibody has a $K_D$ of less than about $10^7$ Molar, such as less than about $10^{-8}$ Molar, $10^{-9}$, or even less than about $10^{-10}$ Molar. $K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

An antibody that specifically binds to an epitope on hMPV F protein is an antibody that binds substantially to hMPV F protein, including cells or tissue expressing the hMPV F protein, substrate to which the hMPV F protein is attached, or hMPV F protein in a biological specimen. It is, of course, recognized that a certain degree of non-specific interaction may occur between an antibody and a non-target (such as a cell that does not express hMPV F protein). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein.

Subject: Living multi-cellular vertebrate organisms, a category that includes human and non-human mammals. In an example, a subject is a human. In a particular example, the subject is a newborn infant. In an additional example, a subject is selected that is in need of inhibiting of an hMPV infection. For example, the subject is either uninfected and at risk of hMPV infection or is infected in need of treatment.

Therapeutically effective amount: The amount of agent, such as a disclosed antibodies or antigen binding fragments thereof that is sufficient to prevent, treat (including prophy-laxis), reduce and/or ameliorate the symptoms and/or under-lying causes of a disorder or disease, for example to prevent, inhibit, and/or treat an hMPV infection. In some embodi-ments, a therapeutically effective amount is sufficient to reduce or eliminate a symptom of a disease, such as an hMPV infection. For instance, this can be the amount necessary to inhibit or prevent viral replication or to mea-surably alter outward symptoms of the viral infection. In general, this amount will be sufficient to measurably inhibit virus replication or infectivity.

In one example, a desired response is to inhibit or reduce or prevent an hMPV infection. The MPV infection does not need to be completely eliminated or reduced or prevented for the method to be effective. For example, administration of a therapeutically effective amount of the agent can decrease the hMPV infection (for example, as measured by infection of cells, or by number or percentage of subjects infected by hMPV) by a desired amount, for example by at least 10%, at least 20%, at least 50%, at least 60%, at least 70%, at least 80%, at least 90%, at least 95%, at least 98%, or even at least 100% (elimination or prevention of detect-able hMPV infection, as compared to a suitable control.

A therapeutically effective amount of an agent can be administered in a single dose, or in several doses, for example daily, during a course of treatment (such as a prime-boost vaccination treatment). However, the therapeu-tically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile com-ponents.

Treating or preventing a disease: Inhibiting the full devel-opment of a disease or condition, for example, in a subject who is at risk of or has a disease such as an hMPV infection. "Treatment" refers to a therapeutic intervention that ame-liorates a sign or symptom of a disease or pathological condition after it has begun to develop. The term "amelio-rating," with reference to a disease or pathological condi-tion, refers to any observable beneficial effect of the treat-ment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

The term "reduces" is a relative term, such that an agent reduces a disease or condition if the disease or condition is quantitatively diminished following administration of the agent, or if it is diminished following administration of the agent, as compared to a reference agent. Similarly, the term "prevents" does not necessarily mean that an agent com-pletely eliminates the disease or condition, so long as at least one characteristic of the disease or condition is eliminated. Thus, a composition that reduces or prevents an infection, can, but does not necessarily completely, eliminate such an infection, so long as the infection is measurably diminished, for example, by at least about 50%, such as by at least about 70%, or about 80%, or even by about 90% the infection in the absence of the agent, or in comparison to a reference agent.

Transformed: A transformed cell is a cell into which a nucleic acid molecule has been introduced by molecular biology techniques. As used herein, the term transformed and the like (e.g., transformation, transfection, transduction, etc.) encompasses all techniques by which a nucleic acid molecule might be introduced into such a cell, including transduction with viral vectors, transformation with plasmid vectors, and introduction of DNA by electroporation, lipo-fection, and particle gun acceleration.

Vector: An entity containing a nucleic acid molecule (such as a DNA or RNA molecule) bearing a promoter(s) that is operationally linked to the coding sequence of a protein of interest and can express the coding sequence. Non-limiting examples include a naked or packaged (lipid and/or protein) DNA, a naked or packaged RNA, a subcomponent of a virus or bacterium or other microorganism that may be replica-tion-incompetent, or a virus or bacterium or other microor-ganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses. In some embodiments, a viral vector comprises a nucleic acid molecule encoding a dis-closed antibody or antigen binding fragment that specifically binds to hMPV F protein and neutralizes the hMPV.

Under conditions sufficient for: A phrase that is used to describe any environment that permits a desired activity.

II. Description of Several Embodiments

Isolated monoclonal antibodies and antigen binding frag-ments that specifically bind hMPV F protein are provided. The antibodies and antigen binding fragments can be fully human. The antibodies and antigen binding fragments can neutralize hMPV, example the disclosed antibodies can inhibit an hMPV infection in vivo, and can be administered prior to, or after, an infection with hMPV. Also disclosed herein are compositions comprising the antibodies and anti-gen binding fragments and a pharmaceutically acceptable carrier. Nucleic acids encoding the antibodies or antigen binding fragments, expression vectors (such as adeno-asso-ciated virus (AAV) viral vectors) comprising these nucleic acids are also provided. The antibodies, antigen binding fragments, nucleic acid molecules, host cells, and compo-sitions can be used for research, diagnostic, treatment and prophylactic purposes. For example, the disclosed antibod-ies and antigen binding fragments can be used to diagnose a subject with an hMPV infection or can be administered to inhibit an hMPV infection in a subject.

In some embodiments, the disclosed antibodies do not cross react with the RSV F protein. In other embodiments, these antibodies neutralize both genotypes A and B of hMPV. In further embodiments, the disclosed antibodies bind to site III of MPV F protein. In yet other embodiments, the disclosed antibodies bind to an epitope of n the hMPV F protein that includes alpha helix 66-87.

A. Monoclonal Antibodies that Specifically Bind hMPV F Protein and Antigen Binding Fragments Thereof The discussion of monoclonal antibodies below refers to isolated monoclonal antibodies that include heavy and/or light chain variable domains (or antigen binding fragments thereof) comprising a CDR1, CDR2, and/or CDR3 with reference to the IMGT numbering scheme (unless the context indicates otherwise). Various CDR numbering schemes (such as the Kabat, Chothia or IMGT numbering schemes) can be used to determine CDR positions. The amino acid sequence and the CDRs of the heavy and light chain of the MPV196, MPV201, MPV314, MPV364, MPV458 and MPV465 monoclonal antibody according to the IMGT numbering scheme are provided in the sequences, but are exemplary only.

In some embodiments, the antibody or antigen binding fragment is based on or derived from the MPV196 antibody, and specifically binds to hMPV F protein and neutralizes hMPV. In some examples, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT, Kabat or Chothia), of the MPV196 antibody, and specifically binds to hMPV F protein and neutralizes hMPV. In further embodiments, the antibody or antigen binding fragment is based on or derived from the MPV201 antibody, and specifically binds to hMPV F protein and neutralizes hMPV. In some examples, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT, Kabat or Chothia), of the MPV201 antibody, and specifically binds to hMPV F protein and neutralizes hMPV. In more embodiments, the antibody or antigen binding fragment is based on or derived from the MPV314 antibody, and specifically binds to hMPV F protein and neutralizes hMPV. In some examples, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT, Kabat or Chothia), of the MPV314 antibody, and specifically binds to hMPV F protein and neutralizes hMPV. In yet other embodiments, the antibody or antigen binding fragment is based on or derived from the MPV364 antibody, and specifically binds to and neutralizes hMPV. In some examples, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT, Kabat or Chothia), of the MPV364 antibody, and specifically binds to hMPV F protein and neutralizes hMPV.

In some embodiments, the antibody or antigen binding fragment is based on or derived from the MPV458 antibody, and specifically binds to hMPV F protein and neutralizes hMPV. In some examples, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT, Kabat or Chothia), of the MPV458 antibody, and specifically binds to hMPV F protein and neutralizes hMPV. In more embodiments, the antibody or antigen binding fragment is based on or derived from the MPV465 antibody, and specifically binds to hMPV F protein and neutralizes hMPV. In some examples, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT, Kabat or Chothia), of the MPV465 antibody, and specifically binds to hMPV F protein and neutralizes hMPV. In the embodiments, the monoclonal antibody binds an epitope that includes the 66-87 epitope, see, for example, FIG. 9.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 1, and specifically binds to hMPV F protein neutralizes hMPV. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 2, and specifically binds to hMPV F protein and neutralizes hMPV. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 1 and 2, respectively, and specifically binds to hMPV F protein and neutralizes hMPV.

In more embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 11, and specifically binds to hMPV F protein neutralizes hMPV. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 12, and specifically binds to hMPV F protein and neutralizes hMPV. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 11 and 12, respectively, and specifically binds to hMPV F protein and neutralizes hMPV.

In more embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 21, and specifically binds to hMPV F protein neutralizes hMPV. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 22, and specifically binds to hMPV F protein and neutralizes hMPV. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 21 and 22, respectively, and specifically binds to hMPV F protein and neutralizes hMPV.

In further embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 31, and specifically binds to hMPV F protein neutralizes hMPV. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 32, and specifically binds to hMPV F protein and neutralizes hMPV. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 31 and 32, respectively, and specifically binds to hMPV F protein and neutralizes hMPV.

In more embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 49, and specifically binds to hMPV F protein neutralizes hMPV. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 50, and specifically binds to hMPV F protein and neutralizes hMPV. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 49 and 50, respectively, and specifically binds to hMPV F protein and neutralizes hMPV.

In further embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 59, and specifically binds to hMPV F protein neutralizes hMPV. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 60, and specifically binds to hMPV F protein and neutralizes hMPV. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 59 and 60, respectively, and specifically binds to hMPV F protein and neutralizes hMPV.

In some embodiments, the antibody or antigen binding fragment comprises a $V_H$ comprising a HCDR1, a HCDR2, and a HCDR3 as set forth as SEQ ID NOs: 3, 4, and 5, respectively, and a $V_L$ comprising a LCDR1, a LCDR2, and a LCDR3 as set forth as SEQ ID NOs: 6, 7, and 8, respectively, and specifically binds to hMPV F protein and neutralizes hMPV.

In more embodiments, the antibody or antigen binding fragment comprises a $V_H$ comprising a HCDR1, a HCDR2, and a HCDR3 as set forth as SEQ ID NOs: 13, 14, and 15, respectively, and a $V_L$ comprising a LCDR1, a LCDR2, and a LCDR3 as set forth as SEQ ID NOs: 16, 17, and 18, respectively, and specifically binds to hMPV F protein and neutralizes hMPV.

In yet other embodiments, the antibody or antigen binding fragment comprises a $V_H$ comprising a HCDR1, a HCDR2, and a HCDR3 as set forth as SEQ ID NOs: 23, 24, and 25, respectively, and a $V_L$ comprising a LCDR1, a LCDR2, and a LCDR3 as set forth as SEQ ID NOs: 26, 27, and 28, respectively, and specifically binds to hMPV F protein and neutralizes hMPV.

In further embodiments, the antibody or antigen binding fragment comprises a $V_H$ comprising a HCDR1, a HCDR2, and a HCDR3 as set forth as SEQ ID NOs: 33, 34, and 35, respectively, and a $V_L$ comprising a LCDR1, a LCDR2, and a LCDR3 as set forth as SEQ ID NOs: 36, 37, and 38, respectively, and specifically binds to hMPV F protein and neutralizes hMPV.

In more embodiments, the antibody or antigen binding fragment comprises a $V_H$ comprising a HCDR1, a HCDR2, and a HCDR3 as set forth as SEQ ID NOs: 53, 54, and 55, respectively, and a $V_L$ comprising a LCDR1, a LCDR2, and a LCDR3 as set forth as SEQ ID NOs: 56, 57, and 58, respectively, and specifically binds to hMPV F protein and neutralizes hMPV.

In additional embodiments, the antibody or antigen binding fragment comprises a $V_H$ comprising a HCDR1, a HCDR2, and a HCDR3 as set forth as SEQ ID NOs: 63, 64, and 65, respectively, and a $V_L$ comprising a LCDR1, a LCDR2, and a LCDR3 as set forth as SEQ ID NOs: 66, 67, and 68, respectively, and specifically binds to hMPV F protein and neutralizes hMPV.

In some embodiments, the antibody or antigen binding fragment comprises a $V_H$ comprising a HCDR1, a HCDR2, and a HCDR3 as set forth as SEQ ID NOs: 3, 4, and 5, respectively, a $V_L$ comprising a LCDR1, a LCDR2, and a LCDR3 as set forth as SEQ ID NOs: 6, 7, and 8, respectively, wherein the $V_H$ comprises an amino acid sequence at least 90% identical to SEQ ID NO: 1, such as 95%, 96%, 97%, 985 o 995 identical to SEQ ID NO: 1, and wherein the $V_L$ comprises an amino acid sequence at least 90% identical to SEQ ID NO: 2, such as 95%, 96%, 97%, 98% or 99% identical to SEQ ID NO: 2, and the antibody or antigens binding fragment specifically binds to hMPV F protein and neutralizes hMPV.

In more embodiments, the antibody or antigen binding fragment comprises a $V_H$ comprising a HCDR1, a HCDR2, and a HCDR3 as set forth as SEQ ID NOs: 13, 14, and 15, respectively, a $V_L$ comprising a LCDR1, a LCDR2, and a LCDR3 as set forth as SEQ ID NOs: 16, 17, and 18, respectively, wherein the $V_H$ comprises an amino acid sequence at least 90% identical to SEQ ID NO: 11, such as 95%, 96%, 97%, 98% or 99% identical to SEQ ID NO: 11, and wherein the $V_L$ comprises an amino acid sequence at least 90% identical to SEQ ID NO: 12, such as 95%, 96%, 97%, 98% or 99% identical to SEQ ID NO: 12, and the antibody or antigens binding fragment specifically binds to hMPV F protein and neutralizes hMPV.

In yet other embodiments, the antibody or antigen binding fragment comprises a $V_H$ comprising a HCDR1, a HCDR2, and a HCDR3 as set forth as SEQ ID NOs: 23, 24, and 25, respectively, a $V_L$ comprising a LCDR1, a LCDR2, and a LCDR3 as set forth as SEQ ID NOs: 26, 27, and 28, respectively, wherein the $V_H$ comprises an amino acid sequence at least 90% identical to SEQ ID NO: 21, such as 95%, 96%, 97%, 98% or 99% identical to SEQ ID NO: 21, and wherein the $V_L$ comprises an amino acid sequence at least 90% identical to SEQ ID NO: 22, such as 95%, 96%, 97%, 98% or 99% identical to SEQ ID NO: 22, and the antibody or antigens binding fragment specifically binds to hMPV F protein and neutralizes hMPV.

In further embodiments, the antibody or antigen binding fragment comprises a $V_H$ comprising a HCDR1, a HCDR2, and a HCDR3 as set forth as SEQ ID NOs: 33, 34, and 35, respectively, a $V_L$ comprising a LCDR1, a LCDR2, and a LCDR3 as set forth as SEQ ID NOs: 36, 37, and 38, respectively, wherein the $V_H$ comprises an amino acid sequence at least 90% identical to SEQ ID NO: 31, such as 95%, 96%, 97%, 98% or 99% identical to SEQ ID NO: 31, and wherein the $V_L$ comprises an amino acid sequence at least 90% identical to SEQ ID NO: 32, such as 95%, 96%, 97%, 98% or 99% identical to SEQ ID NO: 32, and the antibody or antigens binding fragment specifically binds to hMPV F protein and neutralizes hMPV.

In more embodiments, the antibody or antigen binding fragment comprises a $V_H$ comprising a HCDR1, a HCDR2, and a HCDR3 as set forth as SEQ ID NOs: 53, 54, and 55, respectively, a $V_L$ comprising a LCDR1, a LCDR2, and a LCDR3 as set forth as SEQ ID NOs: 56, 57, and 58, respectively, wherein the $V_H$ comprises an amino acid sequence at least 90% identical to SEQ ID NO: 49, such as 95%, 96%, 97%, 98% or 99% identical to SEQ ID NO: 49, and wherein the $V_L$ comprises an amino acid sequence at least 90% identical to SEQ ID NO: 50, such as 95%, 96%, 97%, 98% or 99% identical to SEQ ID NO: 50, and the antibody or antigens binding fragment specifically binds to hMPV F protein and neutralizes hMPV.

In additional embodiments, the antibody or antigen binding fragment comprises a $V_H$ comprising a HCDR1, a HCDR2, and a HCDR3 as set forth as SEQ ID NOs: 63, 64, and 65, respectively, a $V_L$ comprising a LCDR1, a LCDR2, and a LCDR3 as set forth as SEQ ID NOs: 66, 67, and 68, respectively, wherein the $V_H$ comprises an amino acid sequence at least 90% identical to SEQ ID NO: 59, such as 95%, 96%, 97%, 98% or 99% identical to SEQ ID NO: 59, and wherein the $V_L$ comprises an amino acid sequence at least 90% identical to SEQ ID NO: 60, such as 95%, 96%, 97%, 98% or 99% identical to SEQ ID NO: 60, and the antibody or antigens binding fragment specifically binds to hMPV F protein and neutralizes hMPV.

In some embodiments, the antibody or antigen binding fragment comprises a $V_H$ comprising the amino acid sequence set forth as SEQ ID NO: 1, and specifically binds to hMPV F protein and neutralizes hMPV. In more embodiments, the antibody or antigen binding fragment comprises a $V_L$ comprising the amino acid sequence set forth as SEQ ID NO: 2, and specifically binds to hMPV F protein and neutralizes hMPV. In some embodiments, the antibody or antigen binding fragment comprises a $V_H$ and a $V_L$ comprising the amino acid sequences set forth as SEQ ID NOs: 1 and 2, respectively, and specifically binds to hMPV F protein and neutralizes hMPV.

In more embodiments, the antibody or antigen binding fragment comprises a $V_H$ comprising the amino acid sequence set forth as SEQ ID NO: 11, and specifically binds to hMPV F protein and neutralizes hMPV. In more embodiments, the antibody or antigen binding fragment comprises a $V_L$ comprising the amino acid sequence set forth as SEQ ID NO: 12, and specifically binds to hMPV F protein and neutralizes hMPV. In some embodiments, the antibody or antigen binding fragment comprises a $V_H$ and a $V_L$ comprising the amino acid sequences set forth as SEQ ID NOs: 11 and 12, respectively, and specifically binds to hMPV F protein and neutralizes hMPV.

In yet other embodiments, the antibody or antigen binding fragment comprises a $V_H$ comprising the amino acid sequence set forth as SEQ ID NO: 21, and specifically binds to hMPV F protein and neutralizes hMPV. In more embodiments, the antibody or antigen binding fragment comprises a $V_L$ comprising the amino acid sequence set forth as SEQ ID NO: 22, and specifically binds to hMPV F protein and neutralizes hMPV. In some embodiments, the antibody or antigen binding fragment comprises a $V_H$ and a $V_L$ comprising the amino acid sequences set forth as SEQ ID NOs: 21 and 22, respectively, and specifically binds to hMPV F protein and neutralizes hMPV.

In further embodiments, the antibody or antigen binding fragment comprises a $V_H$ comprising the amino acid sequence set forth as SEQ ID NO: 31, and specifically binds to hMPV F protein and neutralizes hMPV. In more embodiments, the antibody or antigen binding fragment comprises a $V_L$ comprising the amino acid sequence set forth as SEQ ID NO: 32, and specifically binds to hMPV F protein and neutralizes hMPV. In some embodiments, the antibody or antigen binding fragment comprises a $V_H$ and a $V_L$ comprising the amino acid sequences set forth as SEQ ID NOs: 31 and 32, respectively, and specifically binds to hMPV F protein and neutralizes hMPV.

In more embodiments, the antibody or antigen binding fragment comprises a $V_H$ comprising the amino acid sequence set forth as SEQ ID NO: 49, and specifically binds to hMPV F protein and neutralizes hMPV. In more embodiments, the antibody or antigen binding fragment comprises a $V_L$ comprising the amino acid sequence set forth as SEQ ID NO: 50, and specifically binds to hMPV F protein and neutralizes hMPV. In some embodiments, the antibody or antigen binding fragment comprises a $V_H$ and a $V_L$ comprising the amino acid sequences set forth as SEQ ID NOs: 49 and 50, respectively, and specifically binds to hMPV F protein and neutralizes hMPV.

In additional embodiments, the antibody or antigen binding fragment comprises a $V_H$ comprising the amino acid sequence set forth as SEQ ID NO: 59, and specifically binds to hMPV F protein and neutralizes hMPV. In more embodiments, the antibody or antigen binding fragment comprises a $V_L$ comprising the amino acid sequence set forth as SEQ ID NO: 60, and specifically binds to hMPV F protein and neutralizes hMPV. In some embodiments, the antibody or antigen binding fragment comprises a $V_H$ and a $V_L$ comprising the amino acid sequences set forth as SEQ ID NOs: 59 and 60, respectively, and specifically binds to hMPV F protein and neutralizes hMPV.

In some embodiments, the disclosed antibodies inhibit viral replication.

1. Additional Antibodies that Bind to the MPV364 Epitope on MPV F Protein

It is disclosed herein that MPV364 targets antigenic site III on the hMPV F protein and competes for binding with previously discovered mAbs MPE8 and 25P13. However, MPE8 and 25P13 both cross-react with the respiratory syncytial virus (RSV) F protein (see Wen et al., Nat. Microbiol. 2: 1672 (2017)). MPV364 does not cross-react with the RSV F protein. The binding pose of MPV364 is thus shifted. Accordingly, in some embodiments, an antibody or antigen binding fragment is provided that specifically binds to an epitope on hMPV F protein that is bound by MPV364, wherein the antibodies do not cross-react with the RSV F protein.

Furthermore, it is disclosed herein that MPV458 and MPV465 target an epitope that includes the 66-87 helix of hMPV F. The 66-87 helix of hMPV F is structurally conserved in the pre-fusion and post-fusion conformations, although the helix is exposed on the outer surface in the trimeric post-fusion conformation. This sequence identity of the helix is highly conserved, as residues are identical between the A1 and B2 subgroups, except for a Lys82/Arg82 mutation.

In some examples, antibodies that bind to an epitope of interest can be identified based on their ability to cross-compete (for example, to competitively inhibit the binding of, in a statistically significant manner) with the MPV364 antibody provided herein in binding assays. In other examples, antibodies that bind to an epitope of interest can be identified based on their ability to cross-compete (for example, to competitively inhibit the binding of, in a statistically significant manner) with the MPV458 or MPV465 antibody provided herein in binding assays.

Human antibodies that bind to the same epitope on hMPV F protein to which the MPV364 antibody binds, or to the epitope to which the MPV458/MPV465 antibodies bind, can be produced using any suitable method. Such antibodies may be prepared, for example, by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies that bind to the same epitope on hMPV F protein to which the MPV364 antibody binds, or to which the MPV458/MPV465 antibodies bind, can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4): 265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005). Human antibodies may also be generated by isolating Fv clone variable domain sequences selected from human-derived phage display libraries. Such variable domain sequences may then be combined with a desired human constant domain.

Antibodies and antigen binding fragments that specifically bind to the same epitope on hMPV F protein to which the MPV364 antibody binds, or that bind to the same epitope on hMPV F protein to which the MPV458/MPV465 antibodies bind, can also be isolated by screening combinatorial libraries for antibodies with the desired binding characteristics. For example, by generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101(34): 12467-12472 (2004); and Lee et al., *J. Immunol. Methods* 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

2. Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region from another source, or an optimized framework region. Alternatively, a heterologous framework region, such as, but not limited to a mouse or monkey framework region, can be included in the heavy or light chain of the antibodies.

The antibody can be of any isotype. The antibody can be, for example, an IgM or an IgG antibody, such as $IgG_1$, $IgG_2$, $IgG_3$, or $IgG_4$. The class of an antibody that specifically binds hMPV can be switched with another. In one aspect, a nucleic acid molecule encoding $V_L$ or $V_H$ is isolated such that it does not include any nucleic acid sequences encoding the constant region of the light or heavy chain, respectively. A nucleic acid molecule encoding $V_L$ or $V_H$ is then operatively linked to a nucleic acid sequence encoding a CL or CH from a different class of immunoglobulin molecule. This can be achieved, for example, using a vector or nucleic acid molecule that comprises a $C_L$ or $C_H$ chain. For example, an antibody that specifically binds PfCSP, that was originally IgG may be class switched to an IgM. Class switching can be used to convert one IgG subclass to another, such as from $IgG_1$ to $IgG_2$. $IgG_3$, or $IgG_4$.

In some examples, the disclosed antibodies are oligomers of antibodies, such as dimers, trimers, tetramers, pentamers, hexamers, septamers, octomers and so on.

The antibody or antigen binding fragment can be derivatized or linked to another molecule (such as another peptide or protein). In general, the antibody or antigen binding fragment is derivatized such that the binding to hMPV is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

(a) Binding Affinity

In several embodiments, the antibody or antigen binding fragment specifically binds hMPV F protein with an affinity (e.g., measured by $K_D$) of no more than $1.0 \times 10^{-8}$ M, no more than $5.0 \times 10^{-8}$ M, no more than $1.0 \times 10^{-9}$ M, no more than $5.0 \times 10^{-9}$ M, no more than $1.0 \times 10^{-10}$ M, no more than $5.0 \times 10^{-10}$ M, or no more than $1.0 \times 10^{-11}$ M. $K_D$ can be measured, for example, by a radiolabeled antigen binding assay (RIA) performed with the Fab version of an antibody of interest and its antigen. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293(4):865-881, 1999). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (NUNC™ Catalog #269620), 100 μM or 26 pM [$^{125}$I]-antigen are mixed with serial dilutions of a Fab of interest (e.g., consistent with assessment of the anti-VEGF antibody, Fab-12, in Presta et al., Cancer Res. 57(20):4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT™-20; PerkinEmler) is added, and the plates are counted on a TOPCOUNT™ gamma counter (PerkinEmler) for ten minutes. Concentrations of each Fab that give less than or equal to 20% of maximal binding are chosen for use in competitive binding assays.

In another assay, $K_D$ can be measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE®, Inc.) are activated with N-ethyl- N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 l/minute to achieve approximately 10 response units (RU) of coupled protein. Following the injection of antigen, 1 M ethanolamine is injected to block unreacted groups. For kinetics measurements, twofold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(b) Multispecific Antibodies

In some embodiments, a multi-specific antibody, such as a bi-specific antibody, is provided that comprises an antibody or antigen binding fragment that specifically binds hMPV, as provided herein, or an antigen binding fragment thereof. Any suitable method can be used to design and produce the multi-specific antibody, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Non-limiting examples of suitable crosslinkers include those that are heterobifunctional, having two distinctly reactive groups separated by an appropriate spacer (such as m-maleimido-benzoyl-N-hydroxysuccinimide ester) or homobifunctional (such as disuccinimidyl suberate).

The multi-specific antibody may have any suitable format that allows for binding to hMPV F protein by the antibody or antigen binding fragment as provided herein. Bispecific single chain antibodies can be encoded by a single nucleic acid molecule. Non-limiting examples of bispecific single chain antibodies, as well as methods of constructing such antibodies are provided in U.S. Pat. Nos. 8,076,459, 8,017, 748, 8,007,796, 7,919,089, 7,820,166, 7,635,472, 7,575,923, 7,435,549, 7,332,168, 7,323,440, 7,235,641, 7,229,760, 7,112,324, 6,723,538. Additional examples of bispecific single chain antibodies can be found in PCT application No. WO 99/54440; Mack et al., *J. Immunol.,* 158(8):3965-3970, 1997; Mack et al., *Proc. Natl. Acad. Sci. U.S.A.,* 92(15): 7021-7025, 1995; Kufer et al., *Cancer Immunol. Immunother.,* 45(3-4):193-197, 1997; Loffler et al., *Blood,* 95(6): 2098-2103, 2000; and Bruhl et al., *J. Immunol.,* 166(4): 2420-2426, 2001. Production of bispecific Fab-scFv ("bibody") molecules are described, for example, in Schoonjans et al. (*J. Immunol.,* 165(12):7050-7057, 2000) and Willems et al. (J. Chromatogr. *B Analyt. Technol. Biomed Life Sci.* 786(1-2):161-176, 2003). For bibodies, a scFv molecule can be fused to one of the VL-CL (L) or VH-CH1 chains, e.g., to produce a bibody one scFv is fused to the C-term of a Fab chain.

(c) Antigen Binding Fragments

Antigen binding fragments are encompassed by the present disclosure, such as Fab, F(ab')$_2$, and Fv which include a heavy chain and $V_L$ and specifically bind hMPV F protein. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the $V_L$ and $V_L$ expressed as two chains; and (5) Single chain antibody (such as scFv), defined as a genetically engineered molecule containing the $V_H$ and the $V_L$ linked by a suitable polypeptide linker as a genetically fused single chain molecule (see, e.g., Ahmad et al., *Clin. Dev. Immunol.,* 2012, doi:10.1155/2012/980250; Marbry and Snavely, *IDrugs,* 13(8):543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "miniantibody."

Any suitable method of producing the above-discussed antigen binding fragments may be used. Non-limiting examples are provided in Harlow and Lane, *Antibodies: A Laboratory Manual, 2$^{nd}$,* Cold Spring Harbor Laboratory, New York, 2013.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

(d) Variants

In some embodiments, amino acid sequence variants of the antibodies provided herein (such as MPV196, MPV201, MPV314, or MPV364) are provided. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the $V_H$ and the $V_L$ regions, and will retain the charge characteristics of the residues in order to preserve the low pI and low toxicity of the molecules. Amino acid substitutions can be made in the $V_H$ and the $V_L$ regions to increase yield.

In some embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 1. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 2.

In more embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 11. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 12.

In further embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 21. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 22.

In yet other embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 31. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 32.

In more embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 49. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 50.

In more embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 59. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 60.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, or the light chain of the antibody, or the heavy and light chains of the antibody, compared to known framework regions, or compared to the framework regions of the MPV196, MPV201, MPV314, MPV364, MPV458, or MPV465 antibody, and maintain the specific binding activity for hMPV F protein.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant $V_H$ and $V_L$ sequences provided above, each CDR either is unaltered, or contains no more than one, two or three amino acid substitutions.

To increase binding affinity of the antibody, the $V_L$ and $V_H$ segments can be randomly mutated, such as within HCDR3 region or the LCDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the HCDR3 or LCDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for hMPV F protein. In particular examples, the $V_H$ amino acid sequence is one of SEQ ID NOs: 1, 11, 21, 31, 49 or 59. In other examples, the $V_L$ amino acid sequence is one of SEQ ID NOs: 2, 12, 22, 32, 50 or 60.

In some embodiments, an antibody (such as MPV196, MPV201, MPV314, MPV364, MPV458, or MPV465) or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody (such as MPV196, MPV201, MPV314, MPV364, MPV458, or MPV465) comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *Trends Biotechnol.* 15(1):26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about 3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO 2002/031140; Okazaki et al., *J. Mol. Biol.*, 336(5):1239-1249, 2004; Yamane-Ohnuki et al., *Biotechnol. Bioeng.* 87(5):614-622, 2004. Examples of cell lines capable of producing defucosylated antibodies include Lec 13 CHO cells deficient in protein fucosylation (Ripka et al., *Arch. Biochem. Biophys.* 249(2):533-545, 1986; US Pat. Appl. No. US 2003/0157108 and WO 2004/056312, especially at Example 11), and knockout cell lines, such as alpha-1,6-fucosyltransferase gene, FUT8, knockout CHO cells (see, e.g., Yamane-Ohnuki et al., *Biotechnol. Bioeng.*, 87(5): 614-622, 2004; Kanda et al., *Biotechnol. Bioeng.*, 94(4): 680-688, 2006; and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

In several embodiments, the constant region of the antibody (such as MPV196, MPV201, MPV314, or MPV364) comprises one or more amino acid substitutions to optimize in vivo half-life of the antibody. The serum half-life of IgG Abs is regulated by the neonatal Fc receptor (FcRn). Thus, in several embodiments, the antibody comprises an amino acid substitution that increases binding to the FcRn. Non-limiting examples of such substitutions include substitutions at IgG constant regions T250Q and M428L (see, e.g., Hinton et al., *J Immunol.*, 176(1):346-356, 2006); M428L and N434S (the "LS" mutation, see, e.g., Zalevsky, et al., *Nature Biotechnol.*, 28(2):157-159, 2010); N434A (see, e.g., Petkova et al., *Int. Immunol.*, 18(12):1759-1769, 2006); T307A, E380A, and N434A (see, e.g., Petkova et al., *Int. Immunol.*, 18(12):1759-1769, 2006); and M252Y, S254T, and T256E (see, e.g., Dall'Acqua et al., *J. Biol. Chem.*, 281(33):23514-23524, 2006). The disclosed antibodies and antigen binding fragments can be linked to or comprise an Fc polypeptide including any of the substitutions listed above, for example, the Fc polypeptide can include the M428L and N434S substitutions.

In some embodiments, the constant region of the antibody comprises one or more amino acid substitutions to optimize ADCC. ADCC is mediated primarily through a set of closely related Fcγ receptors. In some embodiments, the antibody comprises one or more amino acid substitutions that increase binding to FcγRIIIa. Non-limiting examples of such substitutions include substitutions at IgG constant regions S239D and I332E (see, e.g., Lazar et al., *Proc. Natl., Acad. Sci. U.S.A.*, 103(11):4005-4010, 2006); and S239D, A330L, and I332E (see, e.g., Lazar et al., *Proc. Natl., Acad. Sci. U.S.A.*, 103(11):4005-4010, 2006).

Combinations of the above substitutions are also included, to generate an IgG constant region with increased binding to FcRn and FcγRIIIa. The combinations increase antibody half-life and ADCC. For example, such combinations include antibodies with the following amino acid substitutions in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E. In some examples, the antibodies, or an antigen binding fragment thereof is modified such that it is directly cytotoxic to infected cells, or uses natural defenses such as complement, ADCC, or phagocytosis by macrophages.

In some embodiments, an antibody provided herein may be further modified to contain additional nonproteinaceous moieties. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in an application under defined conditions, etc.

B. Conjugates

The antibodies and antigen binding fragments that specifically bind to hMPV F protein, as disclosed herein, can be conjugated to an agent, such as an effector molecule or detectable marker. Both covalent and noncovalent attachment means may be used. Various effector molecules and detectable markers can be used, including (but not limited to) toxins and radioactive agents such as $^{125}I$, $^{32}P$, $^{14}C$, $^{3}H$ and $^{35}S$ and other labels, target moieties and ligands, etc. The choice of a particular effector molecule or detectable marker depends on the particular target molecule or cell, and the desired biological effect.

The procedure for attaching an effector molecule or detectable marker to an antibody or antigen binding fragment varies according to the chemical structure of the effector. Polypeptides typically contain a variety of functional groups, such as carboxyl (—COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any suitable linker molecule. The linker is capable of forming covalent bonds to both the antibody or antigen binding fragment and to the effector molecule or detectable marker. Suitable linkers include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side chains (such as through a disulfide linkage to cysteine) or the alpha carbon, or through the amino, and/or carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies, a suitable method for attaching a given agent to an antibody or antigen binding fragment or other polypeptide can be determined.

The antibody or antigen binding fragment can be conjugated with a detectable marker; for example, a detectable marker capable of detection by ELISA, spectrophotometry, flow cytometry, microscopy or diagnostic imaging techniques (such as CT, computed axial tomography (CAT), MRI, magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1- napthalenesulfonyl chloride, phycoerythrin, lanthanide phosphors and the like. Bioluminescent markers are also of use, such as luciferase, green fluorescent protein (GFP), and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitope recognized by a secondary reporter (such as leucine zipper pair sequences, binding sites for secondary antibodies, metal binding domains, epitope tags).

The antibody or antigen binding fragment can also be conjugated with a radiolabeled amino acid, for example, for diagnostic purposes. For instance, the radiolabel may be used to detect hMPV by radiography, emission spectra, or other diagnostic techniques. Examples of labels for polypeptides include, but are not limited to, the following radioisotopes: $^{3}$H, $^{14}$C, $^{35}$S, $^{90}$Y, $^{99m}$Tc, $^{111}$In, $^{125}$I, $^{131}$I. The radiolabels may be detected, for example, using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In some embodiments, the average number of effector molecules or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule per antibody ratio) of a conjugate may be controlled in different ways, for example, by: (i) limiting the molar excess of effector molecule-linker intermediate or linker reagent relative to antibody, (ii) limiting the conjugation reaction time or temperature, (iii) partial or limiting reducing conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acid molecules (for example, cDNA or RNA molecules) encoding the amino acid sequences of antibodies, antigen binding fragments, and conjugates that specifically bind to hMPV, as disclosed herein, are provided. Nucleic acids encoding these molecules can readily be produced using the amino acid sequences provided herein (such as the CDR sequences and $V_H$ and $V_L$ sequences), sequences available in the art (such as framework or constant region sequences), and the genetic code. In several embodiments, nucleic acid molecules can encode the $V_H$, the $V_L$, or both the $V_H$ and $V_L$ (for example in a bicistronic expression vector) of a disclosed antibody or antigen binding fragment. In some embodiments, the nucleic acid molecules encode an scFv. In several embodiments, the nucleic acid molecules can be expressed in a host cell (such as a mammalian cell) to produce a disclosed antibody or antigen binding fragment.

The genetic code can be used to construct a variety of functionally equivalent nucleic acid sequences, such as nucleic acids which differ in their sequence but which encode the same antibody sequence, or encode a conjugate or fusion protein including the $V_L$ and/or $V_H$ nucleic acid sequence.

In a non-limiting example, an isolated nucleic acid molecule encodes the $V_H$ of the MPV196 antibody or antigen binding fragment and comprises the nucleic acid sequence set forth as SEQ ID NO: 3. In a non-limiting example, an isolated nucleic acid molecule encodes the $V_L$ of the MPV196 antibody or antigen binding fragment and comprises the nucleic acid sequence set forth of SEQ ID NO: 4. In a non-limiting example, an isolated nucleic acid molecule encodes the $V_H$ and $V_L$ of the MPV196 antibody or an antigen binding fragment thereof and comprises the nucleic acid sequences set forth as any one of SEQ ID NOs: 3 and 4, respectively.

In another non-limiting example, an isolated nucleic acid molecule encodes the $V_H$ of the MPV201 antibody or antigen binding fragment and comprises the nucleic acid sequence set forth as SEQ ID NO: 13. In a non-limiting example, an isolated nucleic acid molecule encodes the $V_L$ of the MPV201 antibody or antigen binding fragment and comprises the nucleic acid sequence set forth of SEQ ID NO: 14. In a non-limiting example, an isolated nucleic acid molecule encodes the $V_H$ and $V_L$ of the MPV201 antibody or an antigen binding fragment thereof and comprises the nucleic acid sequences set forth as any one of SEQ ID NOs: 13 and 14, respectively.

In another non-limiting example, an isolated nucleic acid molecule encodes the $V_H$ of the MPV314 antibody or antigen binding fragment and comprises the nucleic acid sequence set forth as SEQ ID NO: 23. In a non-limiting example, an isolated nucleic acid molecule encodes the $V_L$ of the MPV314 antibody or antigen binding fragment and comprises the nucleic acid sequence set forth of SEQ ID NO: 24. In a non-limiting example, an isolated nucleic acid molecule encodes the $V_H$ and $V_L$ of the MPV314 antibody or an antigen binding fragment thereof and comprises the nucleic acid sequences set forth as any one of SEQ ID NOs: 23 and 24, respectively.

In yet a further non-limiting example, an isolated nucleic acid molecule encodes the $V_H$ of the MPV364 antibody or antigen binding fragment and comprises the nucleic acid sequence set forth as SEQ ID NO: 33. In a non-limiting example, an isolated nucleic acid molecule encodes the $V_L$ of the MPV364 antibody or antigen binding fragment and comprises the nucleic acid sequence set forth of SEQ ID NO: 34. In a non-limiting example, an isolated nucleic acid molecule encodes the $V_H$ and $V_L$ of the MPV364 antibody or an antigen binding fragment thereof and comprises the nucleic acid sequences set forth as any one of SEQ ID NOs: 33 and 34, respectively.

In another non-limiting example, an isolated nucleic acid molecule encodes the $V_H$ of the MPV458 antibody or antigen binding fragment and comprises the nucleic acid sequence set forth as SEQ ID NO: 51. In a non-limiting example, an isolated nucleic acid molecule encodes the $V_L$ of the MPV3458 antibody or antigen binding fragment and comprises the nucleic acid sequence set forth of SEQ ID NO: 52. In a non-limiting example, an isolated nucleic acid molecule encodes the $V_H$ and $V_L$ of the MPV458 antibody or an antigen binding fragment thereof and comprises the nucleic acid sequences set forth as any one of SEQ ID NOs: 51 and 52, respectively.

In yet a further non-limiting example, an isolated nucleic acid molecule encodes the $V_H$ of the MPV465 antibody or antigen binding fragment and comprises the nucleic acid sequence set forth as SEQ ID NO: 61. In a non-limiting example, an isolated nucleic acid molecule encodes the $V_L$ of the MPV465 antibody or antigen binding fragment and comprises the nucleic acid sequence set forth of SEQ ID NO: 62. In a non-limiting example, an isolated nucleic acid molecule encodes the $V_H$ and $V_L$ of the MPV465 antibody or an antigen binding fragment thereof and comprises the nucleic acid sequences set forth as any one of SEQ ID NOs: 61 and 62, respectively.

Nucleic acid molecules encoding the antibodies, antigen binding fragments, and conjugates that specifically bind to hMPV F protein can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements).

Nucleic acids can also be prepared by amplification methods. Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as bacteria, plant, yeast, insect and mammalian cells. The antibodies, antigen binding fragments, and conjugates can be expressed as individual proteins including the $V_H$ and/or $V_L$ (linked to an effector molecule or detectable marker as needed), or can be expressed as a fusion protein. Any suitable method of expressing and purifying antibodies and antigen binding fragments may be used; non-limiting examples are provided in Al-Rubeai (Ed.), *Antibody Expression and Production*, Dordrecht; New York: Springer, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ domains joined by the flexible linker (see, e.g., Bird et al., *Science*, 242(4877):423-426, 1988; Huston et al., *Proc. Natl. Acad. Sci. U.S.A.*, 85(16):5879-5883, 1988; McCafferty et al., *Nature*, 348:552-554, 1990; Kontermann and Dübel (Eds.), *Antibody Engineering*, Vols. 1-2, 2$^{nd}$ ed., Springer-Verlag, 2010; Greenfield (Ed.), *Antibodies: A Laboratory Manual*, 2$^{nd}$ ed. New York: Cold Spring Harbor Laboratory Press, 2014). Optionally, a cleavage site can be included in a linker, such as a furin cleavage site.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to hMPV F protein and another antigen. The encoded $V_H$ and $V_L$ optionally can include a furin cleavage site between the $V_H$ and $V_L$ domains.

One or more DNA sequences encoding the antibodies, antigen binding fragments, or conjugates can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells such as the COS, CHO, HeLa and myeloma cell lines, can be used to express the disclosed antibodies and antigen binding fragments. Methods of stable transfer, meaning that the foreign DNA is continuously maintained in the host may be used. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For *E. coli*, this can include a promoter such as the T7, trp, lac, or lamda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by any suitable method such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the antibodies, antigen binding fragments, and conjugates can be purified according to standard procedures in the art, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The antibodies, antigen binding fragment, and conjugates need not be 100% pure. Once purified, partially or to homogeneity as desired, if to be used prophylactically, the polypeptides should be substantially free of endotoxin.

Methods for expression of antibodies, antigen binding fragments, and conjugates, and/or refolding to an appropriate active form, from mammalian cells, and bacteria such as *E. coli* have been described and are applicable to the antibodies disclosed herein. See, e.g., Greenfield (Ed.), *Antibodies: A Laboratory Manual, 2ⁿᵈ* ed. New York: Cold Spring Harbor Laboratory Press, 2014, Simpson et al. (Eds.), *Basic methods in Protein Purification and Analysis: A Laboratory Manual*, New York: Cold Spring Harbor Laboratory Press, 2009, and Ward et al., *Nature* 341(6242): 544-546, 1989.

D. Methods and Compositions

1. Inhibiting an hWPV Infection

Methods are disclosed herein for the inhibition of an hMPV infection in a subject. The methods include administering to the subject an effective amount (that is, an amount effective to inhibit the hMPV infection in the subject) of a disclosed antibody, antigen binding fragment, conjugate, or a nucleic acid encoding such an antibody, antigen binding fragment, or conjugate, to a subject at risk of an hMPV infection or having an hMPV infection. The methods can be used pre-exposure or post-exposure.

The hMPV infection does not need to be completely eliminated or inhibited for the method to be effective. For example, the method can decrease the hMPV infection by a desired amount, for example by at least 10%, at least 20%, at least 50%, at least 60%, at least 70%, at least 80%, at least 90%, at least 95%, at least 98%, or even at least 100% (elimination or prevention of detectable hMPV infection) as compared to the hMPV infection in the absence of the treatment. In some embodiments, the subject can also be treated with an effective amount of an additional agent, such as an anti-viral agent.

In some embodiments, administration of an effective amount of a disclosed antibody, antigen binding fragment, conjugate, or nucleic acid molecule, inhibits the establishment of an hMPV infection and/or subsequent disease progression in a subject, which can encompass any statistically significant reduction in hMPV activity (for example, growth or invasion) or symptoms of the hMPV infection in the subject.

Methods are disclosed herein for the inhibition of an hMPV replication in a subject. The methods include administering to the subject an effective amount (that is, an amount effective to inhibit hMPV replication in the subject) of a disclosed antibody, antigen binding fragment, conjugate, or a nucleic acid encoding such an antibody, antigen binding fragment, or conjugate, to a subject at risk of an hMPV infection or having an hMPV infection. The methods can be used pre-exposure or post-exposure.

Methods are disclosed for treating an hMPV infection in a subject. Methods are also disclosed for preventing an hMPV infection in a subject. These methods include administering one or more hMPV F protein-specific antibodies, antigen binding fragments, bispecific antibodies, conjugates, or nucleic acid molecule encoding such molecules, or a composition including such molecules, as disclosed herein.

Antibodies and antigen binding fragments thereof can be administered by intravenous infusion. Doses of the antibody or antigen binding fragment vary, but generally range between about 0.5 mg/kg to about 50 mg/kg, such as a dose of about 1 mg/kg, about 5 mg/kg, about 10 mg/kg, about 20 mg/kg, about 30 mg/kg, about 40 mg/kg, or about 50 mg/kg. In some embodiments, the dose of the antibody or antigen binding fragment can be from about 0.5 mg/kg to about 5 mg/kg, such as a dose of about 1 mg/kg, about 2 mg/kg, about 3 mg/kg, about 4 mg/kg or about 5 mg/kg. The antibody or antigen binding fragment is administered according to a dosing schedule determined by a medical practitioner. In some examples, the antibody or antigen binding fragment is administered weekly, every two weeks, every three weeks or every four weeks.

In some embodiments, the method of inhibiting the hMPV infection in a subject further comprises administration of one or more additional agents to the subject. Additional agents of interest include, but are not limited to, anti-viral agents.

In some embodiments, the method comprises administration of a first antibody that specifically binds to hMPV F protein as disclosed herein and a second antibody that also specifically binds to hMPV F protein, such as a different epitope of hMPV F protein In some embodiments, the first antibody is one of MPV196, MPV201, MPV314, MPV364, MPV458 or MPV465. In further embodiments, the second antibody is DDS7 or MPE8. In more embodiments, the first antibody is one of MPV196, MPV201, MPV314, MPV364, MPV458 or MPV465 and the second antibody is another of MPV196, MPV201, MPV314, MPV364, MPV458 or MPV465. An effective amount of one, two, three or four, five, or six of MPV196, MPV201, MPV314, MPV364, MPV458 and/or MPV465 can be administered to a subject.

In some embodiments, a subject is administered DNA or RNA encoding a disclosed antibody to provide in vivo antibody production, for example using the cellular machinery of the subject. Any suitable method of nucleic acid administration may be used; non-limiting examples are provided in U.S. Pat. Nos. 5,643,578, 5,593,972 and 5,817, 637. U.S. Pat. No. 5,880,103 describes several methods of delivery of nucleic acids encoding proteins to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof. In some embodiments, a disclosed antibody or antigen binding fragment is expressed in a subject using the pVRC8400 vector (described in Barouch et al., *J. Virol.,* 79(14), 8828-8834, 2005, which is incorporated by reference herein).

In several embodiments, a subject (such as a human subject at risk of an hMPV infection or having an hMPV infection) can be administered an effective amount of an AAV viral vector that comprises one or more nucleic acid molecules encoding a disclosed antibody or antigen binding fragment. The AAV viral vector is designed for expression of the nucleic acid molecules encoding a disclosed antibody or antigen binding fragment, and administration of the effective amount of the AAV viral vector to the subject leads to expression of an effective amount of the antibody or antigen binding fragment in the subject. Non-limiting examples of AAV viral vectors that can be used to express a disclosed antibody or antigen binding fragment in a subject include those provided in Johnson et al., *Nat. Med.,* 15(8): 901-906, 2009 and Gardner et al., *Nature,* 519(7541):87-91, 2015, each of which is incorporated by reference herein in its entirety.

In one embodiment, a nucleic acid encoding a disclosed antibody, or antigen binding fragment thereof, is introduced directly into tissue. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

Single or multiple administrations of a composition including a disclosed hMPV F protein-specific antibody, antigen binding fragment, conjugate, or nucleic acid molecule encoding such molecules, can be administered depending on the dosage and frequency as required and tolerated by the patient. The dosage can be administered once, but may be applied periodically until either a desired result is achieved or until side effects warrant discontinuation of therapy. Generally, the dose is sufficient to inhibit an hMPV infection without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The effective dose can be determined from cell culture assays and animal studies.

The hMPV F protein-specific antibody, antigen binding fragment, bispecific antibody, conjugate, or nucleic acid molecule encoding such molecules, or a composition including such molecules, can be administered to subjects in various ways, including local and systemic administration, such as, e.g., by injection subcutaneously, intravenously, intra-arterially, intraperitoneally, intramuscularly, intradermally, or intrathecally. In an embodiment, the antibody, antigen binding fragment, bispecific antibody, conjugate, or nucleic acid molecule encoding such molecules, or a composition including such molecules, is administered by a single subcutaneous, intravenous, intra-arterial, intraperitoneal, intramuscular, intradermal or intrathecal injection once a day. The antibody, antigen binding fragment, bispecific antibody, conjugate, or nucleic acid molecule encoding such molecules, or a composition including such molecules, can also be administered by direct injection at or near the site of disease. A further method of administration is by osmotic pump (e.g., an Alzet pump) or mini-pump (e.g., an Alzet mini-osmotic pump), which allows for controlled, continuous and/or slow-release delivery of the antibody, antigen binding fragment, conjugate, or nucleic acid molecule encoding such molecules, or a composition including such molecules, over a pre-determined period. The osmotic pump or mini-pump can be implanted subcutaneously, or near a target site.

2. Compositions

Compositions are provided that include one or more of the hMPV F protein-specific antibody, antigen binding fragment, conjugate, or nucleic acid molecule encoding such molecules, that are disclosed herein in a pharmaceutically acceptable carrier. In some embodiments, the composition comprises the MPV196, MPV201, MPV314 MPV364, MPV458 or MPV465 antibody disclosed herein, or an antigen binding fragment thereof. In some embodiments, the composition comprises two, three, four or more antibodies that specifically bind the hMPV F protein. The compositions are useful, for example, for example, for the inhibition or detection of an hMPV infection. The compositions can be prepared in unit dosage forms for administration to a subject. The amount and timing of administration are at the discretion of the administering physician to achieve the desired purposes. The antibody, antigen binding fragment, conjugate, or nucleic acid molecule encoding such molecules can be formulated for systemic or local administration. In one example, the, antigen binding fragment, conjugate, or nucleic acid molecule encoding such molecules, is formulated for parenteral administration, such as intravenous administration.

In some embodiments, the antibody, antigen binding fragment, or conjugate thereof, in the composition is at least 70% (such as at least 75%, at least 80%, at least 85%, at least 90%, at least 95%, at least 96%, at least 97%, at least 98% or at least 99%) pure. In some embodiments, the composition contains less than 10% (such as less than 5%, less than 4%, less than 3%, less than 2%, less than 1%, less than 0.5%, or even less) of macromolecular contaminants, such as other mammalian (e.g., human) proteins.

The compositions for administration can include a solution of the antibody, antigen binding fragment, conjugate, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by any suitable technique. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration comprises about 0.01 to about 30 mg/kg of antibody or antigen binding fragment or conjugate per subject per day (or the corresponding dose of a conjugate including the antibody or antigen binding fragment). Any suitable method may be used for preparing administrable compositions; non-limiting examples are provided in such publications as

*Remington: The Science and Practice of Pharmacy,* 22nd ed, London, UK: Pharmaceutical Press, 2013. In some embodiments, the composition can be a liquid formulation including one or more antibodies, antigen binding fragments (such as an antibody or antigen binding fragment that specifically binds to PfCSP), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of Rituximab in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled-release parenteral formulations can be made as implants, oily injections, or as particulate systems. For a broad overview of protein delivery systems see, Banga, Therapeutic *Peptides and Proteins: Formulation, Processing, and Delivery Systems,* Lancaster, PA: Technomic Publishing Company, Inc., 1995. Particulate systems include microspheres, microparticles, microcapsules, nanocapsules, nanospheres, and nanoparticles. Microcapsules contain the active protein agent, such as a cytotoxin or a drug, as a central core. In microspheres, the active protein agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, *Colloidal Drug Delivery Systems,* J. Kreuter (Ed.), New York, NY: Marcel Dekker, Inc., pp. 219-342, 1994; and Tice and Tabibi, *Treatise on Controlled Drug Delivery: Fundamentals, Optimization, Applications,* A. Kydonieus (Ed.), New York, NY: Marcel Dekker, Inc., pp. 315-339, 1992.

Polymers can be used for ion-controlled release of the antibody compositions disclosed herein. Any suitable polymer may be used, such as a degradable or nondegradable polymeric matrix designed for use in controlled drug delivery. Alternatively, hydroxyapatite has been used as a microcarrier for controlled release of proteins. In yet another aspect, liposomes are used for controlled release as well as drug targeting of the lipid-capsulated drug.

2. Methods of Detection and Diagnosis

Methods are also provided for the detection of the presence of hMPV F protein in vitro or in vivo. In one example, the presence of hMPV F protein is detected in a biological sample from a subject and can be used to identify a subject with an hMPV infection. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, with an antibody or antigen binding fragment that specifically binds to hMPV F protein, or conjugate thereof (e.g., a conjugate including a detectable marker) under conditions sufficient to form an immune complex, and detecting the immune complex (e.g., by detecting a detectable marker conjugated to the antibody or antigen binding fragment.

In one embodiment, the antibody or antigen binding fragment is directly labeled with a detectable marker. In another embodiment, the antibody that binds the hMPV F protein (the primary antibody) is unlabeled and a secondary antibody or other molecule that can bind the primary antibody is utilized for detection. The secondary antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially. Suitable labels for the antibody, antigen binding fragment or secondary antibody are known and described above, and include various enzymes, prosthetic groups, fluorescent materials, luminescent materials, magnetic agents and radioactive materials.

In some embodiments, the disclosed antibodies or antigen binding fragments thereof are used to test vaccines. For example, to test if a vaccine composition including hMPV F protein or fragment thereof assumes a prefusion conformation including the epitope of a disclosed antibody. Thus, provided herein is a method for testing a vaccine, wherein the method comprises contacting a sample containing the vaccine, such as a hMPV F protein immunogen, with a disclosed antibody or antigen binding fragment under conditions sufficient for formation of an immune complex, and detecting the immune complex, to detect the vaccine including the epitope of interest in the sample. In one example, the detection of the immune complex in the sample indicates that vaccine component, such as an hMPV F protein immunogen assumes a conformation capable of binding the antibody or antigen binding fragment.

EXAMPLES

The hMPV genome consists of approximately 13,000 nucleotides, with eight genes encoding nine proteins, three of which are the surface glycoproteins—small hydrophobic (SH), attachment (G), and fusion (F) proteins. The hMPV F protein is the sole target of the neutralizing antibody response to hMPV (Ulbrandt et al. 2008. J Gen Virol 89:3113-3118). This is in contrast to RSV where both the RSV G and RSV F proteins elicit neutralizing antibodies (Tripp et al. 2017. J Virol 92:1-8.). The RSV/hMPV F proteins also demonstrate a high degree of conservation between the A and B virus genotypes, a key advantage for developing broadly-reactive vaccines and therapeutics (Van Den Hoogen et al. 2004. Emerg Infect Dis 10:658-666). The RSV and hMPV F proteins mediate membrane fusion between the viruses and host cell membranes, however, the exact mechanism for membrane fusion for RSV and hMPV has yet to be determined. Similar to RSV, hMPV can mediate infection in the absence of the hMPV G protein in vitro, although such viruses are attenuated in vivo (Skiadopoulos et al. 2004. J Virol 78:12877-12887). The hMPV F protein has an RGD motif hypothesized to interact with $\alpha5\beta1$ integrins (Cox et al. 2012. J Virol 86:12148-12160), and heparin sulfate has also been shown to play a role in hMPV F protein-mediated attachment (Chang et al. 2012. J Virol 86:3230-3243).

The hMPV F protein is a trimeric, class I viral fusion protein that is initially synthesized as a precursor monomer ($F_0$) that homotrimerizes after proteolytic cleavage into a metastable pre-fusion conformation. Crystal structures of both conformations of the hMPV F protein have been determined (Battles et al. 2017. Nat Commun 8:1528; Más et al. 2016. PLoS Pathog 12:e1005859). The hMPV pre-fusion and post-fusion F proteins have been shown to elicit similar antibody responses (Battles et al. 2017. Nat Commun 8:1528), unlike the RSV F protein (McLellan et al. 2013. Science 340:1113-1117) and the related parainfluenza virus F proteins (Stewart-Jones et al. 2018. PNAS https://doi.org/10.1073/pnas.1811980115), where pre-fusion-elicited antibodies are more abundant and potently neutralizing. Importantly, the hMPV F protein is cleaved by different intracellular enzymes than RSV F (Schowalter et al. 2006. J Virol 80:10931-10941), and in some strains low pH is required to activate the fusion mechanism (Schowalter et al. 2006. J Virol 80:10931-10941). hMPV can fuse with host cells at either the cell membrane or the endosomal membrane, rather than just at the cell membrane as for RSV (Cox et al. 2015. PLoS Pathog 11:e1005303).

Neutralizing regions in the hMPV F protein have been determined via mAb-resistant mutant generation using mAbs derived from immunization of Armenian hamsters (Ulbrandt et al. 2008. J Gen Virol 89:3113-3118) and BALB/c mice (Ulbrandt et al. 2006. J Virol 80:7799-7806). A human mAb derived from a phage display library has been discovered (Williams et al. 2007. J Virol 81:8315-8324), and was co-crystallized with a fragment of pre-fusion hMPV F (Wen et al. 2012. Nat Struc Mol Biol 19:461-463). As RSV F and hMPV F proteins share approximately 30% sequence homology, it is not surprising that mAbs have been generated that neutralize both viruses). mAb 54G10 binds near antigenic site IV on the RSV F protein, and reduces lung titers of hMPV and RSV in vivo (Schuster et al. 2014. J Infect Dis 211:1-34). The crystal structure of MPE8 (Corti et al. 2013. Nature 501:439-43) in complex with the RSV F protein has been determined, and has a similar binding profile as mAb 25P13 (Wen et al. 2017. Nat Microbiol 2:16272). Another human mAb isolated is 17E10, which targets antigenic site IV with a binding pose facilitating cross-reactivity between RSV and hMPV F proteins (Mousa et al. 2018. PLoS Pathog 14:e1006837). While several mouse and a few human mAbs have been isolated that target the hMPV F protein, the major antigenic sites on the hMPV F protein, and the antibodies elicited are unclear. Four new neutralizing human mAbs were isolated to the hMPV F protein.

Example 1

Analysis of Recombinant hMPV F Protein in HEK293F Cells

Similar to the RSV F protein, the hMPV F protein is translated as a single chain protein ($F_0$) that is cleaved into two fragments ($F_1$ and $F_2$) and joined at disulfide bridges before transport to the cellular membrane. While the RSV F protein is cleaved at two positions by furin to release a small protein fragment, the hMPV F protein contains one cleavage site that is cleaved by a yet-to-be determined intracellular protease (Schowalter et al. 2006. J Virol 80:10931-10941). The hMPV F protein can be cleaved by trypsin in vitro, which has been utilized for virus growth and neutralization assays. A partial fragment of monomeric hMPV F protein in the pre-fusion conformation bound to the neutralizing mAb DS7 has been reported (Wen et al. 2012. Nat Struc Mol Biol 19:461-463). More recently, X-ray crystal structures of both pre-fusion (MPV 115-BV) (Battles et al. 2017. Nat Commun 8:1528) and post-fusion (MPV F Furin $\Delta$FP) (Wen et al. 2012. Nat Struc Mol Biol 19:461-463) hMPV F protein ectodomains recombinantly expressed in CV-1 cells have been reported. The hMPV F protein cleavage site was substituted in both of these protein constructs with the furin cleavage site of the RSV F protein. For the post-fusion hMPV F protein crystal structure, addition of a trimerization domain facilitated protein trimerization, and co-expression with furin further enhanced the homogeneity of the protein in the post-fusion conformation. For antibody isolation, four subgroups of the hMPV F protein were expressed in HEK293F cells, the constructs contained a trimerization domain, and the cleavage site was replaced by the furin cleavage site from the RSV F protein as previously described for the post-fusion hMPV F protein (Más et al. 2016. PLoS Pathog 12:e1005859). All four proteins expressed well in HEK293F cells, at quantities of at least 1 mg protein/L of culture volume. Although the proteins did contain a trimerization domain and a furin cleavage site that is suitable for cleavage and trimerization of the RSV F protein in HEK293F cells (McLellan et al. 2011. J Virol 85:7788-7796), monomeric protein was observed after purification and analysis by size exclusion chromatography (FIG. 1A). This is in contrast to expression in CV-1 cells, where expression of the hMPV F protein with a trimerization domain in the absence of co-expressed furin facilitated protein trimerization (Más et al. 2016. PLoS Pathog 12:e1005859). As the majority of antigenic sites likely reside on each monomer of the hMPV F protein, this protein was utilized for subsequent antibody isolation and binding studies. To obtain trimeric hMPV F protein, a previously described methodology was utilized (Más et al. 2016. PLoS Pathog 12:e1005859) whereby the protein is incubated with trypsin to induce cleavage and subsequent trimerization. Indeed, upon trypsin cleavage, a shift in the size exclusion profile was observed indicating the protein had trimerized (FIG. 1A). Further analysis by negative-stain electron microscopy revealed a homogeneous population resembling the post-fusion conformation of the hMPV F protein (FIG. 1B).

Example 2

Isolation of Human mAbs

Previous reports have described the majority of antibodies found in human serum bind both pre-fusion and post-fusion hMPV F proteins (Battles et al. 2017. Nat Commun 8:1528). This is in contrast to those antibodies binding the RSV F protein, whereby the preponderance of antibodies in sera are pre-fusion specific (Ngwuta et al. 2015. Sci Transl Med 7:309ra162). In order to expand the knowledge on the human antibody response to the hMPV F protein, four new human mAbs were isolated targeting the hMPV F protein.

The majority of individuals are seropositive for hMPV by 5 years of age (Edwards et al. 2013. N Engl J Med 368:633-643), therefore, healthy donors were recruited for blood draws and subsequent mAb isolation. A high frequency of hMPV F-specific B cells was observed from a nineteen-year-old female, and cells from this donor were used in subsequent mAb isolation experiments (FIG. 1C). B cells from cultures producing antibodies reactive to the hMPV F protein were used to generate stable hybridoma cell lines (Mousa et al. 2016. PNAS 113:E6849-E6858). Hybridoma populations were biologically cloned by single-cell flow cytometric sorting, and expanded stepwise before growing in serum-free media for antibody purification. Four new mAbs were isolated, MPV196, MPV201, MPV314, and MPV364, and isotyping analysis was completed for each mAb. All four antibodies were of the IgG$_1$ isotype. mAbs MPV201 and MPV314 contain kappa light chains, while mAbs MPV364 and MPV196 utilize lamda light chains.

Example 3

Binding and Neutralization Characteristics of hMPV F-Specific Human mAbs

Previously isolated mouse mAbs to the hMPV F protein were shown to neutralize the virus and protect against viral replication in vivo, however, the majority of the mAbs did not neutralize across subgroups (Ulbrandt et al. 2006. J Virol 80:7799-7806). In contrast, the limited number of human mAbs isolated that were shown to neutralize both RSV and hMPV show broad activity across hMPV subgroups (Corti et al. 2013. Nature 501:439-43; Schuster et al. 2014. J Infect Dis 211:1-34; Wen et al. 2017. Nat Microbiol 2:16272; Mousa et al. 2018. PLoS Pathog 14:e1006837).

Figure 2B:
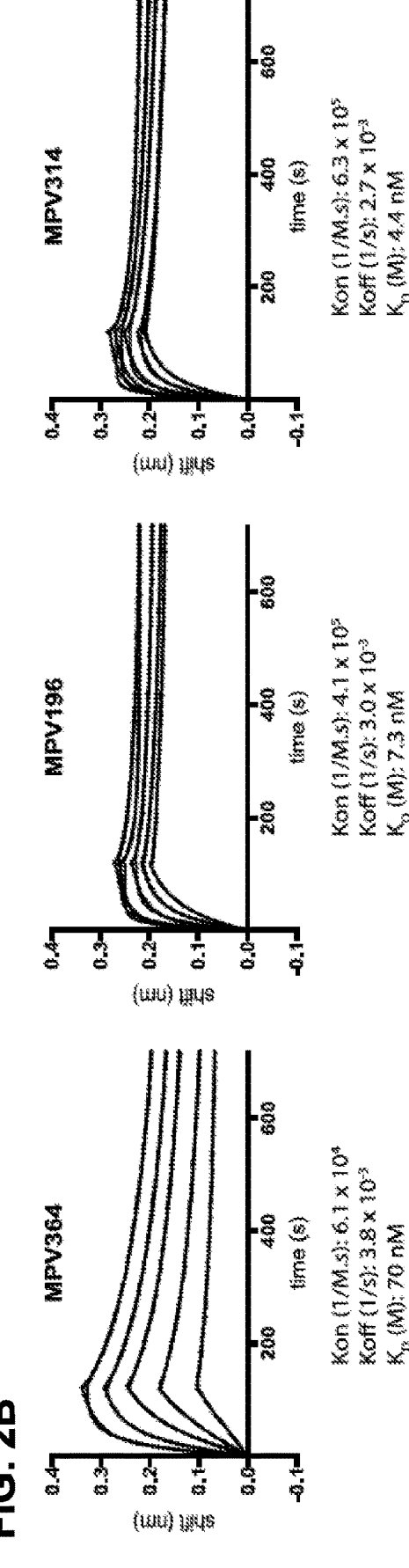
Figure 3:
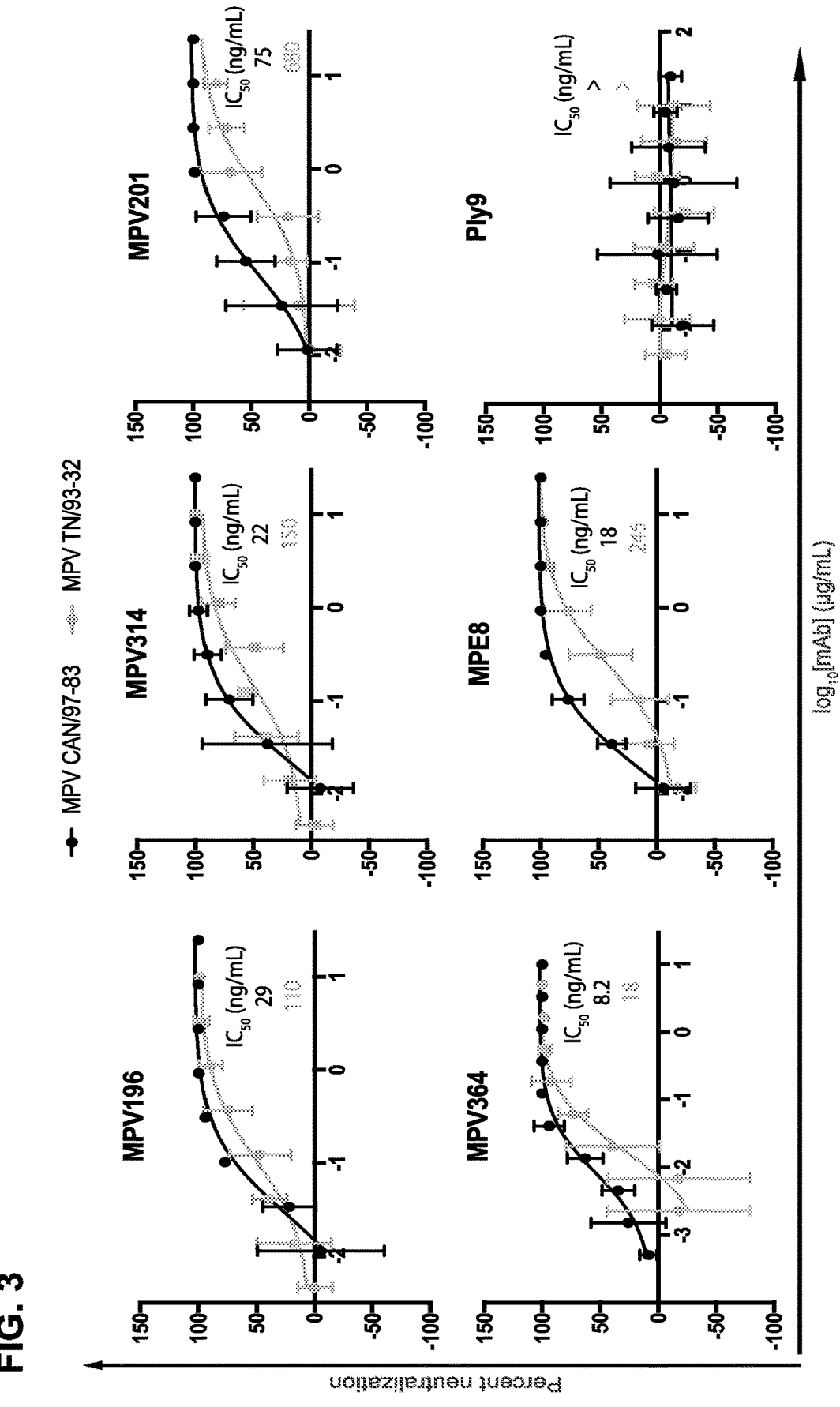
FIG. 3. Neutralization profiles of the hMPV F protein-specific mAbs. Neutralization curves for the human mAbs and controls. $IC_{50}$ values are inlaid for each graph and are color coded with the legend at the top of each curve. Data represent the average of three replicates, and error bars are 95% confidence intervals. Data are representative of two independent experiments.

To determine the breadth of binding of the isolated human mAbs, binding was examined by ELISA to the hMPV F protein from each of the four subgroups of hMPV F, as well as to the trimeric hMPV A1 F protein isolated following trypsin cleavage (FIG. 2A, 1A, 1B). All four mAbs bound to hMPV F proteins from each of the four hMPV F protein subgroups, and none of the four mAbs showed cross-reactivity with the pre-fusion RSV F protein A2 SC-TM (Krarup et al. 2015. Nat Commun 6:8143). mAbs MPV196, MPV314, and MPV201 showed equivalent binding to each other, while MPV364 binding was marginally lower based on EC$_{50}$ determined by ELISA, suggesting the affinity for MPV364 is lower for the hMPV F protein (FIG. 2A). Two control mAbs previously discovered to cross-react between RSV F and hMPV F proteins were included, i.e. the humanized mouse mAb 101F (Wu et al. 2007. J Gen Virol 88:2719-2723), and the human mAb MPE8 (Corti et al. 2013. Nature 501:439-43). The epitope for 101F is known to include a conserved GIIK motif on both RSV F and hMPV F proteins (Más et al. 2016. PLoS Pathog 12:e1005859), and is shared by the site IV cross-reactive mAb 17E10 (Mousa et al. 2018. PLoS Pathog 14:e1006837). Notably, MPE8 is pre-fusion F protein-specific (Battles et al. 2017. Nat Commun 8:1528; Corti et al. 2013. Nature 501:439-43), and no binding was observed to the hMPV F protein constructs, suggesting these proteins were in the post-fusion conformation, which is consistent with results from negative-stain electron microscopy following trypsin cleavage (FIG. 2A, 1B). To analyze whether MPV364 had a decreased ON rate or OFF rate compared to the remaining mAbs, MPV364, MPV196, and MPV314 were cleaved to Fab fragments by papain digestion and affinity studies were performed via biolayer interferometry (FIG. 2B). MPV364 has a 10-fold higher K$_D$ as compared to MPV196 and MPV314, which is due to a slower ON rate of the Fab to the hMPV F protein. Overall, these data are consistent with the increased EC$_{50}$ of MPV364 compared to MPV196, MPV201, and MPV314.

To determine if the isolated mAbs neutralize hMPV infection, plaque neutralization assays were performed using immunostaining for plaque visualization. mAbs were tested for neutralization against hMPV CAN/97-83, and hMPV TN/93-32, which are representative of the A and B genotypes, respectively. All four mAbs neutralized both genotypes of hMPV. Surprisingly, MPV364 was the most potently neutralizing mAb with IC$_{50}$ values of 8 and 18 ng/mL for MPV CAN/97-83 and MPV TN/93-32, respectively. The IC$_{50}$ is at least 1 log lower than the other three mAbs for the MPV TN/93-32 strain, while the K$_D$ for MPV364 is 1 log higher than the remaining mAbs. Thus, while MPV364 shows the weakest binding affinity among the four mAbs, it exhibits the most potent neutralizing activity. These data led to experiments to probe the antigenic regions targeted by each mAb to determine if the epitope was important for neutralization potency. This has been previously shown for RSV F protein, whereby pre-fusion F protein-specific mAbs D25 (McLellan et al. 2013. Science 340:1113-1117) and hRSV90 (Mousa et al. 2017. Nat Microbiol 2:16271) exhibit potent neutralizing activity well below mAbs that bind both pre-fusion and post-fusion F protein conformations.

Example 4

Epitope Determination of the Newly Isolated mAbs

To determine the antigenic site targeted by the isolated human mAbs, epitope binning was performed, i.e. where antibodies are tested in a pairwise combinatorial manner for those that compete for the same binding region, which are then grouped together into bins using the OCTET®RED384 system. Previously discovered human mAbs were utilized to identify the general antigenic regions on the hMPV F protein. The hMPV/RSV cross-reactive humanized mouse mAb 101F (Wu et al. 2007. J Gen Virol 88:2719-2723; McLellan et al. 2010. J Virol 84:12236-12244) was used to identify antigenic site IV, and the cross-reactive human mAbs MPE8 (Corti et al. 2013. Nature 501:439-43) and 25P13 (Wen et al. 2017. Nat Microbiol 2:16272) were used to identify antigenic site III. The previously discovered mAb DS7 (Wen et al. 2012. Nat Struc Mol Biol 19:461-463) was also incorporated, which was derived from a human phage display library. Each mAb was competed for binding against itself and other mAbs in the group. Anti-penta-HIS biosensors were loaded with the hMPV F protein, after which mAbs were loaded as either the first and second mAb in different experiments. Although MPE8 did not show substantial binding to the hMPV F protein by ELISA, significant binding was observed via biolayer interferometry at a concentration of 100 µg/mL, suggesting the MPE8 epitope is at least partially conserved in the post-fusion conformation of hMPV F protein. The mAbs were observed to fall into three groups (FIG. 4A). The mAbs MPV201, MPV314, and MPV196 all competed primarily with mAb DS7, and partially with MPE8 and 25P13 at antigenic site III. Antigenic site III lies in close proximity to the DS7 antigenic site, and mAbs 25P13 and DS7 show partial competition. mAb MPV364 instead competes primarily with mAbs MPE8 and 25P13 at antigenic site III. While mAbs MPE8 and 25P13 partially compete with mAbs MPV196, MPV201, and MPV314, MPV364 shows no competition with these mAbs except one-directionally on the MPV A1 F protein. The crystal structure of MPE8 in complex with the RSV F protein was recently determined (Wen et al. 2017. Nat Microbiol 2:16272). Based on a structural overlay of the pre-fusion RSV and hMPV F proteins, MPV364 likely binds in a slightly altered angle as compared to MPE8, shifting away from the DS7 site (FIG. 4B). Both MPE8 and 25P13 are cross-reactive between hMPV and RSV F proteins, however, no such cross-reactivity was observed for MPV364. It is therefore surmised that the altered binding pose of MPV364 reduces the cross-reactivity with RSV F, binding at a nearby antigenic site, which is termed here antigenic site IIIa.

The $IC_{50}$ (the concentration of antibody that neutralizes 50% of virus) was also determined. For each antibody listed below, the first number is neutralization of A2 virus, and the second number is neutralization of B2 virus.

MPV196: 29 ng/µL, 110 ng/µL
MPV314: 22 ng/µL, 150 ng/µL
MPV201 75 ng/µL, 680 ng/µL

In comparison, the values for DS7 Fab are as follows: 1100 ng/µL (A2 virus), no neutralization (B2 virus), 2400 µg/mL (A1 virus), 9800 µg/mL (B1 virus). These values were reported for 60% plaque reduction but can still be directly compared.

In summary, MPV196, MPV314, and MPV201 have the unique property that they neutralize B2 virus, as compared to commercially available antibodies.

Example 5

Sequence Determinants of MPV364

The sequence of MPV364 heavy and light chain variable regions were determined by RNA isolation and RT-PCR of the variable regions. IMGT/V-Quest analysis predicts MPV364 utilizes VH1-3*01, JH5*02, and DH2-8*02 genes for the heavy chain and VL3-21*02 and JL*01 genes for the light chain. The CDR3 for the MPV364 heavy chain extends 21 amino acids with the sequence ARVDQYCIGGVCYGGKNWFDP (SEQ ID NO: 47), while the light chain CDR3 is 12 amino acids in length with the sequence QVWDRDSDHPYV (SEQ ID NO: 48). Both heavy and light chain V regions are heavily mutated, with percent identity to respective $V_H$ genes being 91.67% and to $V_L$ being 90.32%. These data suggest MPV364 is the result of multiple hMPV infections in this particular donor. Previously discovered antigenic site III-targeting human mAbs isolated against RSV, which also cross-react with hMPV, utilize VH3-21, VH1-46, VH3-11, and VH1-69 (Corti et al. 2013. Nature 501:439-43; Wen et al. 2017. Nat Microbiol 2:16272; Gilman et al. 2016. Sci Immunol 1:1-12). Overall, these data provide a new V gene lineage that can target the hMPV F protein at antigenic site III, but does not provide cross-reactivity with the RSV F protein.

Example 6 mAb MPV364 Reduces Viral Replication hMPV In Vivo

As MPV364 exhibits potent neutralizing activity in vitro, mAb efficacy was determined in vivo when administered before hMPV infection. Prophylactic administration of pal-ivizumab is recommended for infants at high-risk of RSV infection (Group TIm-RS. 1998. Pediatrics 102:531-537); a similar therapeutic administration can be utilized for hMPV.

MPV364 is a fully human antibody, and would likely not require extensive optimization to reduce immunogenicity in human patients. For these studies, BALB/c mice were utilized, as these animals were previously shown to be susceptible to hMPV replication (Alvarez et al. 2004. J Virol 78:14003-14011; Liu et al. 2009. J Virol 83:6837-6848; Alvarez and Tripp. 2005. J Virol 79:5971-5978).

Figures 5A, 5B:
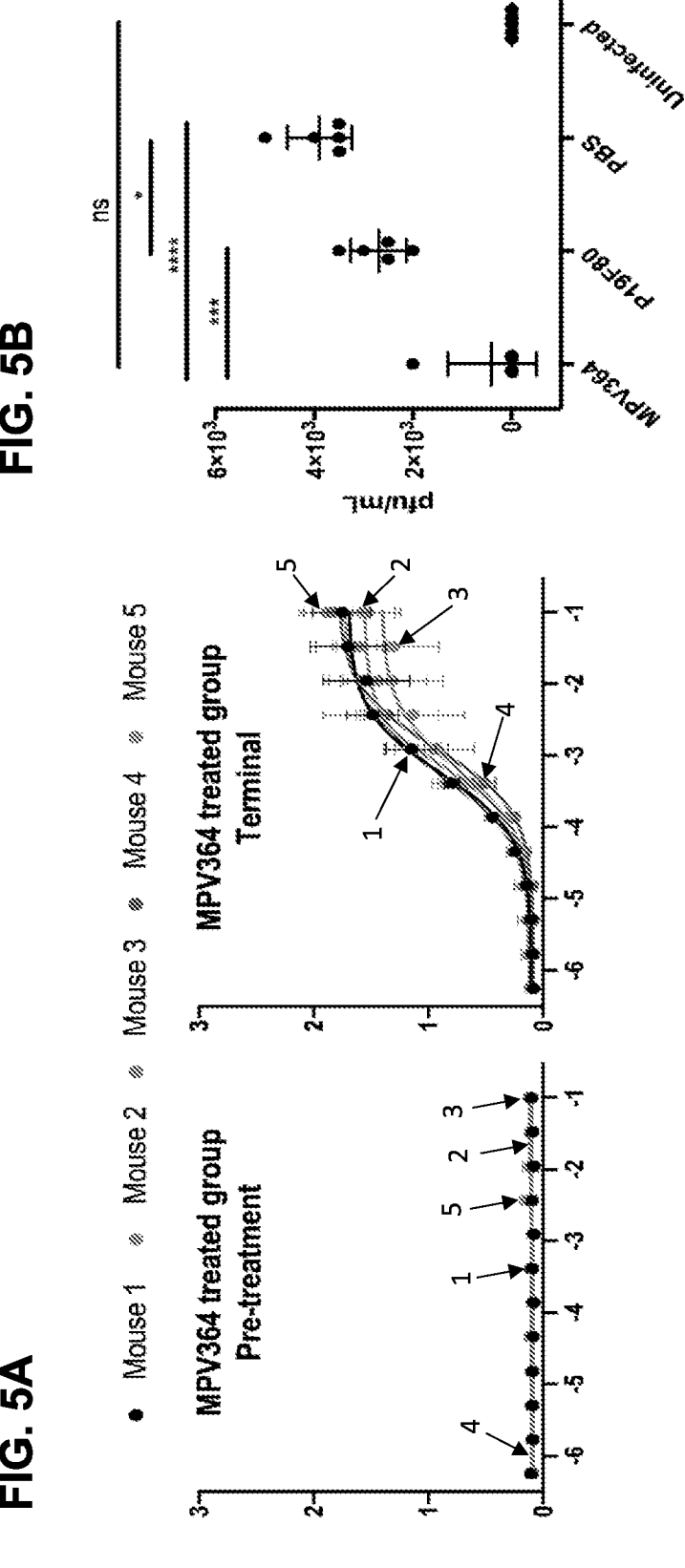
FIGS. 5A-5B. In vivo delivery of MPV364 limits viral replication in the lungs of BALB/c mice. (A) Serum pre-treatment and post-treatment was tested for the presence of human anti-hMPV F protein-specific mAbs. MPV364 titers in MPV364-treated animals had a 1/1,318 endpoint titer average between five mice, indicating intramuscular delivery was sufficient to allow transfer to the circulatory system. (B) Virus replication in the lung homogenates of BALB/c mice in each treatment group. Mice treated with MPV364 showed a significant reduction in viral titers as compared to the P19F80 control mAb treated group and the PBS-treated group. No significant difference was observed between the MPV364 treated group and the uninfected group. n=5 mice per group. **p<0.0001, *p=0.0001, *p=0.0348, ns=not significant.

One day before hMPV infection, mice were treated with 10 mg/kg of MPV364, and three additional groups were included as controls: an uninfected group, a PBS-treated group, and treatment with an $IgG_1$ isotype-control non-hMPV-specific mAb P19F80. After treatment, mice were infected the next day and sacrificed on day 5. As protection from hMPV infection is likely mediated by the Fab region of MPV364, which would inhibit the attachment and/or fusogenic activity of the hMPV F protein, the Fc region of the antibody was not isotype-switched. Intramuscular deliv-ery of MPV364 was tracked by ELISA in each mouse, and as expected, a robust signal correlating to an average 50% endpoint serum titer of $\frac{1}{1,318}$ was determined in terminal samples (FIG. 5A). To determine if MPV364 exhibited efficacy to reduce viral replication in the lungs of infected mice, lungs were harvested and homogenized in PBS five days after viral infection. Viral titers were determined using an immunostaining plaque reduction assay. A substantial reduction in lung viral titers was observed for the MPV364-treated group as compared to PBS-treated or negative con-trol antibody-treated groups (FIG. 5B). A minimal non-specific decrease in lung viral titers also observed for the control antibody P19F80. No substantial difference was observed between the MPV364-treated and the uninfected mice. Overall, these data indicate that administration of MPV364 before viral infection limits virus replication in the lungs of BALB/c mice.

While hundreds of human mAbs have been isolated to the RSV F protein, and the antigenic sites have been well characterized, the major neutralizing and nonneutralizing epitopes on the hMPV F protein targeted by the human immune system have not been determined. The isolation of human mAbs to the RSV F protein has led to the design of new vaccine constructs currently being examined in pre-clinical and clinical trials. However, there is little previous research on the epitopes targeted by human mAbs on the hMPV F protein. Disclosed herein are four new human mAbs that bind to the hMPV F protein and neutralize both genotypes of hMPV in vitro. The mAbs were mapped to two distinct antigenic sites: Antigenic site III was targeted by MPV364, and the remaining mAbs competed with phage-display-derived human mAb DS7.

MPV364 is an hMPV F-protein specific human mAb that binds at antigenic site III, and exhibits potently neutralizing activity. Furthermore, MPV364 limits virus replication in a mouse model of infection when administered prophylacti-cally. The binding affinity of hMPV F protein-specific mAbs, while important for virus neutralization, was not the sole determinant of effective neutralization. MPV364 has a 1-log fold weaker binding affinity compared to the remain-ing human mAbs, yet greater neutralization potency. This was determined to be due to the antigenic site targeted by MPV364.

The disclosed human mAbs that neutralize hMPV can be used in humans. The humanized mouse mAb, palivizumab, is administered to infants at high risk of RSV infection (Group TIm-RS. 1998. Pediatrics 102:531-537). MPV364 and the additional mAbs disclosed herein are fully human, and thus should not elicit a significant immune response. Both RSV and hMPV remain problematic viruses for vaccine design, and chemical inactivation of the viruses has been linked to the induction of Th2-skewed immune responses, and for RSV, sensitization for vaccine-induced enhanced disease upon RSV challenge (de Swart et al. 2007. Vaccine 25:8518-8528; Murphy and Walsh. 1988. J Clin Microbiol 26:1595-7). These pathogens are a concern for the very young, the elderly, and the immunocompromised. The disclosed human mAbs can serve as a means to control infection and disease in these populations.

Example 7

Materials and Methods for Examples 1-6

Blood draws and informed consent. Healthy human donors were recruited, and, after obtaining informed consent, 90 mL of blood was drawn by venipuncture into 9 heparin-coated tubes, and 10 mL of blood was collected into a serum separator tube. Peripheral blood mononuclear cells were isolated from human donor blood samples using Ficoll-HISTOPAQUE® density gradient centrifugation, and PBMCs were frozen in the liquid nitrogen vapor phase until further use.

Production and purification of recombinant hMPV F proteins. Plasmids encoding cDNAs for hMPV A1, A2, B1, and B2 F proteins (Más et al. 2016. PLoS Pathog 12:e1005859) were synthesized (Genscript) and cloned into the pcDNA3.1+ vector. The plasmids were expanded by transformation in E. coli DH5a cells using 100 μg/mL of ampicillin (Fisher Scientific) for selection. Plasmids were purified using either the ZYMOPURE™ II Maxiprep kit (Zymo Research) or the E.Z.N.A.® Plasmid Maxi Kit (Omega Biotek), both following the manufacturer's protocols. For each liter of protein expression, 1 mg of plasmid DNA was mixed with 4 mg of 25,000 molecular weight polyethylenimine (PEI, PolySciences Inc.) in OPTI-MEM™ I cell culture medium (Thermo Fisher Scientific). After 30 min, the DNA/PEI mixture was added to FREESTYLE™ HEK293F (Thermo Fisher Scientific) cells at $1\times10^6$ cells/mL in FREESTYLE™ 293 Expression Medium (Thermo Fisher Scientific). After 4-6 days, the cultures were centrifuged to pellet the cells, and the supernatants were filtered through a 0.45 μm sterile filter. Recombinant proteins were purified directly from the filtered culture supernatants using HISTRAP™ Excel columns (GE Healthcare Life Sciences). Each column was stored in 20% ethanol and washed with column volumes (CV) of 20 mM Tris pH 7.5, 500 mM NaCl before loading samples onto the column. After sample application, columns were washed with 10 CV of 20 mM Tris pH 7.5, 500 mM NaCl, 20 mM imidazole. Proteins were eluted from the column by 5 CV of 20 mM Tris pH 7.5, 500 mM NaCl, 250 mM imidazole. Proteins were concentrated and buffer exchanged using AMICON® Ultra-15 Centrifugal Filter Units with a 30 kDa molecular weight cut-off (Millipore Sigma) and buffer-exchanged into phosphate buffered saline (PBS).

Human hybridoma generation. For antibody generation experiments, 8 million previously frozen and irradiated NIH 3T3 cells modified to express human CD40L, human IL-21, and human BAFF (gift from Deepta Bhattacharya, Washington University) were mixed with 10 million PBMCs in 80 mL STEMCELL™ Media A (STEMCELL™ Technologies) containing 6.3 μg/mL of CpG (phosphorothioate-modified oligodeoxynucleotide from Invitrogen, see PCT Publication No. WO 2017/011394A1, and Bar-Peled et al., J. Virol. doi:10.1128/JVI.00342-19 (2019) doi:10.1128/jvi.00342-19, both incorporated herein by reference) and 1 μg/mL of cyclosporine A (Sigma), and cells were plated in four 96-well plates at 200 μL per well in STEMCELL™ Media A. After six days, culture supernatants were screened by ELISA for binding to recombinant hMPV F protein, and cells from positive wells were electrofused with a non-secreting myeloma cell line as previously described (Mousa et al. 2016. PNAS 113:E6849-E6858). Cells from each cuvette were resuspended in 20 mL STEMCELL™ Media A containing 1×HAT (Sigma-Aldrich), 0.2×HT (CORNING®), and 0.3 μg/mL ouabain (Fisher Scientific) and plated at 50 μL per well in a 384-well plate. After 7 days, cells were fed with 25 μL of STEMCELL™ Media A. Hybridomas were screened after two weeks for antibody production by ELISA, and cells from wells with reactive supernatants were expanded to 48-well plates for one week in 0.5 mL of STEMCELL™ Media E (STEMCELL™ Technologies), before being screened again by ELISA, and then subjected to single-cell fluorescence-activated sorting. After cell sorting into 384-well plates containing STEMCELL™ Medium A, hybridomas were screened by ELISA before further expansion.

Human mAb and Fab production and purification. Plasmids encoding cDNAs for the protein sequences of mAbs 101F, MPE8, 25P13, and DS7 were synthesized (Genscript), and heavy and light chain sequences were cloned into vectors encoding human IgG1 and lamda or kappa light chain constant regions, respectively. Large-scale DNA was isolated and mAbs were obtained by transfection into FREESTYLE™ HEK293F cells as described above. For hybridoma-derived mAbs, hybridoma cells lines were expanded in STEMCELL™ Medium A until 80% confluent in 75-cm² flasks. For antibody production, cells from one 75-cm² cell culture flask were collected with a cell scraper and expanded to four 225-cm² cell culture flasks in serum-free medium (Hybridoma-SFM, Thermo Fisher Scientific). Recombinant cultures were stopped after 4-6 days and hybridoma cultures were stopped after 30 days, and culture supernatants were sterile filtered using 0.45 μm pore size filter devices. mAbs were purified directly from culture supernatants using HITRAP™ Protein G columns (GE Healthcare Life Sciences) following the manufacturer's protocol. To obtain Fab fragments, papain digestion was used (PIERCE™ Fab Preparation Kit, Thermo Scientific). Fab fragments were purified by removing IgG and Fc contaminants using a HITRAP™ MABSELECTSURE™ following the manufacturer's protocol.

Negative-stain electron microscopy analysis. MPV A1 F protein was cleaved with trypsin-TPCK (Thermo Fisher Scientific) by incubating 1 mg of protein with 5 units of trypsin for 2 hr at 37° C. Following this, the complex was purified by size-exclusion chromatography (S200, 16/300; GE Healthcare Life Sciences) in 50 mM Tris pH 7.5, 100 mM NaCl. Carbon-coated copper grids were overlaid with the protein at 100 μg/mL for 3 min. The grid was washed in water twice and then stained with 0.75% uranyl formate for 1 min. Negative-stain electron micrographs were acquired using a JEOL JEM1011 TEM microscope equipped with a high contrast 2 k×2 k AMT mid-mount digital camera using 50,000× magnification.

Enzyme linked immunosorbent assay (ELISA) for binding to hMPV F protein. For recombinant protein capture ELISA, 384-well plates were treated with 2 μg/mL of antigen for one hour at 37° C. or overnight at 4° C. Following this, plates were blocked for one hour with 2% milk supplemented with 2% goat serum in PBS with 0.05% Tween-20 (PBS-T). Primary mAbs or culture supernatants were applied to wells for 1 hr following three washes with PBS-T. Plates were washed with PBS-T four times before applying 25 μL secondary antibody (goat anti-human IgG Fc, Meridian Life Science) at a dilution of 1:4,000 in blocking solution. After incubation for 1 hr, the plates were washed 5× with PBS-T, and 25 μL of PNPP solution (1 mg/mL PNPP in 1 M Tris base) was added to each well. The plates were incubated at room temperature for 1 hr before reading the optical density at 405 nm on a Biotek plate reader.

Isotype determination of human mAbs. For determination of mAb isotypes, 96-well IMMULON® HB 4×ELISA plates (Thermo Fisher Scientific) were coated with 2 μg/mL of each mAb in PBS. The plates were incubated at 37° C. for 1 hr or overnight at 4° C., then washed with Ix water. Plates were blocked with 2% nonfat milk block with 2% goat serum in PBS-T, then left to incubate for 1 hr at room temperature. After incubation, the plates were washed three times with PBS-T. Isotype specific antibodies obtained from Southern Biotech (goat anti-human kappa-AP #100244-340, goat anti-human lamda-AP #100244-376, mouse anti-human IgG1 (Fc)-AP #100245714, mouse anti-human IgG2 (Fc)-AP #100245-734, mouse anti-human IgG3 (Hinge)-AP #100245-824, mouse anti-human IgG4 (Fc)-AP #100245-812) were diluted 1:1000 in block, and 50 μL of each solution was added to respective wells. Plates were incubated for 1 hr at room temperature, then washed five times with PBS-T. PNPP substrate was prepared in a 1 mg/mL solution in 1 M Tris base, and 100 μL of this solution was added to each well. Plates were incubated for 1 hr and read at 405 nm on a Biotek plate reader.

RT-PCR for hybridoma mAb variable gamma chain and variable light chain. RNA was isolated from expanded hybridoma antibodies by the Zymo Research QUICK RNA™ miniprep kit following the manufacturer's protocol. Qiagen ONESTEP™ RT-PCR kit was used for cDNA synthesis and PCR amplification. For RT-PCR reactions 50 μL reactions were designed with the following final concentrations: 1×Qiagen ONESTEP™ RT-PCR Buffer, 400 μM dNTP mix, 0.6 μM primer mix, 2 μL of Qiagen ONESTEP™ RT-PCR Enzyme Mix, 600 ng total of the template RNA, and RNase-free water. Three separate sets of primer mixes were used: gamma and kappa forward and reverse primers as previously described (Thornburg et al. 2016. J Clin Invest 126:1482-1494), and lamda chain primers as previously described (Smith et al. Nat Protoc 4:372-384). After mixing, the RT-PCR reactions were placed in the thermocycler with the following program: 30 minutes at 50° C., 15 minutes at 95° C., then a 3-step cycle with 30 repeats of denaturation for 30 seconds at 94° C., annealing for 30 seconds at 50° C., and extension for 1 minute at 72° C., followed by 10 minutes of the final extension at 72° C. Samples were analyzed on the agarose gel. Sequences were analyzed using IMGT/V-QUEST (Brochet et al. 2008. Nucleic Acids Res 36:503-508).

Growth of hhMPV. hMPV B2 strain TN/93-32 was obtained from BEI Resources (NR-22240) and hMPV A2 strain CAN/97-83 was from Dr. Ralph Tripp. Viruses were grown in LLC-MK2-7.1 cells (ATCC CCL-7.1). Cells were grown to 80% confluency in 185 cm² flasks in OPTI-MEM® I supplemented with 2% FBS. For virus infection, cells were washed 2× with DPBS, and then coated with 6 mL of diluted virus. The flasks were rocked for 1 hr at room temperature to allow adsorption of virus. Following this, 10 mL of OPTI-MEM® I supplemented with 5 μg/mL trypsin-EDTA and 100 μg/mL CaCl₂ was added to the flask. Cells were incubated for 4-5 days before harvesting virus. For virus harvest, the media was removed from the flask, and 5 mL of cold 25% (w/v) sterile-filtered sucrose was added to the flask. The flask was transferred to –80° C. until the solution was frozen. The flask was then moved to thaw at room temperature, followed by another freeze-thaw cycle. Cell lysates were scraped down, and all cells and sucrose solution were transferred to a sterile-tube and centrifuged at 1100 rpm for 5 minutes. The clarified supernatant containing the hMPV was aliquoted and flash frozen for later use.

hMPV plaque neutralization experiments. LLC-MK2-7.1 cells were maintained in OPTI-MEM® I (Thermo Fisher Scientific) supplemented with 2% fetal bovine serum and grown in 24-well plates at 37° C. in a CO₂ incubator. Two days prior to neutralization assays, 40,000 cells/well were seeded in 24-well plates. On the day of the experiment, serially diluted mAbs isolated from hybridoma supernatants were incubated 1:1 with a suspension of infectious hMPV B2 strain TN/93-32 or hMPV A2 strain CAN/97-83 for 1 hr. Following this, cells were inoculated with 50 μL of the antibody:virus mixture for 1 hr while rocking at room temperature. Cells were then overlaid with 1 mL of 0.75% methylcellulose dissolved in OPTI-MEM® I supplemented with 5 μg/mL trypsin-EDTA and 100 μg/mL CaCl₂. Cells were incubated for 4-5 days after which the cells were fixed with 10% neutral-buffered formalin. The cell monolayers were blocked with 2% nonfat milk supplemented with 2% goat serum for 1 hr. The plates were washed with water, and 200 μL of mouse anti-hMPV N primary antibody (Meridian Biosciences, #C01851M) diluted 1:1000 in the blocking solution was added to each well and incubated for 1 hour. The plates were then washed 3× with water, after which 200 μL of goat anti-mouse IgG-HRP secondary antibody (SE-RACARE® #5220-0286) diluted 1:1000 in blocking solution was added to each well for 1 hr. Plates were then washed 5× with water, and 200 μL of TrueBlue Peroxidase Substrate (SERACARE®) was added to each well. Plates were incubated until plaques were clearly visible. Plaques were counted by hand under a stereomicroscope and compared to a virus-only control, and data was analyzed in Graphpad Prism.

Experimental setup for biolayer interferometry. After obtaining an initial baseline in running buffer (PBS, 0.5% BSA, 0.05% Tween-20, 0.04% thimerosal), 10 μg/mL of his-tagged hMPV F protein was immobilized onto anti-penta-HIS biosensor tips (ForteBio) for biolayer interferometry instrument (OCTET® Red, ForteBio) for 120 s. The baseline signal was measured again for 60 s before biosensor tips were immersed into wells containing 100 μg/mL primary antibody for 300 s. Following this, biosensors were immersed into wells containing 100 μg/mL of a second mAb for 300 s. Percent binding of the second mAb in the presence of the first mAb was determined by comparing the maximal signal of the second mAb after the first mAb was added to the maximum signal of the second mAb alone. mAbs were considered non-competing if maximum binding of the second mAb was ≥66% of its un-competed binding. A level between 33%-66% of its un-competed binding was considered intermediate competition, and <33% was considered competing. For Fab affinity studies, hMPV F protein was loaded as described above, and decreasing concentrations of Fabs were analyzed for binding by associating for 120 s and dissociating for 600 s. Reference wells containing no antibody were subtracted from the data, and affinity values were obtained in OCTET® Data Analysis software.

Mouse experiments. To examine the efficacy of hMPV364, a BALB/c mice model of hMPV infection was utilized. One day prior to virus infection, mice were bled via tail nick for baseline serum collection. Mice were then prophylactically treated 10 mg/kg of MPV364, 10 mg/kg of the isotype-control antibody P19F80, PBS, and one group was untreated. The next day, the MPV364, P19F80, and PBS groups were intranasally inoculated with 100 μL of 10⁵ pfu of hMPV CAN/97-83. Five days following infection, mice were euthanized via 2,2,2-tribromoethanol (Avertin) followed by cervical dislocation, and serum and lungs were collected. Lungs were harvested, homogenized using a GENTLEMACS™ dissociator, flash frozen in liquid nitrogen, and stored at −80° C. until use. Lung viral titers were determined by plaque immunostaining as previously described (Alvarez and Tripp. 2005. J Virol 79:5971-5978). ELISA assays for the mouse serum was conducted using MPV B2 F using the protocol described above.

Example 8

Antibody Recognition of the Human
Metapneumovirus Fusion Protein Trimer Interface hMPV has three surface glycoproteins, the small hydrophobic, the attachment (G), and the fusion (F) proteins. The hMPV F protein is indispensable for hMPV infection, and is highly conserved among hMPV subgroups (Piyaratna et al., *Virus Res.* 160, 200-205 (2011)). Furthermore, the hMPV F protein is the sole target of neutralizing antibodies (Skiadopoulos et al., *Virology* 345, 492-501 (2006)). Although several monoclonal antibodies (mAbs) have previously been isolated that target the hMPV F protein (see, for example, Ulbrandt et al., *J. Virol.* 80, 7799-7806 (2006)), the predominant antigenic sites targeted by the human antibody response are unclear. To define the humoral immune response to the hMPV F protein, two human mAbs, MPV458 and MPV465, were isolated. Both mAbs are neutralizing in vitro and target a unique antigenic site harbored within the trimeric interface of the hMPV F protein. It was determined that both MPV458 and MPV465 have higher affinity for monomeric hMPV F than trimeric hMPV F. MPV458 was co-crystallized with hMPV F to define the molecular footprint of the epitope, and the mAb primarily interacts with an alpha helix on the F2 region of the hMPV F protein. MPV458 also contacts N-linked glycans through the mAb light chain.

hMPV and respiratory syncytial virus (RSV) share the Pneumoviridae virus family, and a similar F protein that has approximately 30% homology between the two viruses. For both viruses, the F protein has two long-lived conformations, the pre-fusion and post-fusion states (Huang et al., *Front. Immunol.* doi.org/10.3389/fimmu.2019.02778 (2019)). Both RSV and hMPV lacking the G protein can infect cells in vitro, although these viruses are attenuated in vivo (Biacchesi et al., *J. Virol.* 78, 12877-12887 (2004)). The pre-fusion conformation of the F protein is meta-stable, and stabilized versions of both hMPV F (Battles et al., *Nat. Commun.* 8, 1528 (2017)) and RSV F (McLellan et al., *Science* (80-.). 342, 592-598 (2013); Krarup et al., *Nat. Commun.* 6, 8143 (2015)) have been generated, although the pre-fusion hMPV F protein has not been stabilized for routine HEK293F or CHO cell line expression. For RSV F, the pre-fusion conformation contains antigenic sites $\emptyset^{19}$ and $V^{20}$ located on the head of the F protein, which elicit the most potent neutralizing antibodies as compared to the post-fusion conformation (Gilman et al., *Sci. Immunol.* 1, 1-12 (2016); Mousa et al., *Nat. Microbiol.* 2, 16271 (2017)). Furthermore, the human antibody response to RSV infection is primarily focused on these pre-fusion-specific epitopes (Ngwuta et al., *Sci. Transl. Med.* 7, 309ra162 (2015)). For hMPV F, data using human serum has shown that the preponderance of hMPV F-specific human antibodies bind both pre-fusion and post-fusion F conformations (Battles et al., 2017, supra). Similar to other respiratory pathogens, children, the elderly, and the immunocompromised are the major groups for which hMPV infection may require hospitalization (see, for example, Panda et al, *Int. J. Infect. Dis.* 25, 45-52 (2014)).

The hMPV F protein contains a single site that is cleaved to convert the polypeptide $F_0$ protein into the meta-stable disulfide-linked $F_1$-$F_2$ pre-fusion homotrimer. This is different than RSV F, which contains two furin cleavage sites flanking the p27 peptide fragment. The cleavage enzyme for hMPV F in vivo is unknown, although cleavage can be accomplished by trypsin in vitro (Schowalter et al., *J. Virol.* 80, 10931-10941 (2006)). X-ray crystal structures of the hMPV F protein from the A1 subgroup have been determined in the pre-fusion and post-fusion conformations (Más et al., *PLoS Pathog.* 12, e1005859 (2016); Battles et al., 2017, supra). A panel of rodent-derived mAbs was initially used to map the neutralizing epitopes on the hMPV F protein using viral escape mutants (Ulbrandt et al., *J Virol.* 80, 7799-7806 (2006); Ulbrandt et al., *J. Gen. Virol.* 89, 3113-3118 (2008)). The known antigenic sites on the hMPV F protein include antigenic sites III, IV, and an unnamed site targeted by mAb DS7 (Huang et al., *Front. Immunol.* doi.org/10.3389/fimmu.2019.02778 (2019)). DS7 was isolated from a human phage display library (Williams et al., *J. Virol.* 81, 8315-8324 (2007)), and was co-crystallized with a fragment of the pre-fusion hMPV F protein (Wen et al., *Nat. Struc. Mol. Biol.* 19, 461-463 (2012)). Several isolated mAbs have been found to cross-neutralize RSV and hMPV, including MPE8 (Corti et al., *Nature* 501, 439-43 (2013)) and 25P13 (Wen et al., *Nat. Microbiol.* 2, 16272 (2017).) (site III), and 101F (Mas et al., *PLoS Pathog.* 12, e1005859 (2016)), 54G10 (Schuster et al., *J. Infect. Dis.* 211, 1-34 (2014)), and 17E10 (Mousa et al., *PLoS Pathog.* 14, e1006837 (2018)) (site IV). As disclosed above, MPV364, competes for binding at antigenic site III, but does not cross-react with RSV F. Two additional human mAbs were isolated to further identify the epitopes on the hMPV F protein recognized by the human immune system.

Two new human antibodies were isolated from healthy adult donors by screening against the hMPV B2 F protein (Table S1) expressed in HEK293F cells (Bar-Peled et al., *J. Virol.* doi:10.1128/JVI.00342-19 (2019) doi:10.1128/jvi.00342-19).

TABLE S1

| Properties of hMPV F recombinant protein constructs used in this study. | | | | | |
|---|---|---|---|---|---|
| Construct name | Subgroup | Strain | Size Major conformation | Cleavage site | Trimerization domain |
| hMPV A1 F | A1 | NL/1/00 | Monomer | KKRKRR (SEQ ID NO: 69) | Foldon |
| hMPV A2F | A2 | NL/17/00 | Monomer | KKRKRR (SEQ ID NO: 69) | Foldon |

TABLE S1-continued

Properties of hMPV F recombinant protein constructs used in this study.

| Construct name | Subgroup | Strain | Size Major conformation | Cleavage site | Trimerization domain |
|---|---|---|---|---|---|
| hMPV B1 F | B1 | NL/1/99 | Monomer | KKRKRR (SEQ ID NO: 69) | Foldon |
| hMPV B2 F | B2 | NL/1/94 | Monomer | KKRKRR (SEQ ID NO: 69) | Foldon |
| hMPV 130-BV | A1 | NL/1/00 | Trimer Pre-fusion | RQSR (SEQ ID NO: 70) | Foldon |
| hMPVB2F-GCN4 | B2 | TN/99-419 | Trimer Pre-fusion | RQSR (SEQ ID NO: 70) | GCN4 |
| hMPVB2F-GCN4 dFP 6R | B2 | TN/99-419 | Trimer Post-fusion | RRRRRR (SEQ ID NO: 71) | GCN4 |

MPV458 and WIV465 were isolated from two different donors, and have isotypes of $IgG_3$ and kappa, and $IgG_1$ and lamda, respectively. WIV458 utilizes $V_H3$-30, $J_H3$, $D_H2$ $V_K1$-33, and $J_K5$, while MPV465 utilizes $V_H3$-33, $J_H5$, $D_H3$-22, $V_L$-47, and $J_L3$. The CDR3 loops differ dramatically between the two antibodies as WIV458 is just eight amino acids, while WIV465 has a 21 amino acid long CDR3 loop (Table S2)

TABLE S2

IMGT V-QUEST Analysis of MPV458 and MPV465.

| Gene | MPV458 IgG3/kappa | MPV465 IgG1/lambda |
|---|---|---|
| $V_H$ % identity | IGHV3-30*03 IGHV3-30*18 IGHV3-30-5*01 89.6% | IGHV3-33*01 IGHV3-33*06 IGHV3-33*07 90.3% |
| $D_H$ | IGHD2-2*01 | IGHD3-22*01 |
| $J_H$ % identity | IGHJ3*01 IGHJ3*02 87.8% | IGHJ5*02F 90.2% |
| $V_L$ | IGKV1-33*01 IGKV1D-33*01 94.3% | IGLV1-47*02 F 95.6% |
| $J_L$ | IGKJ5*01 F 89.5% | IGLJ3*02 97.1% |
| CDR-H1 | GFDFSRYG (SEQ ID NO: 53) | GFTFGTYG (SEQ ID NO: 63) |
| CDR-H2 | IVYAGSNK (SEQ ID NIO: 54) | IWLDGSKT (SEQ ID NO: 64) |
| CDR-H3 | ARDQAFDL (SEQ ID NO: 55) | ARAPGSVWYDTRGHMKGWFDP (SEQ ID NO: 65) |
| CDR-L1 | QGISRS (SEQ ID NO: 56) | SSNIENNY (SEQ ID NO: 66) |
| CDR-L2 | DAS (SEQ ID NO: 57) | GDN (SEQ ID NO: 67) |
| CDR-L3 | QQYDNLRIS (SEQ ID NO: 58) | ATWDDNLSGPV (SEQ ID NO: 68) |

To identify the antigenic epitopes targeted by the isolated mAbs, epitope binning was performed using competitive biolayer interferometry (Mousa et al., *PNAS* 113, E6849-E6858 (2016). Previously discovered mAbs with known antigenic epitopes were utilized as mapping controls, including mAbs 101F (Wu et al., *J. Gen. Virol.* 88, 2719-2723 (2007)) (site IV), MPV196 (Bar-Peled et al., *J. Virol.* doi: 10.1128/JVI.00342-19 (2019) doi:10.1128/jvi.00342-19) and DS7 (Williams et al., *J. Virol.* 81, 8315-8324 (2007)) (DS7 epitope), and MPE8 (Corti et al., *Nature* 501, 439-43 (2013).) and MPV364 (Bar-Peled et al., 2019, supra) (site III) (FIG. 7A). Anti-penta-HIS biosensors were loaded with the hMPV 130-BV F (Battles et al., 2017, supra) protein and then loaded with one hMPV F-specific mAb, followed by exposure to a second mAb. mAbs MPV458 and MPV465 did not compete with any of the mapping control mAbs, yet competed for binding with each other, suggesting these two mAbs bind to a unique antigenic site on the hMPV F protein.

Figure 7B:
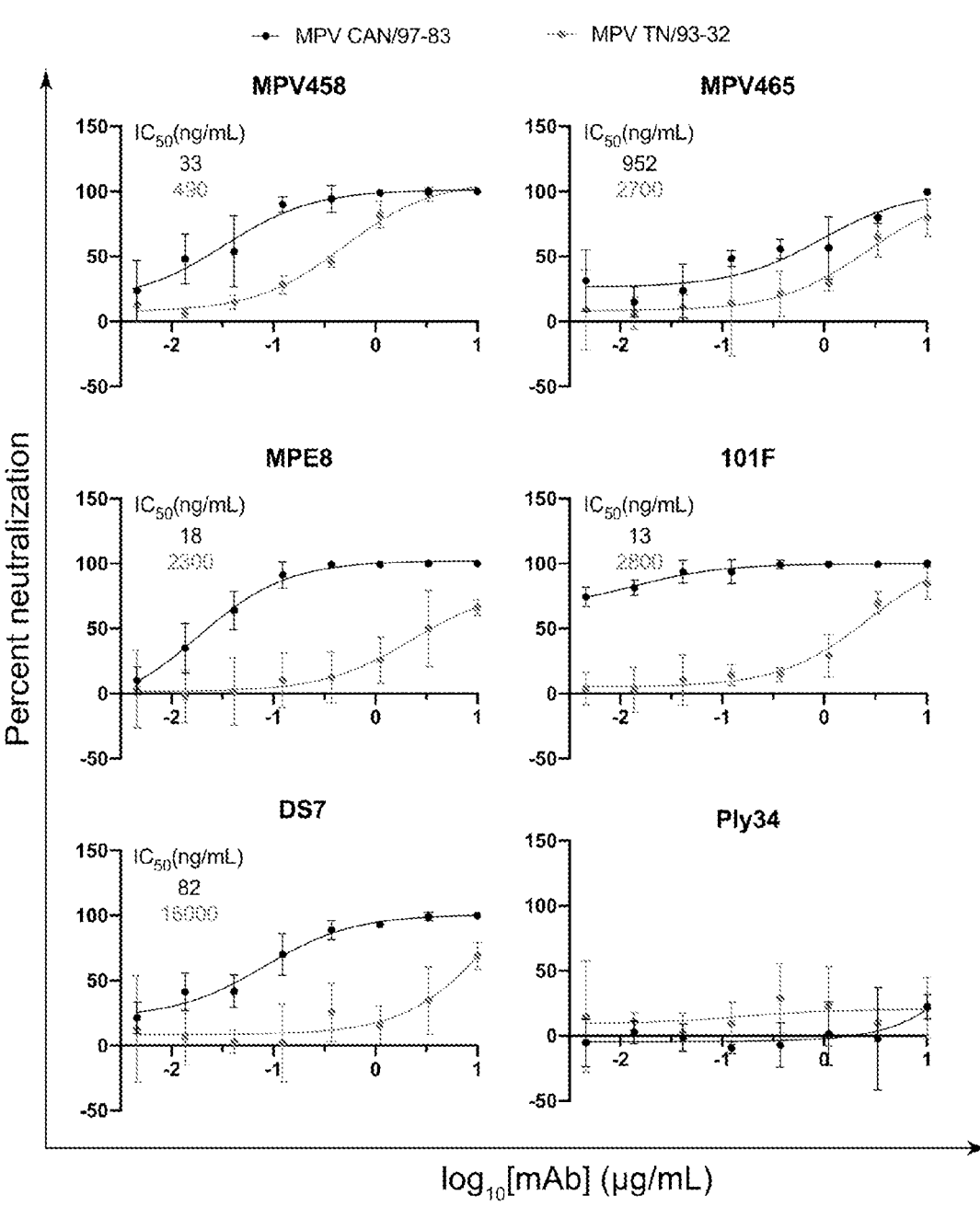
Figure 7C:
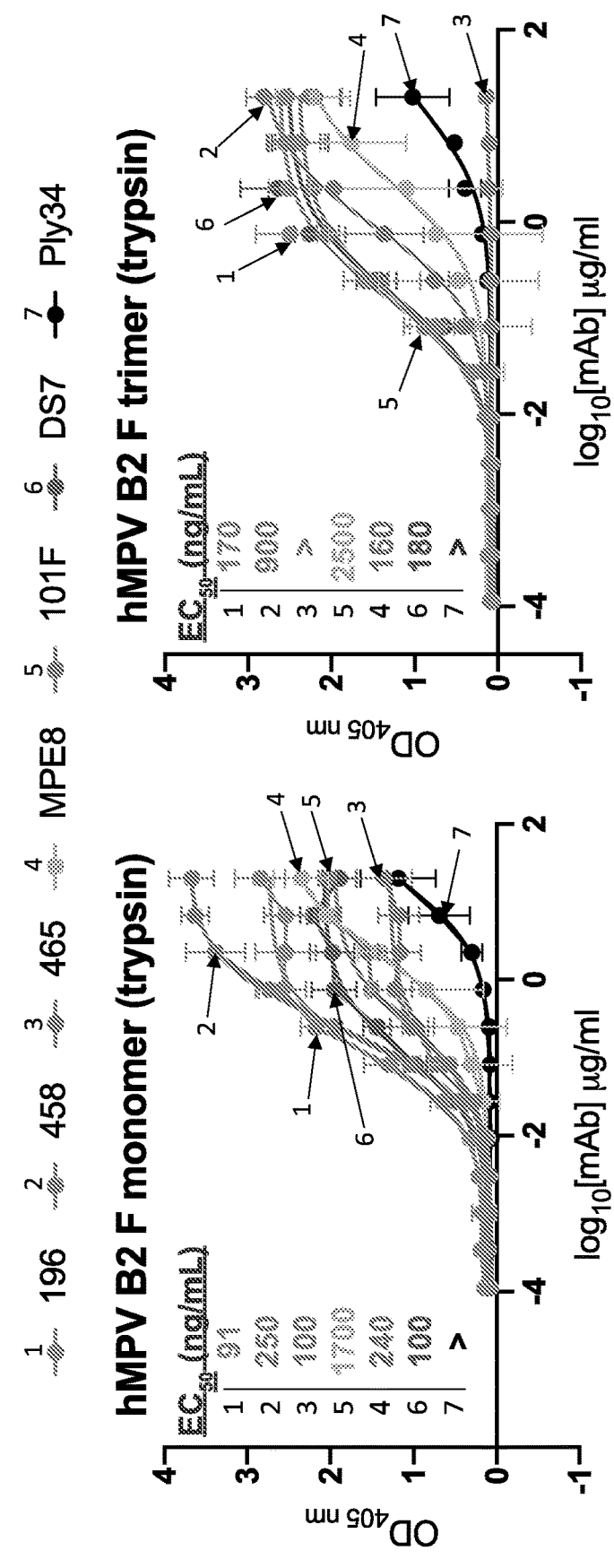
Figure 7D:
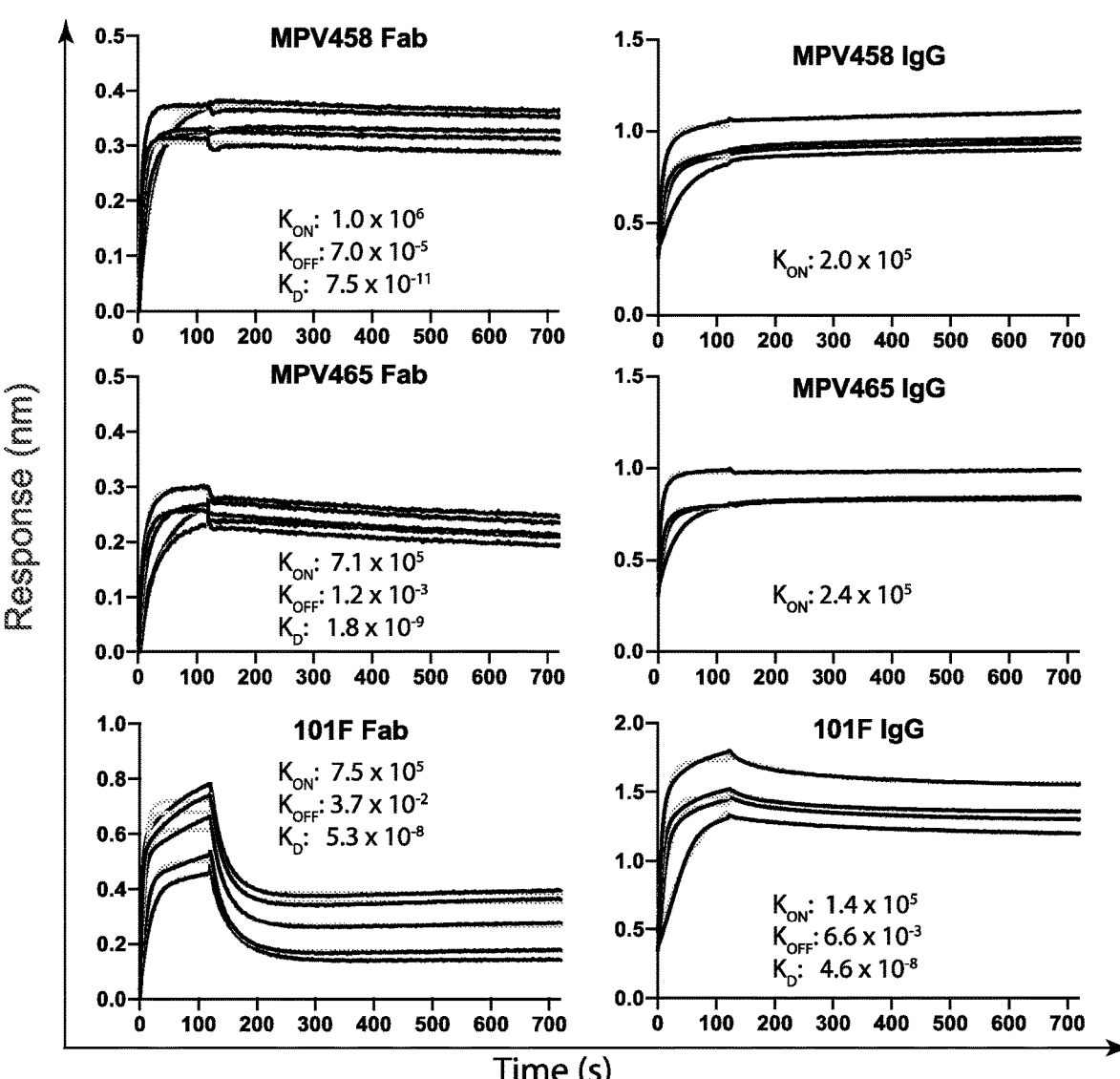
Figure 14:
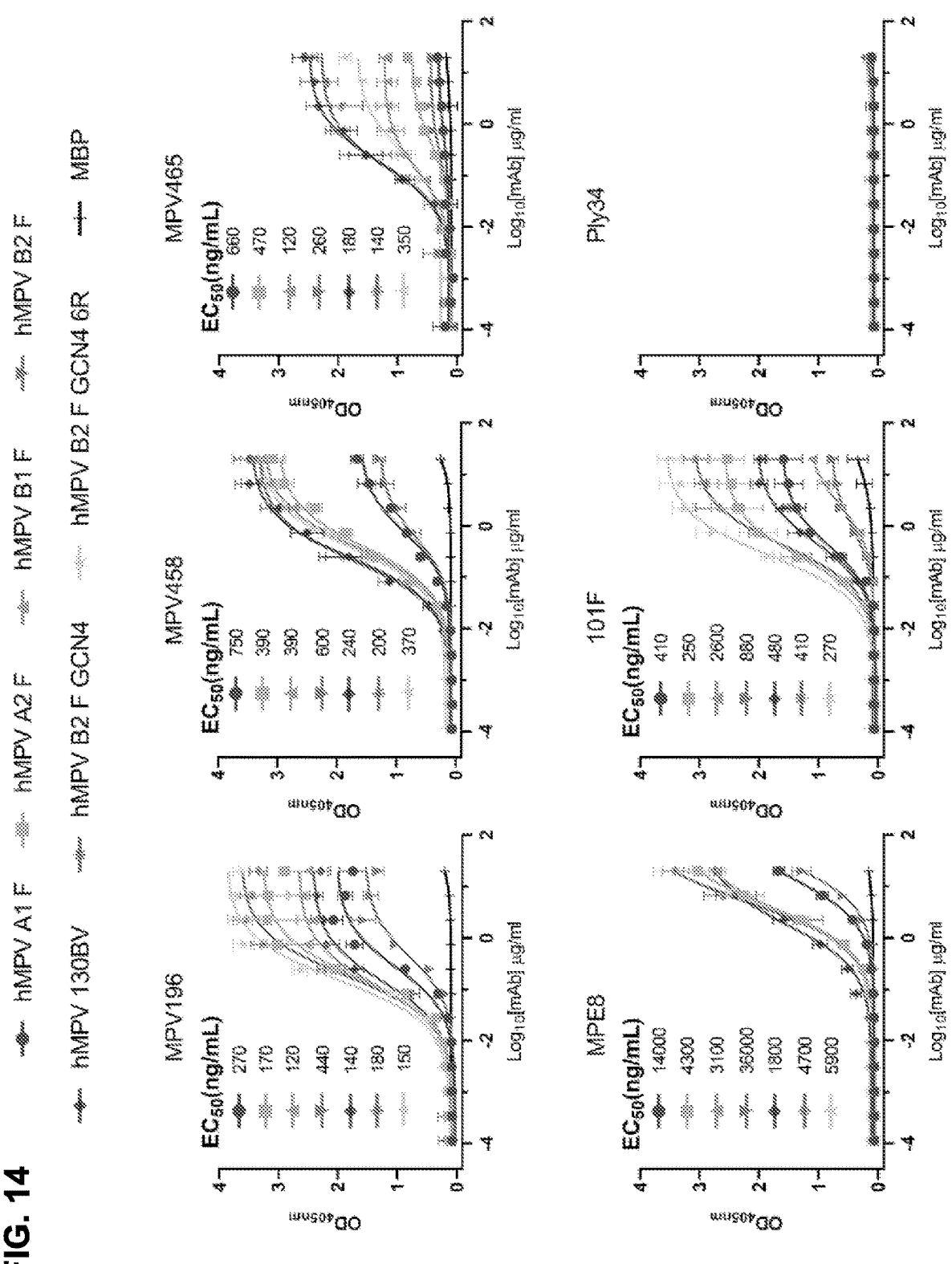
FIG. 14. ELISA binding curves of the hMPV F protein-specific mAbs to a panel of hMPV F protein constructs from multiple subgroups. MPV458 and MPV465 bind to hMPV F proteins from all four subgroups. $EC_{50}$ values are inlaid in each graph. Binding curves and $EC_{50}$ values are colored according to the legend. Data points are the average of four replicates and error bars are 95% confidence intervals. > indicates signal above 0.5 absorbance units was not detected at the highest concentration of 20 µg/mL.

Plaque neutralization assays were performed to determine the neutralization properties of MPV458 and MPV465 against hMPV subgroup B2 (strain TN/93-32) and hMPV subgroup A2 (strain CAN/97-83) in vitro (FIG. 7B). MPV458 neutralized hMPV with 50% inhibitory concentration (IC$_{50}$) values of 33 ng/mL for MPV CAN/97-83 and 490 ng/mL for MPV TN/93-32, while MPV465 had IC$_{50}$ values of 950 and 2700 ng/mL, respectively. The neutralization potency of MPV458 was comparable to mAbs MPE8 and 101F. The binding properties of MPV458 and MPV465 were determined by ELISA and biolayer interferometry. For ELISA, the half-maximal effective concentration (EC$_{50}$) values were used to quantify binding between mAbs across multiple hMPV F protein constructs (Table S1, FIG. 10-13). Generating trimeric hMPV F can be achieved by treating purified protein with trypsin as previously described (Más et al., 2019, supra; Bar-Peled et al., 2019, supra) although this process generates batch to batch variation of both pre-fusion and post-fusion conformations. Both mAbs bind to hMPV F proteins from all four hMPV F subgroups (FIG. 14). Binding to hMPV F constructs that were predominantly in the pre-fusion and post-fusion conformations (FIG. 14) was assessed. No major differences were observed between the predominantly pre-fusion hMPV F 130-BV protein and the predominantly post-fusion hMPV B2 GCN4 6R F protein, indicating these mAbs bind both pre-fusion and post-fusion conformations. Binding to exclusively monomeric and trimeric hMPV B2 F proteins that were treated with trypsin to induce cleavage (FIG. 7C) was also assessed. Both mAbs MPV458 and MPV465 had stronger binding to monomeric hMPV F than trimeric hMPV F. MPV458 had a nearly four-fold lower EC$_{50}$ to monomeric hMPV B2 F than trimeric hMPV B2 F, while MPV465 binding was completely abrogated binding to the hMPV B2 F trimer, yet bound well to the hMPV B2 F monomer. These data indicate the epitope for MPV458 and MPV465 is predominantly exposed on monomeric hMPV F. Binding avidity and affinity were assessed by biolayer interferometry using the predominantly pre-fusion hMPV 130-BV protein (FIG. 7D). Affinity measurements were completed by cleaving mAbs to Fab fragments. MPV458 Fab had a faster K$_{ON}$ than MPV465 Fab and 101F Fab, and also had limited dissociation, which gave a K$_D$ 2-logs higher than MPV458 and 3-logs higher than 101F. Limited dissociation was observed for MPV458 and MPV465 IgG molecules as compared to 101F IgG, and a K$_{OFF}$ rate was not obtained. Overall, these data indicate MPV458 has higher affinity for the hMPV 130-BV F protein than mAbs MPV465 and 101F.

Figure 15:
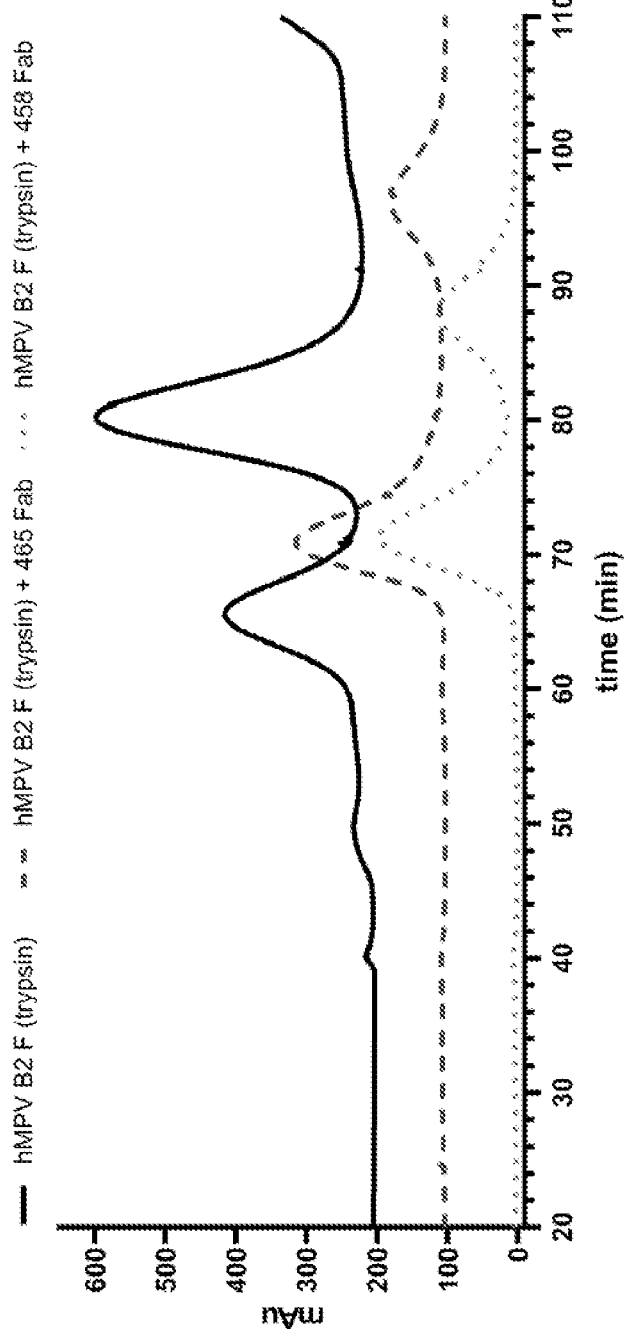
FIG. 15. Chromatograms of size exclusion chromatography of hMPV B2 F and hMPV B2 F+Fab complexes. Trypsinization of hMPV B2 F generates homogeneous trimeric and monomeric peaks. Complexing trimeric hMPV B2 F with Fabs of MPV458 or MPV465 generates monomeric F-Fab complexes and excess Fabs. Data are representative of at least two independent experiments.

To fully define the epitope targeted by the newly isolated mAbs, the Fab of MPV458 was co-crystalized in complex with hMPV B2 F. Trypsinization of hMPV B2 F generated trimeric and monomeric versions of hMPV F as assessed by size exclusion chromatography (FIG. 15). Cleavage of MPV458 and MPV465 mAbs to Fab fragments and subsequent addition of these Fabs with trypsinized trimeric hMPV B2 F resulted in monomeric hMPV F-Fab complexes (FIG. 15). Although the hMPV B2 F trimer appeared to fall apart upon Fab binding, this could not be attributed to binding of MPV458 and MPV465 as other Fabs also caused trimer dissociation of this construct. The MPV458-hMPV B2 F complex was subjected to crystallization screening and crystals were obtained in 0.5 M ammonium sulfate, 0.1 M sodium citrate tribasic dihydrate pH 5.6, and 1.0 M Lithium sulfate monohydrate. Crystals were harvested and X-ray diffraction data was collected, and the structure of the complex was determined to 3.1 Å (FIGS. 8A-8D, Table S3).

TABLE S3

| Data collection and refinement statistics. | |
|---|---|
| | hMPV B2 F + MPV458 Fab |
| Wavelength | 1.000 Å |
| Resolution range | 41.05-3.1 (3.211 -3.1) |
| Space group | P 65 |
| Unit cell | 128.489 128.489 188.352 90 90 120 |
| Total reflections | 671484 (67401) |
| Unique reflections | 31943 (3223) |
| Multiplicity | 21.0 (20.9) |
| Completeness (%) | 99.91 (100.00) |
| Mean I/sigma(I) | 17.62 (1.58) |
| Wilson B-factor | 107.39 |
| R-merge | 0.1407 (2.188) |
| R-meas | 0.1443 (2.243) |
| R-pim | 0.03155 (0.4889) |
| CC1/2 | 0.999 (0.621) |
| CC* | 1 (0.875) |
| Reflections used in refinement | 31931 (3223) |
| Reflections used for R-free | 3241 (350) |
| R-work | 0.1897 (0.3470) |
| R-free | 0.2339 (0.4018) |
| CC(work) | 0.960 (0.680) |
| CC(free) | 0.958 (0.511) |
| Number of non-hydrogen atoms | 6265 |
| macromolecules | 6190 |
| ligands | 75 |
| Protein residues | 818 |
| RMS(bonds) | 0.011 |
| RMS(angles) | 1.26 |
| Ramachandran favored (%) | 92.82 |
| Ramachandran allowed (%) | 6.93 |
| Ramachandran outliers (%) | 0.25 |
| Rotamer outliers (%) | 0.00 |
| Clashscore | 11.10 |
| Average B-factor | 100.80 |
| macromolecules | 100.36 |
| ligands | 137.75 |

Statistics for the highest-resolution shell are shown in parentheses.

Figures 8A, 8B, 8C, 8D:
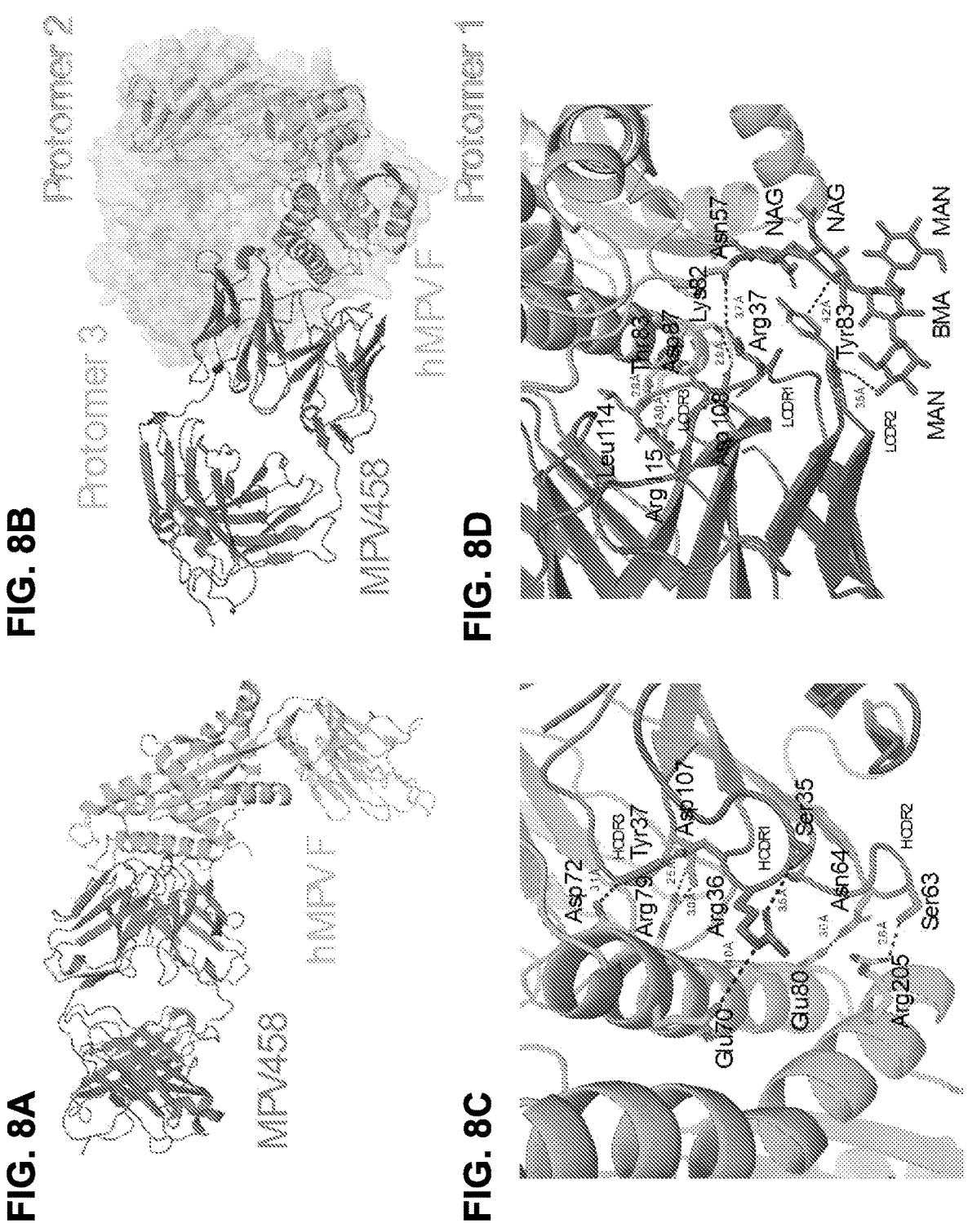
FIGS. 8A-8D X-ray crystal structure of the hMPV B2 F+MPV458 Fab complex. (A) The asymmetric unit of the complex is displayed. Monomeric hMPV B2 F co-crystallized with one Fab of MPV458. (B) Overlay of the hMPV B2 F+MPV458 Fab complex with the previously determined X-ray crystal structure of hMPV A1 F in the pre-fusion conformation (PDB: 5WB0). The hMPV F protein from each structure were overlaid in PyMol. MPV458 clashes with the trimeric structure. (C) Hydrogen bonding events observed with the MPV458 heavy chain. (D) Hydrogen bonding events observed with the MPV458 light chain. The MPV458 light chain also interacts with an extended glycan patch linked from Asn57.
Figure 16:
FIG. 16. Symmetry-related partners in the hMPV B2 F+MPV458 Fab complex. No trimeric structure was observed for the hMPV F protein.
Figure 17:
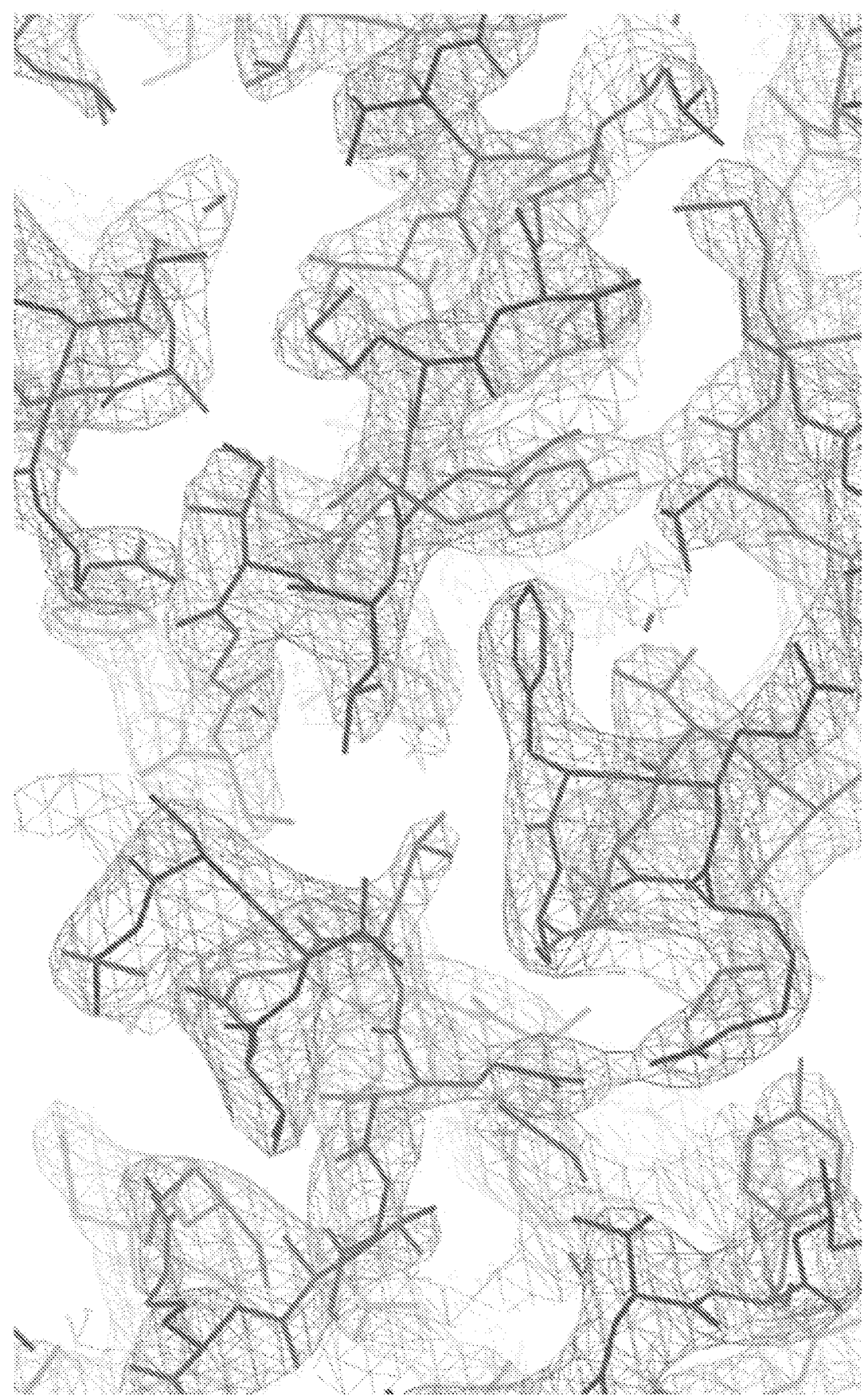
FIG. 17. Representative image of the electron density map surrounding the hMPV B2 F+MPV458 X-ray crystal structure. The image was made in COOT and the map level rmsd is set to 2.45.
Figure 18:
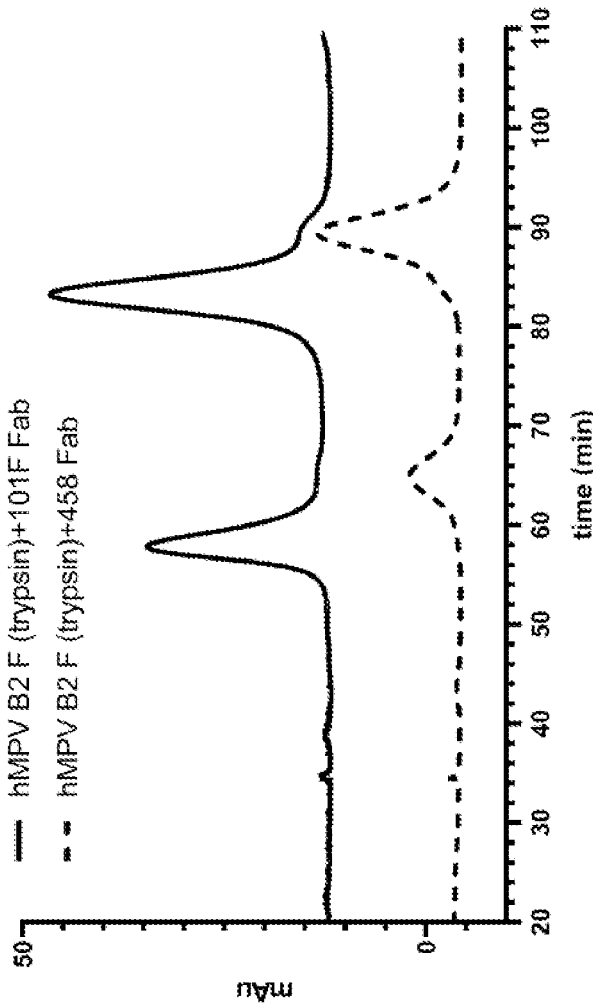
FIG. 18. Chromatographs from size exclusion chromatography of post-fusion hMPV B2 F in complex with 101F and MPV458. No complexes were observed with MPV458, while 101F readily formed complexes with hMPV F.
Figure 20A:
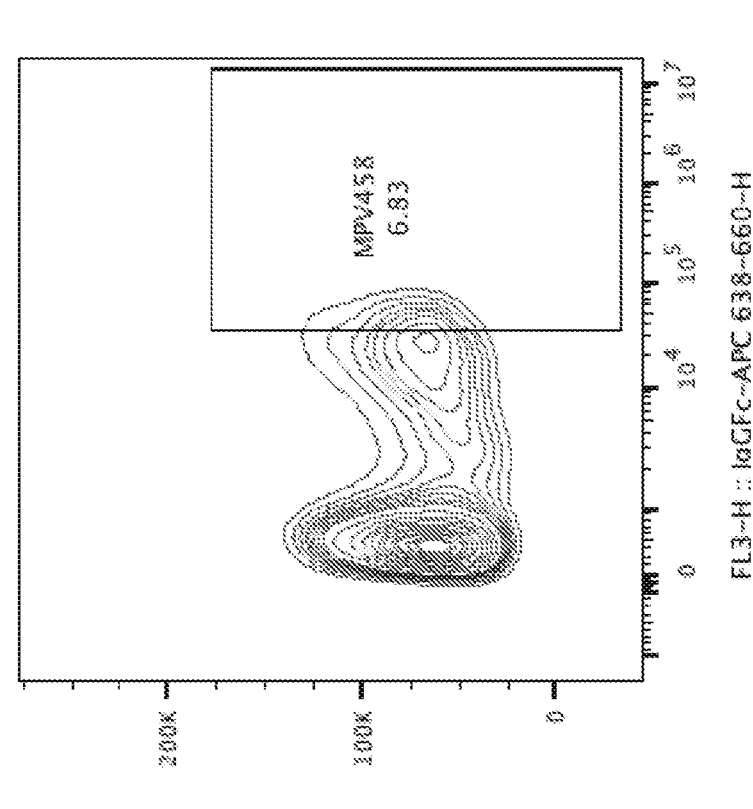
Figure 20C:
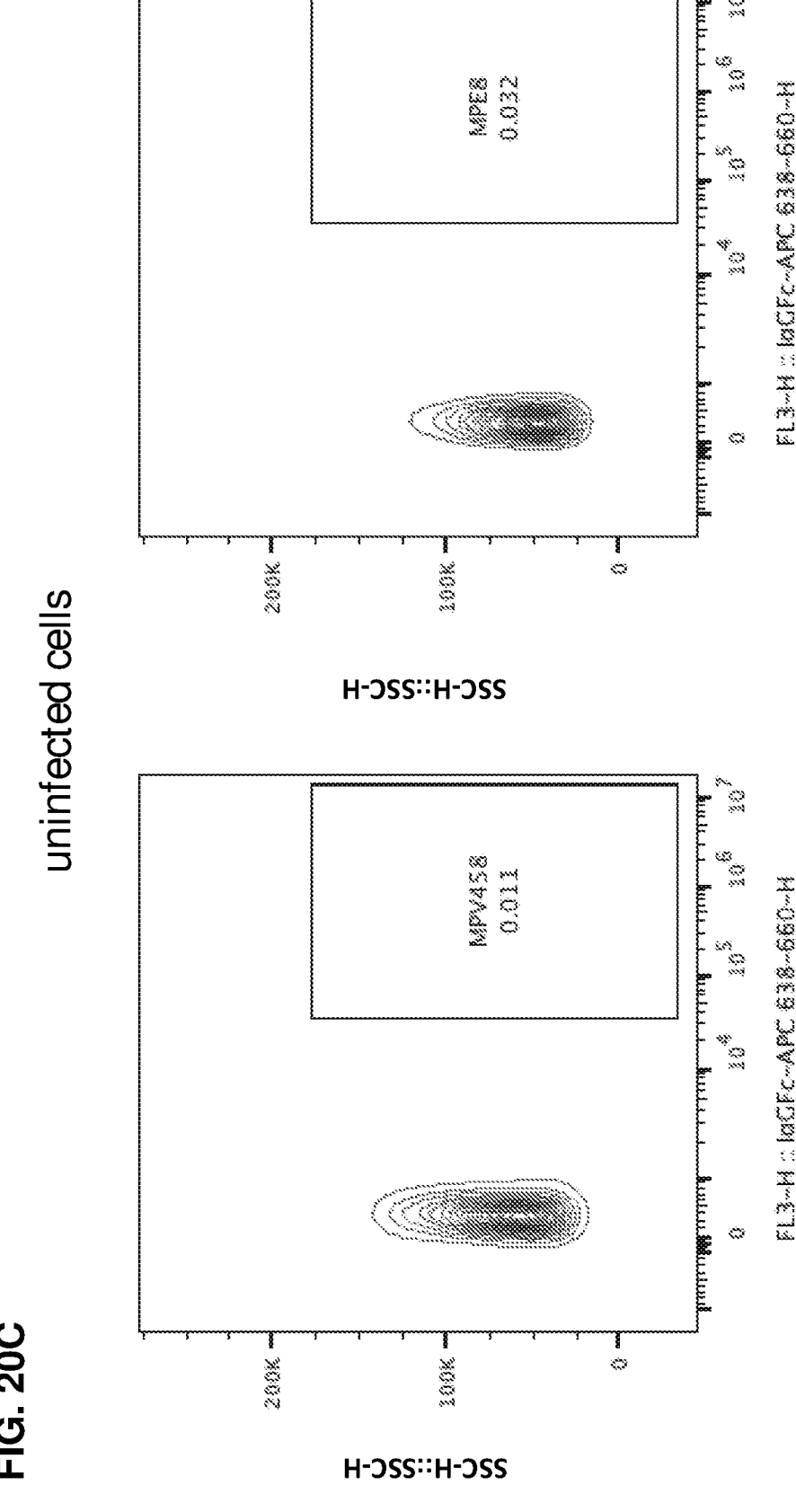

The asymmetric unit contained one hMPV F protomer with one MPV458-Fab molecule. hMPV F was observed in the pre-fusion conformation, although no trimeric structure was observed when viewing symmetry related partners (FIG. 16). MIPV458 targets a unique epitope compared to previously discovered Pneumovirus antigenic sites. The primary epitope consists of a single alpha helix of amino acids 66-87 of the F2 region (FIG. 8A). Compared to the hMPV F protein, MPV458 sits nearly perpendicular to the long axis of the F protein. Upon overlay with the previously determined X-ray crystal structure of pre-fusion hMPV F, it is clear the major epitope lies completely within the interface between two protomers of trimeric hMPV F (FIG. 81B). This unusual epitope suggests the hMPV F protein is partially monomeric on the surface of the virion envelope or infected cells, or substantial breathing of the hMPV F protein takes place to allow the antibody to bind and neutralize the virus. As mentioned earlier, MPV458 has an unusually short HCDR3 loop of just 8 amino acids. The HCDR3 and LCDR3 are centered on the 66-87 helix region. Numerous hydrogen bonding events are clear in the electron density (FIGS. 8C, 8D, 17). The HCDR3 interacts via Asp107 with Arg79 of hMPV F, while HCDR2 Asn64 and Ser63 interact with Glu80 and Arg205, respectively (FIG. 8C). The HCDR1 utilizes Arg36 to interact with Glu70. The light chain LCDR3 has more hydrogen bonding events than the HCDR3, utilizing the backbone amino group of Leu114 to interact with Thr83, Arg115 hydrogen bonds to Asp87, and Asp108 bonds to Lys82 (FIG. 8D). LCDR1 Arg37 interacts with Asn57, which has an extended N-linked glycan motif. The LCDR2 Asp56 interacts with Lys75. A non-CDR loop of light chain interacts with the glycan motif consisting of NAG-NAG-BMA with branched MAN residues off the BMA glycan, in which Tyr83 interacts with the extended MAN glycan, while the long-face of Tyr83 site parallel to the extended glycan, suggesting a favorable interaction with the glycan motif.

Figures 9A, 9B, 9C, 9D, 9E:
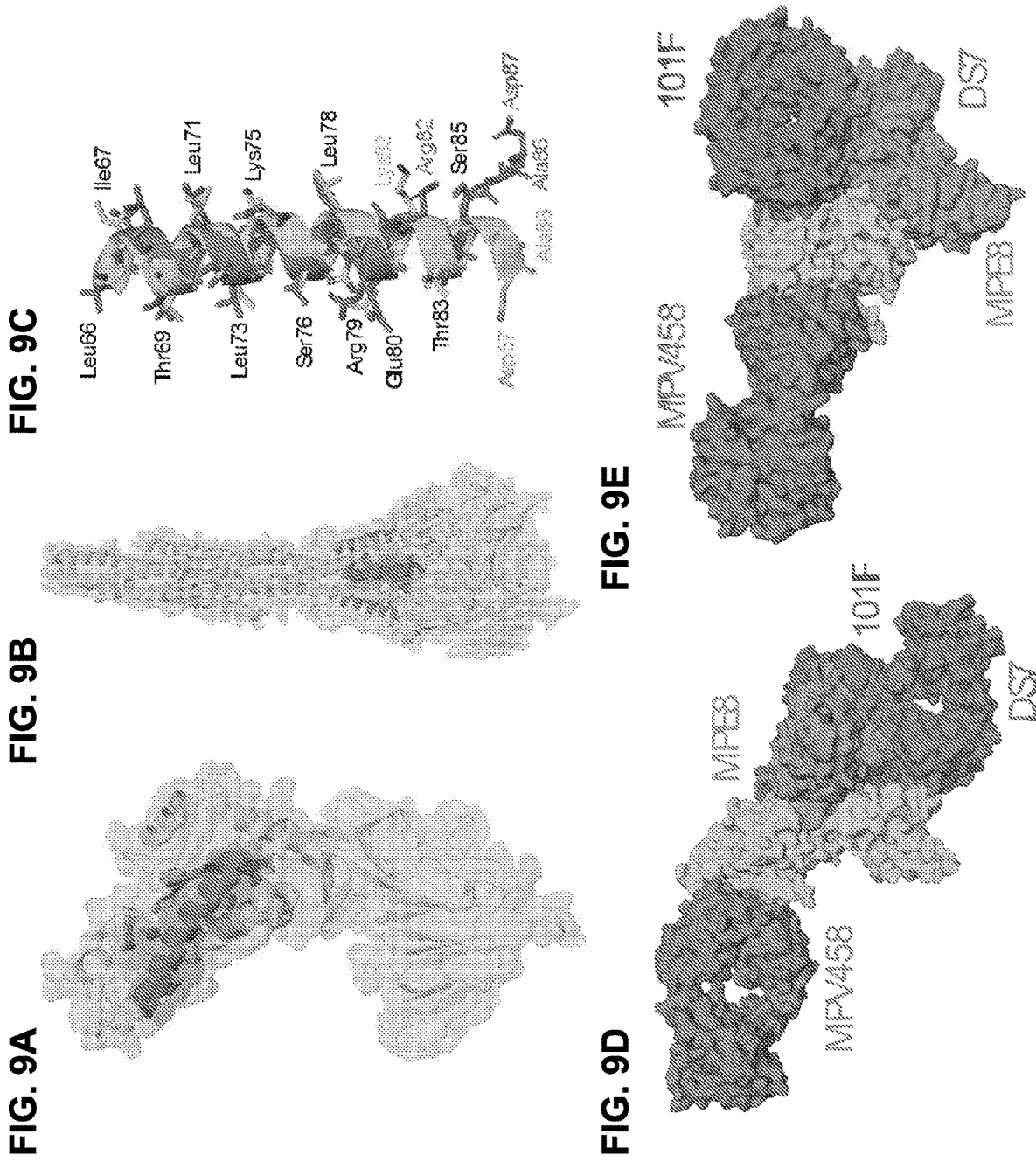
FIGS. 9A-9E. Structural comparison of the hMPV B2 F+MPV458 complex. (A) The X-ray crystal structure of pre-fusion hMPV F is shown with the 66-87 epitope (LIK-TELDLTKSALRELKTVSAD, SEQ ID NO: 72) (PDB ID: 5WB0). (B) The corresponding 66-87 epitope is colored on the X-ray crystal structure of post-fusion hMPV F (5L1X). The 66-87 epitope is surface exposed on trimeric post-fusion hMPV F. (C) Structural overlay of the 66-87 region between pre-fusion (cyan) hMPV F from the hMPV B2 F+MPV458 complex and post-fusion hMPV F (PDB ID: 5L1X). Conserved amino acid residues between the B2 and A1 subgroups are listed in black, while residues that have mutations or shift positions are colored according to the corresponding structure. (D) Structural overlay of MPV458 on the hMPV F protein with previously structurally characterized hMPV F-specific mAbs. MPE8 (site III) and 101F (site IV) were aligned onto hMPV F by aligning the corresponding RSV F residues onto hMPV F from the co-complex structures with RSV F (PDB ID: 5U68 and PBD ID: 3045). DS7 was aligned from PDB 4DAG. (E) The structure overlay in (D) is rotated 90 degrees to view the hMPV F protein from the head.
Figure 10:
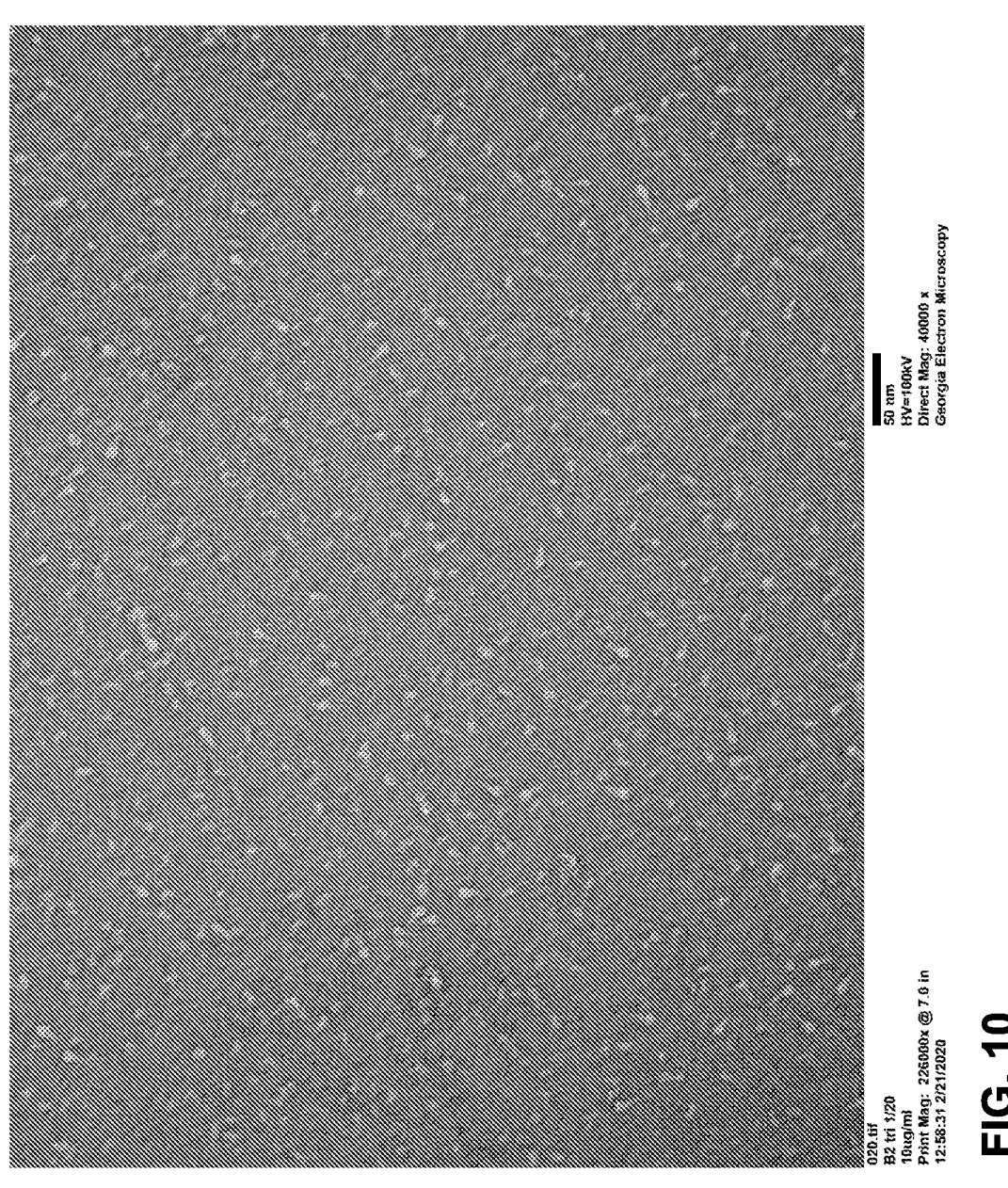
FIG. 10. Negative-stain electron micrograph of purified hMPV B2 F prior to treatment with trypsin. A mixture of pre-fusion trimers, post-fusion trimers, and monomeric protein was observed.
Figure 11:
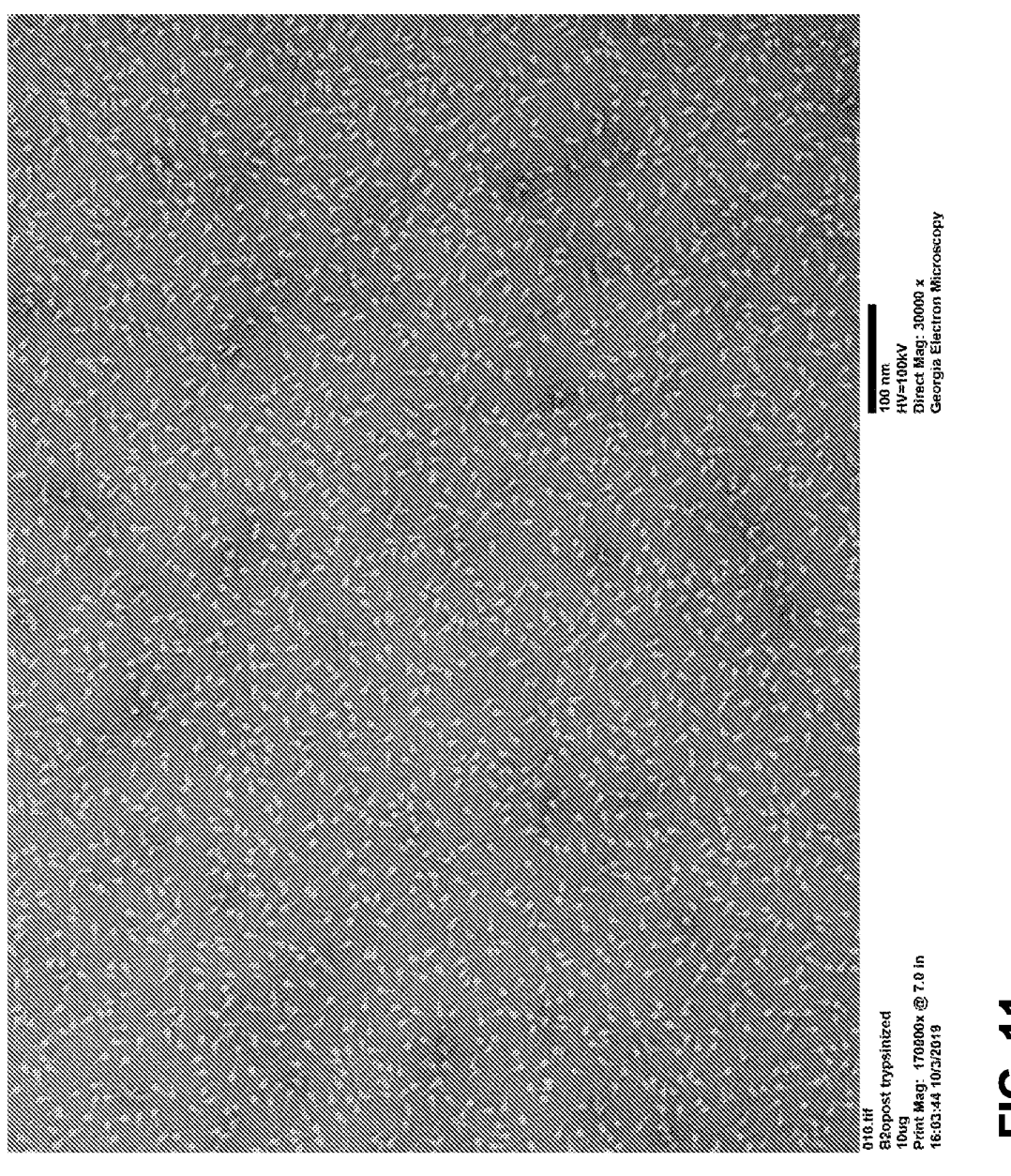
FIG. 11. Negative-stain electron micrograph of hMPV B2 F after treatment with trypsin. Trimeric protein was purified by size exclusion chromatography before being subjected to negative-stain electron microscopy.
Figure 12:
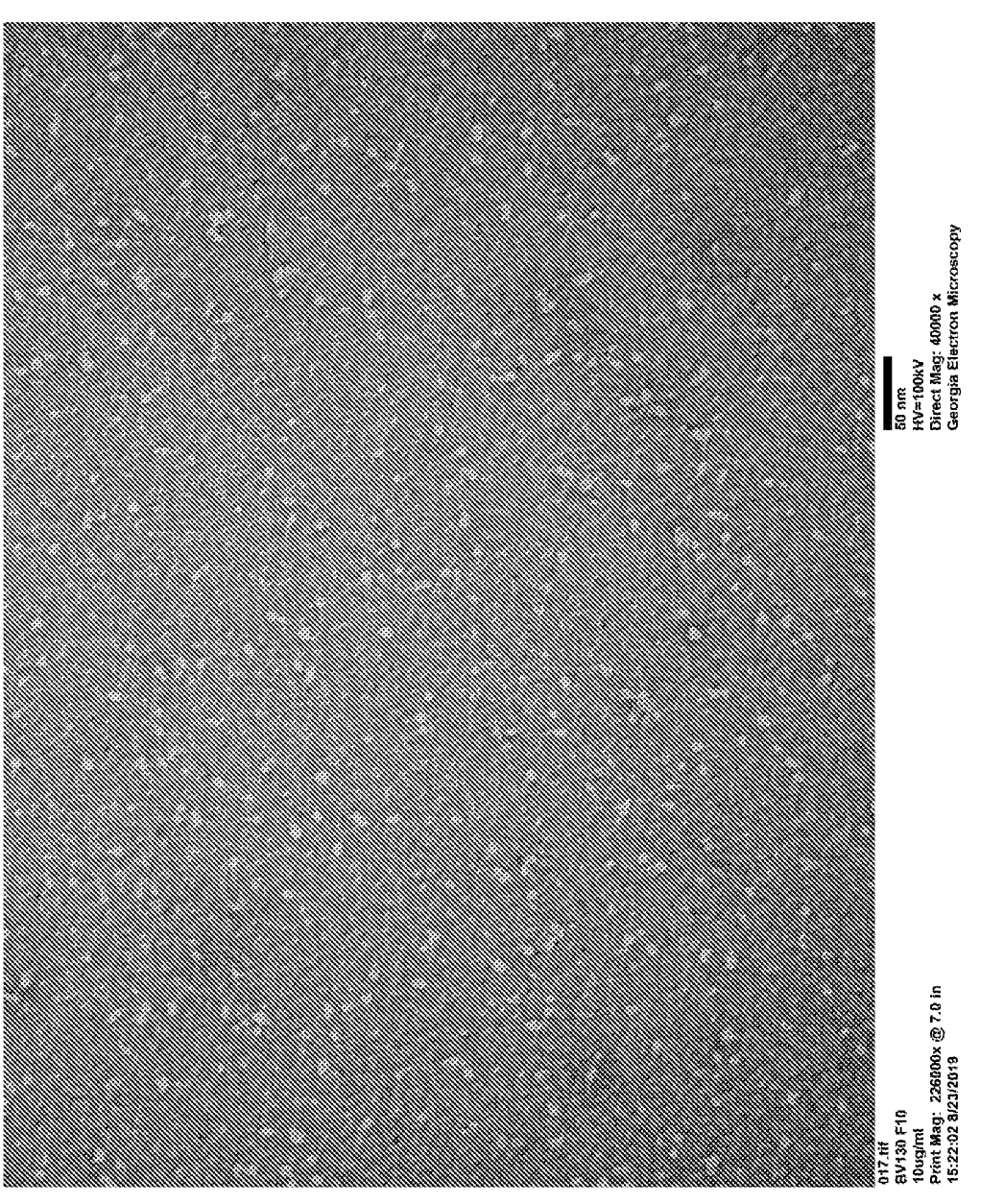
FIG. 12. Negative-strain electron micrograph of the hMPV 130-BV F protein. The protein predominantly resembles the pre-fusion F conformation.
Figure 13:
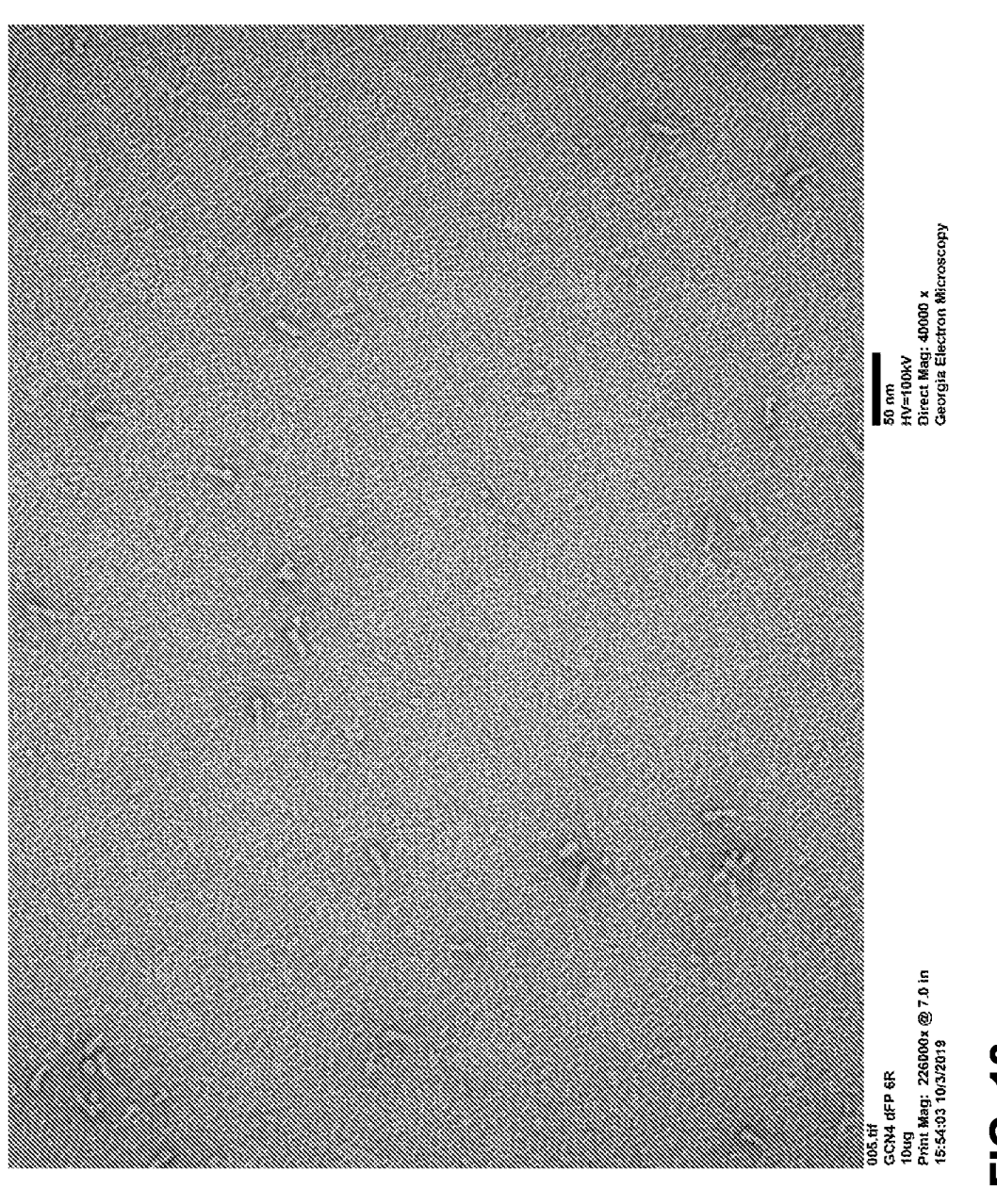
FIG. 13. Negative-strain electron micrograph of the hMPV B2 F-GCN4 dFP 6R protein. The protein contains an extended cleavage site incorporating six repeating Arg residues to enhance intracellular cleavage. The protein predominantly resembles the post-fusion conformation.

The 66-87 helix of hMPV F is structurally conserved in the pre-fusion and post-fusion conformations, although the helix is exposed on the outer surface in the trimeric post-fusion conformation (FIGS. 9A, 9B). Upon overlay of the 66-87 region of the pre-fusion and post-fusion hMPV F proteins, residues 66-83 align well, while the helix breaks on post-fusion hMPV F at residues 84-87 (FIG. 9C). This sequence identity of the helix is highly conserved, as residues are identical between the A1 and B2 subgroups, except for a Lys82/Arg82 mutation. As MPV458 and MPV465 exhibited binding to post-fusion hMPV F constructs, binding was further examined by attempting to generate a complex between the Fab of MPV458 and trypsinized hMPV B2 F that was in the post-fusion conformation (FIG. 11, 18). No complex was observed as assessed by size exclusion chromatography while the Fab of 101F formed a complex with the post-fusion hMPV F protein. This suggests that although binding is observed by ELISA, the complete epitope lies outside the 66-87 helix and is incomplete in the post-fusion conformation. Since the major epitope is focused on the single helix, binding was assessed by Western blot to determine if MPV458 displayed binding to a linear conformation in the denatured hMPV F protein (FIG. 19). Binding to hMPV B2 F was analyzed using reduced and heated protein, and a nonreduced protein. MPV458 showed binding to all states of hMPV B2 F, while control mAbs 101F and MPE8 showed binding to only the nonreduced state. These data suggest the MPV458 epitope is at least partially linear. As the epitope for MPV458 lies within the trimer interface, the mechanism by which B cells recognize this epitope is unclear. To determine if the MPV458 epitope is exposed on the surface of virally infected cells, flow cytometry was performed using MPV458, MPE8, and a negative control pneumococcal-specific antibody (FIGS. 20A-20D). Both MPV458 and MPE8 induced a fluorescent shift in virally infected cells, while the negative control mAb did not. This indicates the MPV F protein is either in monomeric form on the surface of infected cells, or that hMPV F trimer exhibits breathing motion that allows for binding of MPV458. By comparing the binding sites with previously described hMPV F-specific mAbs that have been structurally characterized (MPE8, 101F, DS7), the MPV458 epitope is distant from all three known antigenic sites (IV, VI, and III), and lies on the opposite face of the monomeric hMPV F protein (FIGS. 9D, 9E). This unique epitope was unexpected on the hMPV F protein, although one intratrimeric epitope has recently been observed on the influenza hemagglutinin protein by mAb FluA-20 (Bangaru et al., *Cell* 177, 1136-1152.e18 (2019)). However, FluA-20 was non-neutralizing and functioned by disrupting the HA trimer and inhibiting cell-to-cell spread. Evidence for Pneumovirus F protein breathing was previously demonstrated on the RSV F protein, whereby the mAb CR9501 that binds at antigenic site V enhances opening of the pre-fusion RSV F protein (Gilman et al., *Nat. Commun.* 10, 2105 (2019)).

Abs MPV458 and MPV465 demonstrate a new class of neutralizing hMPV F-specific human antibodies. These mAbs bind at a newly defined epitope on the hMPV F protein defined by the alpha helix 66-87. This new epitope is the first defined on the head of the hMPV F protein. The RSV F protein has at least two antigenic sites that are surface exposed on the head of the trimeric surface (antigenic sites Ø and V), however, such antigenic sites have not yet been identified for hMPV F, likely due to glycan shielding (Biacchesi et al., *J. Virol.* 78, 12877-12887 (2004)). The results presented herein provide insights on the human antibody response to the hMPV F protein, and responses to viral glycoproteins. At least MPV458 can be potentially applied to the treatment and prevention of hMPV infection.

Example 9

Materials and Methods for Example 8

Blood draws and informed consent: Healthy human donors were recruited to the University of Georgia Clinical and Translational Research Unit. After obtaining informed consent, 90 mL of blood was drawn by venipuncture into 9 heparin-coated tubes, and 10 mL of blood was collected into a serum separator tube. Peripheral blood mononuclear cells (PBMCs) were isolated from human donor blood samples using Ficoll-Histopaque density gradient centrifugation, and PBMCs were frozen in the liquid nitrogen vapor phase until further use.

Production and purification of recombinant hMPV F proteins: Plasmids encoding cDNAs for hMPV A1 F, A2 F, B1 F, B2 F (Bar-Peled et al., *J. Virol. doi:*10.1128/JVI.00342-19 (2019) doi:10.1128/jvi.00342-19) and hMPVF 130-BV (Battles et al., *Nat. Commun.* 8, 1528 (2017)) proteins were synthesized (Genscript) and cloned into the pcDNA3.1+ vector. The plasmids were expanded by transformation in *Escherichia coli* DH5a cells with 100 µg/mL of ampicillin (Thermo Fisher Scientific) for selection. Plasmids were purified using the EZNA®. plasmid maxi kit (Omega BioTek), according to the manufacturer's protocol. To generate the stable cell lines that express hMPV B2 F, hMPV B2 F GCN4, and hMPV F 130-BV, HEK293F (Thermo Fisher Scientific) cells were plated into a 12 well plate ($4\times10^5$ per well) with 1 mL of growth medium (Dulbecco's Modified Eagle Medium (DMEM; CORNING®) 10% Fetal bovine serum (FBS; CORNING®) 1 day before transfection. For each milliliter of transfection, 1 µg of plasmid DNA was mixed with 4 µg of 25,000-molecular-weight polyethylenimine (PEI; PolySciences Inc.) in 66.67 µl OPTI-MEM® cell culture medium (Gibco). After 30 min, the DNA-PEI mixture was added to HEK293F cells in OPTI-MEM®. After 3 to 4 days, 20 µl supernatant of cell culture was used for Western blot to determine the expression of protein. Then the culture medium was replaced with 1 mL growth medium supplemented with G418 (Geneticin; VWR) antibiotic to a final concentration of 250 µg/mL. After 2-3 days, HEK293F cells were resuspended with the growth medium supplemented with G418, expanded to a 25-cm² cell culture flask. Cells were trypsinized once they reach 80-90% confluency and further expanded to a 75-cm² cell culture flask. Again, at 80-90% confluency, trypsinized the cells were transferred to 250 mL flask in 100 mL 293 FREESTYLE™ medium (Gibco) supplemented with G418 and cultured in shaking incubator at 37° C. with 5% CO₂.

For protein expression and purification, the stable cell lines were expanded in 500 mL of 293 FREESTYLE™ medium supplemented with G418 at 1×10⁶/mL. The rest of the constructs are expressed by transfection with HEK293F cells. After 5 to 7 days, the cultures were centrifuged to pellet the cells, and the supernatants were filtered through a 0.45-µm sterile filter. Recombinant proteins were purified directly from the filtered culture supernatants using HIS-TRAP™ Excel columns (GE Healthcare Life Sciences). Each column was stored in 20% ethanol and washed with column volumes (CV) of wash buffer (20 mM Tris pH 7.5, 500 mM NaCl, and 20 mM imidazole) before loading samples onto the column. After sample application, columns were washed with 10 CV of wash buffer. Proteins were eluted from the column with 6 CV of elution buffer (20 mM Tris pH 7.5, 500 mM NaCl, and 250 mM imidazole). Proteins were concentrated and buffer exchanged into phosphate buffered saline (PBS) using AMICON® Ultra-15 centrifugal filter units with a 30-kDa cutoff (Millipore Sigma).

Trypsinization of hMPVF: In order to generate homogeneous cleaved trimeric hMPV F, TPCK(L-1-tosylamido-2-phenylethyl chloromethyl ketone)-trypsin (Thermo Scientific) was dissolved in double-distilled water (ddH₂O) at 2 mg/mL. Purified hMPV B2 F was incubated with TAME (p-toluene-sulfonyl-L-arginine methyl ester) units/mg of TPCK-trypsin for 1 h at 37° C. Trimeric B2 F was purified from the digestion reaction mixture by size exclusion chromatography on a SUPERDEX® S200, 16/600 column (GE Healthcare Life Sciences) in column buffer (50 mM Tris pH 7.5, and 100 mM NaCl). The trimeric F was identified by a shift in the elution profile from monomeric hMPV B2 F proteins. The fractions containing the trimers and monomers were concentrated using 30-kDa SPIN-X® UF concentrators (CORN INGA) before subjecting them to following assays.

Generation of hMPV F-specific hybridomas: For hybridoma generation, 10 million peripheral blood mononuclear cells (PBMCs) purified from blood of healthy donors were mixed with 8 million previously frozen and irradiated NIH 3T3 cells modified to express human CD40L, human interleukin-21 (IL-21), and human BAFF (gift from Deepta Bhattacharya, Washington University) in 80 mL STEMCELL™ medium A (STEMCELL™ Technologies) containing 6.3 µg/mL of CpG (phosphorothioate-modified oligodeoxynucleotide (Invitrogen, see PCT Publication No. WO 2017/011394A1, and Bar-Peled et al., *J. Virol. doi:* 10.1128/JVI.00342-19 (2019) doi:10.1128/jvi.00342-19, both incorporated herein by reference) and 1 µg/mL of cyclosporine (Sigma). The mixture of cells was plated in four 96-well plates at 200 µl per well in STEMCELL™ medium A. After 6 days, culture supernatants were screened by an ELISA for binding to recombinant hMPV B2 F protein, and cells from positive wells were electrofused with a nonsecreting myeloma cell line as previously described (Bar-Peled et al., 2019, supra). Cells from each cuvette were resuspended in 20 mL STEMCELL™ medium A containing 1×HAT (hypoxanthineaminopterin-thymidine; Sigma-Aldrich), 0.2× HT (hypoxanthine-thymidine; CORNING®), and 0.3 µg/mL ouabain (Thermo Fisher Scientific) and plated at 50 µl per well in a 384-well plate. After 7 days, cells were fed with 25 µl of STEMCELL™ medium A. The supernatant of hybridomas were screened after 2 weeks for antibody production by ELISA, and cells from wells with reactive supernatants were expanded to 48-well plates for 1 week in 0.5 mL of STEMCELL™ medium E (STEMCELL™ Technologies), before being screened again by ELISA. Positive hybridomas were then subjected to single-cell fluorescence-activated sorting into 384-well plates containing 75% of STEMCELL™ medium A plus 25% of STEMCELL™ medium E. Two weeks after cell sorting, hybridomas were screened by ELISA before further expansion of wells containing hMPV F—specific hybridomas.

Human mAb and Fab production and purification: For recombinant mAbs, plasmids encoding cDNAs for the heavy and light chain sequences of 101F (McLellan et al., *J. Virol.* 84, 12236-12244 (2010), MPE8 (Corti et al., Nature 501, 439-43 (2013)), and DS7 (Williams et al., *J. Virol.* 81, 8315-8324 (2007) were synthesized (GenScript), and cloned into vectors encoding human IgG1 and lamda or kappa light chain constant regions, respectively. Plasmids were maxipreped, and mAbs were obtained by transfection of plasmids into FREESTYLE™ HEK293F cells as described above. For hybridoma-derived mAbs, hybridoma cell lines were expanded in STEMCELL™ medium A until 80% confluent in 75-cm² flasks. Cells from one 75-cm² cell culture flask were collected with a cell scraper and expanded to 225-cm² cell culture flasks in serum-free medium (Hybridoma-SFM; Thermo Fisher Scientific). Recombinant cultures from transfection were stopped after 5 to 7 days, hybridoma cultures were stopped after 30 days. Culture supernatants from both approaches were filtered using 0.45-µm filter to remove cell debris. mAbs were purified directly from culture supernatants using HITRAP™ protein G columns (GE Healthcare Life Sciences) according to the manufacturer's protocol. To obtain Fab fragments, papain digestion was performed using the Pierce Fab preparation kit (Thermo Fisher Scientific) according to the manufacturer's protocol. Fab fragments were purified by removing IgG and Fc contaminants using a HITRAP™ MABSELECT-SURE™ (GE Healthcare Life Sciences) column according to the manufacturer's protocol.

Isotype determination for human mAbs: For determination of mAb isotypes, 96-well Immulon HB 4×ELISA plates (Thermo Fisher Scientific) were coated with 2 µg/mL of each mAb in PBS (duplicate wells for each sample). The plates were incubated at 4° C. overnight and then washed once with water. Plates were blocked with blocking buffer (2% nonfat milk, 2% goat serum in PBS-T) and then left to incubate for 1 h at room temperature. After incubation, the plates were washed three times with water. Isotype-specific antibodies obtained from Southern Biotech (goat anti-human kappa-alkaline phosphatase [AP] [catalog number 100244-340], goat anti-human lamda-AP [catalog number 100244-376], mouse anti-human IgG1 [Fc]-AP [catalog number 100245714], mouse anti-human IgG2 [Fc]-AP [catalog number 100245-734], mouse anti-human IgG3 [hinge]-AP [catalog number 100245-824], and mouse anti-human IgG4 [Fc]-AP [catalog number 100245-812]) were diluted 1:1,000 in blocking buffer, and 50 µl of each solution was added to the respective wells. Plates were incubated for 1 h at room temperature and then washed five times with PBS-T. The PNPP substrate was prepared at 1 mg/mL in substrate buffer (1 M Tris base, 0.5 mM MgCl₂, pH 9.8), 100

µl of this solution was added to each well. Plates were incubated for 1 h at room temperature and read at 405 nm on a BioTek plate reader.

Western blot: Protein samples in reducing condition were mixed with loading buffer containing β-ME and heated at 96° C. for 10 minutes before loading on the 4-12% Bis-Tris Plus gels (Invitrogen). Same samples were mixed in non-reducing loading buffer without any other treatment. Then samples were transferred to PVDF membranes via iBlot system (Invitrogen) and blocked with 5% blocking buffer (5% blocker in PBST) at 4° C. overnight. Primary antibodies were diluted at 0.5 µg/mL in PBST and HRP-conjugated goat anti human secondary antibody was diluted at 1:10,000 in PBST. Both incubations were 1 hour at room temperature with 5×PBST wash in between. Substrate (Pierce ECL Western Blotting Substrate, Thermo Scientific) was added immediately before the image was taken with ChemiDoc Imaging System (BioRad).

Negative-stain electron microscopy analysis: All samples were purified by size exclusion chromatography on a Super-dex S200, 16/600 column (GE Healthcare Life Sciences) in column buffer before they were applied on grids. Carbon-coated copper grids (Electron Microscopy Sciences) were overlaid with 5 µl proteins (10 µg/mL) for 3 min. The grid was washed in water twice and then stained with 0.75% uranyl formate for 1 min. Negative-stain electron micrographs were acquired using a JEOL JEM1011 transmission electron microscope equipped with a high-contrast 2K-by-2K AMT midmount digital camera at a 40,000× magnification.

Crystallization and structure determination of the MPV458 Fab+B2 F complex: To make the complex of MPV458 Fab+B2 F, purified trypsinized B2 F trimer was added to MPV458 Fab at a 1:2 molar ratio and incubate at 4° C. overnight. To crystallize the complex, the sample was subjected to size exclusion chromatography (S200, 16/300, GE Healthcare Life Sciences) in 50 mM Tris pH 7.5, 100 mM NaCl. The fractions containing the complex was concentrated to 14.9 mg/mL and crystallization trials were prepared on a TTP LabTech Mosquito Robot in sitting-drop MRC-2 plates (Hampton Research) using several commercially available crystallization screens. Crystals were obtained in the Crystal Screen HT (Hampton research) in condition F3 (0.5 M Ammonium sulfate, 0.1 M Sodium citrate tribasic dihydrate pH 5.6, 1.0 M Lithium sulfate monohydrate). Crystals were harvested and cryo-protected with 30% glycerol in the mother liquor before being flash frozen in liquid nitrogen. X-ray diffraction data were collected at the Advanced Photon Source SER-CAT beamline 21-ID-D. Data were indexed and scaled using XDS.4 A molecular replacement solution was obtained in Phaser5 using the hMPV pre-fusion F structure (PDB 5WB0) and the Fab structure (PDB 4Q9Q). The structure of the complex was completed by manually building in COOT6 followed by subsequent rounds of manual rebuilding and refinement in Phenix5. The data collection and refinement statistics are shown in Table S2.

RT-PCR for hybridoma mAb variable gamma chain and variable light chain: RNA was isolated from expanded hybridoma cells using the ENZA® total RNA kit (Omega BioTek) according to the manufacturer's protocol. A Qiagen ONESTEP™ RT-PCR kit was used for cDNA synthesis and PCR amplification. For RT-PCRs, 50-µl reaction mixtures were designed with the following final concentrations: 1× Qiagen ONESTEP™ RT-PCR buffer, 400 µM deoxynucleoside triphosphate (dNTP) mix, 0.6 µM primer mix, 2 µl of Qiagen ONESTEP™ RT-PCR enzyme mix, 1 µg total of the template RNA, and RNase-free water. Three separate sets of primer mixes were used: gamma, kappa and lamda forward and reverse primers as previously described (Tiller et al., *J. Immunol. Methods* 329, 112-124 (2008)). The RT-PCR was performed in a thermocycler with the following program: 30 min at 50° C., 15 min at 95° C., and then a 3-step cycle with 30 repeats of denaturation for 30 s at 94° C., annealing for 30 s at 50° C., and extension for 1 min at 72° C., followed by 10 min of final extension at 72° C. Samples were analyzed by agarose gel electrophoresis and purified PCR products (ENZA® cycle pure kit; Omega) were cloned into the pCR2.1 vector using the Original TA cloning kit (Thermo Fisher Scientific) according to the manufacturer's protocol. Plasmids were purified from positive DH5a colonies with ENZA® plasmid DNA mini kit (Omega) and submitted to Genewiz for sequencing. Sequences were analyzed using IMGT/V-Quest (Tiller et al., *J. Immunol. Methods* 329, 112-124 (2008)). For MPV458, $2 \times 10^6$ of hybridoma cells were directly sent to GenScript for antibody variable domain sequencing.

Growth of hMPV: hMPV B2 strain TN/93-32 was obtained from BEI Resources (catalog number NR-22240), and hMPV A2 strain CAN/97-83 was a kind gift from Ralph Tripp. Viruses were grown in LLC-MK2 cells (ATCC). Cells were grown to 80% confluence in 225-cm² flasks in OPTI-MEM® supplemented with 2% FBS. For virus infection, cells were washed twice with Dulbecco's phosphate-buffered saline (DPBS; CORNING®) and then coated with 6 mL of diluted virus. The flasks were rocked for 1 h at room temperature to allow absorption of virus. Following this, 10 mL of OPTI-MEM® supplemented with 5 µg/mL trypsin-EDTA and 100 µg/mL $CaCl_2$) was added to the flask. Cells were incubated for 4 to 5 days before harvesting virus. For virus harvest, the medium was removed from the flask, and 5 mL of cold 25% (wt/vol) sterile-filtered sucrose was added to the flask. The flask was transferred to −80° C. until the solution was frozen. The flask was then moved to thaw at room temperature, followed by another freeze-thaw cycle. Cell lysates were scraped down, all cells and the sucrose solution were transferred to a sterile tube and centrifuged at 1,100 rpm for 5 min to remove cell debris. The clarified aliquoted of supernatant containing hMPV was flash frozen and tittered for later use.

hMPV plaque neutralization assay: LLC-MK2 cells were maintained in OPTI-MEM® (Thermo Fisher Scientific) supplemented with 2% fetal bovine serum and grown in 225-cm² flask at 37° C. in a $CO_2$ incubator. Two days prior to neutralization assays, cells were trypsinized and diluted in OPTI-MEM® at 80,000 cells/mL, 0.5 mL of cells were seeded into 24-well plates. On the day of the experiment, serially diluted mAbs isolated from hybridoma supernatants were incubated 1:1 with a suspension of infectious hMPV B2 strain TN/93-32 or hMPV A2 strain CAN/97-83 for 1 h. Following this, cells were inoculated with 50 µl of the antibody-virus mixture for 1 h with rocking at room temperature. Cells were then overlaid with 1 mL of 0.75% methylcellulose dissolved in OPTI-MEM® supplemented with 5 µg/mL trypsin-EDTA and 100 µg/mL $CaCl_2$). Cells were incubated for 4 days, after which the cells were fixed with 10% neutral buffered formalin. The cell monolayers were then blocked with blocking buffer (2% nonfat milk supplemented with 2% goat serum in PBS-T) for 1 h. The plates were washed with water, 200 µl of mouse anti-hMPV N primary antibody (catalog number C01851M; Meridian Biosciences) diluted 1:1,000 in blocking buffer was added to each well, and the plates were incubated for 1 h. The plates were then washed three times with water, after which 200 µl of goat anti-mouse IgG-horseradish peroxidase (HRP) secondary antibody (catalog number 5220-0286; SeraCare) diluted 1:1,000 in blocking solution was added to each well for 1 h. Plates were then washed five times with water, and 200 µl of TrueBlue peroxidase substrate (SeraCare) was added to each well. Plates were incubated until plaques were clearly visible. Plaques were counted by hand under a stereomicroscope and compared to a virus-only control, and the data were analyzed in GraphPad Prism using a nonlinear regression curve fit and the log(inhibitor)-versus-response function to calculate the $IC_{50}$ values.

Flow cytometry of hhMPV infected LLC-MK2 cells: LLC-MK2 cells were cultured in 75-cm² flask at 80-90% confluency, then infected with hMPV (CAN/97-83) at 0.1 MOI in OPTI-MEM® containing 100 ug/mL $CaCl_2$ and 5 ug/mL Trypsin-EDTA. 48 hours later, cells were washed twice with PBS and digested with Versene (Gibco) at 37° C. for 40-50 minutes. Cells were washed once with PBS then transferred to 1.5 mL tubes, pelleted and resuspended in 1 mL FACS buffer (PBS containing 5% FBS, inactivated 2% Human serum, inactivated 2% goat serum, 2 mM EDTA pH 8.0, 10% sodium azide) and incubate for 30 min to block Fc receptors. Cells were washed three times with PBS, then aliquoted in a 96 well U bottom plate for antibody staining. Mouse anti-human IgG Fc-APC (BioLegend) was used for secondary antibody. Stained cells were fixed in 4% paraformaldehyde and data was collected with Beckman Coulter CytoFLEX flow cytometer.

Experimental setup for biolayer interferometry: After obtaining an initial baseline in running buffer (PBS, 0.5% bovine serum albumin [BSA], 0.05% Tween 20, 0.04% thimerosal), 100 µg/mL of His-tagged hMPV F protein was immobilized on anti-penta-His biosensor tips (FortéBio) for 120 s. For binding competition, the baseline signal was measured again for 60 s before biosensor tips were immersed into wells containing 100 µg/mL of primary antibody for 300 s. Following this, biosensors were immersed into wells containing 100 µg/mL of a second mAb for 300 s. Percent binding of the second mAb in the presence of the first mAb was determined by comparing the maximal signal of the second mAb after the first mAb was added to the maximum signal of the second mAb alone. mAbs were considered noncompeting if maximum binding of the second mAb was ≥66% of its uncompeted binding. A level of between 33% and 66% of its uncompeted binding was considered intermediate competition, and ≤33% was considered competition. For affinity studies, hMPV B2F or hMPV F BV130 proteins were loaded as described above, and decreasing concentrations (100/75/50/12.5/0 µg/mL) of Fabs or IgGs were analyzed for binding by association for 120 s and dissociation for 600 s. OCTET® data analysis software was used to analyze the data. Values for reference wells containing no antibody were subtracted from the data, and affinity values were calculating using the local and partial fit curves function. Binding curves were independently graphed in GraphPad Prism for data visualization.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated monoclonal antibody or antigen binding fragment thereof, comprising:

a) a heavy chain variable region ($V_H$) and a light chain variable region ($V_L$) comprising a heavy chain complementarity determining region (HCDR) 1, a HCDR2, and a HCDR3, and a light chain complementarity determining region (LCDR) 1, a LCDR2, and a LCDR3 of the $V_H$ and $V_L$ set forth as SEQ ID NOs: 1 and 2, respectively;

b) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 11 and 12, respectively;

c) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 21 and 22, respectively;

d) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 31 and 32, respectively;

e) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 49 and 50, respectively; or f) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 59 and 60, respectively, wherein the monoclonal antibody specifically binds to human metapneumovirus (hMPV) F protein and neutralizes hMPV, and wherein the HCDR1, HCDR2, HCDR3, LCDR1, LCDR2 and LCDR3 are identified using Kabat, Chothia or IMGT numbering.

2. The isolated monoclonal antibody or antigen binding fragment of claim 1, wherein a) the HCDR1, the HCDR2, the HCDR3, the LCDR1, the LCDR2, and the LCDR3 comprise the amino acids sequences set forth as SEQ ID NOs: 5, 6, 7, 8, 9 and 10, respectively;

b) the HCDR1, the HCDR2, the HCDR3, the LCDR1, the LCDR2, and the LCDR3 comprise the amino acids sequences set forth as SEQ ID NOs: 15, 16, 17, 18, 19 and 20, respectively;

c) the HCDR1, the HCDR2, the HCDR3, the LCDR1, the LCDR2, and the LCDR3 comprise the amino acids sequences set forth as SEQ ID NOs: 25, 26, 27, 28, 29 and 30, respectively;

d) the HCDR1, the HCDR2, the HCDR3, the LCDR1, the LCDR2, and the LCDR3 comprise the amino acids sequences set forth as SEQ ID NOs: 35, 36, 37, 38, 39 and 40, respectively;

e) the HCDR1, the HCDR2, the HCDR3, the LCDR1, the LCDR2, and the LCDR3 comprise the amino acids sequences set forth as SEQ ID NOs: 53, 54, 55, 56, 57, and 58, respectively; or f) the HCDR1, the HCDR2, the HCDR3, the LCDR1, the LCDR2, and the LCDR3 comprise the amino acids sequences set forth as SEQ ID NOs: 63, 64, 65, 66, 67, and 68, respectively.

3. The isolated monoclonal antibody or antigen binding fragment of claim 2, wherein a) the $V_H$ and the $V_L$ comprise the amino acid sequences at least 90% identical to the amino acid sequences set forth as SEQ ID NOs: 1 and 2, respectively;

b) the $V_H$ and the $V_L$ comprise the amino acid sequences at least 90% identical to the amino acid sequences set forth as SEQ ID NOs: 11 and 12, respectively;

c) the $V_H$ and the $V_L$ comprise the amino acid sequences at least 90% identical to the amino acid sequences set forth as SEQ ID NOs: 21 and 22, respectively;

d) the $V_H$ and the $V_L$ comprise the amino acid sequences at least 90% identical to the amino acid sequences set forth as SEQ ID NOs: 31 and 32, respectively;

e) the $V_H$ and the $V_L$ comprise the amino acid sequences at least 90% identical to the amino acid sequences set forth as SEQ ID NOs: 49 and 50, respectively; or f) the $V_H$ and the $V_L$ comprise the amino acid sequences at least 90% identical to the amino acid sequences set forth as SEQ ID NOs: 59 and 60, respectively.

4. The isolated monoclonal antibody or antigen binding fragment of claim 1, comprising a human framework region.

5. The isolated monoclonal antibody or antigen binding fragment of claim 1, wherein:

a) the $V_H$ and the $V_L$ comprise the amino acid sequences set forth as SEQ ID NOs: 1 and 2, respectively;

b) the $V_H$ and the $V_L$ comprise the amino acid sequences set forth as SEQ ID NOs: 11 and 12, respectively;

c) the $V_H$ and the $V_L$ comprise the amino acid sequences set forth as SEQ ID NOs: 21 and 22, respectively;

d) the $V_H$ and the $V_L$ comprise the amino acid sequences set forth as SEQ ID NOs: 31 and 32, respectively;

e) the $V_H$ and the $V_L$ comprise the amino acid sequences set forth as SEQ ID NOs: 49 and 50, respectively; or f) the $V_H$ and the $V_L$ comprise the amino acid sequences set forth as SEQ ID NOs: 59 and 60, respectively.

6. The isolated monoclonal antibody of claim 1, wherein the antibody comprises a human constant domain.

7. The isolated monoclonal antibody of claim 1, wherein the antibody is a human antibody.

8. The isolated monoclonal antibody of claim 1, wherein the antibody is an IgG.

9. The isolated monoclonal antibody of claim 1, comprising a recombinant constant domain comprising a modification that increases the half-life of the antibody.

10. The isolated monoclonal antibody of claim 9, wherein the modification increases binding to the neonatal Fc receptor.

11. The isolated monoclonal antibody or antigen binding fragment of claim 1, wherein the antibody neutralizes group A and group B hMPV.

12. The isolated monoclonal antibody or antigen binding fragment of claim 1, wherein the antibody neutralizes group B2 hMPV.

13. The isolated monoclonal antigen binding fragment of claim 1.

14. The isolated monoclonal antigen binding fragment of claim 13, wherein the antigen binding fragment is a Fv, Fab, F(ab')$_2$, scFV or a scFV$_2$ fragment.

15. The isolated monoclonal antibody or antigen binding fragment of claim 1, conjugated to an effector molecule or a detectable marker.

16. A bispecific antibody comprising the monoclonal antibody or antigen binding fragment of claim 1.

17. An isolated nucleic acid molecule encoding the monoclonal antibody or antigen binding fragment of claim 1, or a $V_H$ or $V_L$ of the antibody or antigen binding fragment.

18. The isolated nucleic acid molecule of claim 17, comprising a) the $V_H$ and the $V_L$ nucleotide sequences set forth as one of SEQ ID NOs: 3 and 4, respectively;

b) the $V_H$ and the $V_L$ nucleotide sequences set forth as one of SEQ ID NOs: 13 and 14, respectively;

c) the $V_H$ and the $V_L$ nucleotide sequences set forth as one of SEQ ID NOs: 23 and 24, respectively;

d) the $V_H$ and the $V_L$ nucleotide sequences set forth as one of SEQ ID NOs: 33 and 34, respectively;

e) the $V_H$ and the $V_L$ nucleotide sequences set forth as one of SEQ ID NOs: 51 and 52, respectively; or f) the $V_H$ and the $V_L$ nucleotide sequences set forth as one of SEQ ID NOs: 61 and 62, respectively.

19. The isolated nucleic acid molecule of claim 17, wherein the nucleic acid molecule is a cDNA sequence.

20. The isolated nucleic acid molecule of claim 17, operably linked to a promoter.

21. A vector comprising-a nucleic acid molecule encoding the isolated monoclonal antibody or antigen binding fragment of claim 1, or a $V_H$ or $V_L$ of the antibody or antigen binding fragment.

22. A host cell comprising a nucleic acid molecule encoding the isolated monoclonal antibody or antigen binding fragment of claim 1, or a $V_H$ or $V_L$ of the antibody or antigen binding fragment, or a vector comprising the nucleic acid molecule.

23. A pharmaceutical composition, comprising an effective amount of a monoclonal antibody, an antigen binding fragment thereof, a nucleic acid molecule encoding the monoclonal antibody or antigen binding fragment, or a vector comprising the nucleic acid molecule; and a pharmaceutically acceptable carrier, wherein the monoclonal antibody, or antigen binding fragment thereof, comprise:

a) a heavy chain variable region ($V_H$) and a light chain variable region ($V_L$) comprising a heavy chain complementarity determining region (HCDR) 1, a HCDR2, and a HCDR3, and a light chain complementarity determining region (LCDR) 1, a LCDR2, and a LCDR3 of the $V_H$ and $V_L$ set forth as SEQ ID NOs: 1 and 2, respectively;

b) a heavy chain variable region and a light chain variable region comprising aHCDR1, a HCDR2, and a HCDR3, and a LCDR1, a LCDR2, and a LCDR3 of the $V_H$ and $V_L$ set forth as SEQ ID NOs: 11 and 12, respectively;

c) a heavy chain variable region and a light chain variable region comprising HCDR1, a HCDR2, and a HCDR3, and a LCDR1, a LCDR2, and a LCDR3 of the $V_H$ and $V_L$ set forth as SEQ ID NOs: 21 and 22, respectively;

d) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 31 and 32, respectively;

e) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 49 and 50, respectively; or f) a heavy chain variable region and a light chain variable region comprising a HCDR1, a HCDR2, and a HCDR3, and a LCDR1, a LCDR2, and a LCDR3 of the $V_H$ and $V_L$ set forth as SEQ ID NOs: 59 and 60, respectively, wherein the monoclonal antibody specifically binds to human metapneumovirus (hMPV) F protein and neutralizes hMPV, and wherein the HCDR1, HCDR2, HCDR3, LCDR1, LCDR2 and LCDR3 are identified using Kabat, Chothia or IMGT numbering.

24. A method of producing an isolated monoclonal antibody, or antigen binding fragment that specifically binds to hMPV F protein, comprising:

expressing one or more nucleic acid molecules encoding the isolated monoclonal antibody, antigen binding fragment of claim 1 in a host cell; and purifying the monoclonal antibody or antigen binding fragment, thereby producing the isolated monoclonal antibody or antigen binding fragment.

25. A method of detecting the presence of hMPV in a biological sample from a human subject, comprising:

contacting the biological sample with an effective amount of the isolated monoclonal antibody or antigen binding fragment of claim 1 under conditions sufficient to form an immune complex; and detecting the presence of the immune complex in the biological sample, wherein the presence of the immune complex in the biological sample indicates the presence of the hMPV in the sample.

26. The method of claim 25, wherein detecting the detecting the presence of the immune complex in the biological sample indicates that the subject has an hMVP infection.

27. A method of inhibiting an hMPV infection in a subject, comprising administering an effective amount of pharmaceutical composition of claim 23 to the subject, wherein the subject has or is at risk of an hMPV infection.

\* \* \* \* \*

SEQUENCE LISTING

```
<160> NUMBER OF SEQ ID NOS: 72

<210> SEQ ID NO 1
<211> LENGTH: 121
<212> TYPE: PRT
<213> ORGANISM: Homo sapiens

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Ser Trp Thr Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Ile Asp Thr Ser Arg Asn Gln Phe Ser Leu
65                  70                  75                  80

Lys Leu Ile Ser Val Thr Ala Ala Asp Thr Ala Val Tyr Tyr Cys Ala
            85                  90                  95

Arg Gly Val Arg Gly Gly Tyr Asn Leu Trp His Phe Asp Val Trp Gly
            100                 105                 110

Gln Gly Thr Leu Val Thr Val Ser Ser
        115                 120

<210> SEQ ID NO 2
<211> LENGTH: 107
<212> TYPE: PRT
```

```
<213> ORGANISM: Homo sapiens

<400> SEQUENCE: 2

Ser Tyr Glu Leu Ser Gln Ser Pro Ser Val Ser Val Ser Pro Gly Gln
1               5                   10                  15

Thr Ala Arg Ile Thr Cys Ser Gly Asp Lys Leu Gly Asn Lys Tyr Ala
            20                  25                  30

Ser Trp Tyr Gln Gln Lys Pro Gly Gln Ser Pro Val Leu Val Ile Tyr
        35                  40                  45

Gln Asp Asp Lys Arg Pro Ser Gly Ile Pro Glu Arg Phe Ser Gly Ser
    50                  55                  60

Asn Ser Gly Asn Thr Ala Thr Leu Thr Ile Gly Gly Thr Gln Ala Met
65                  70                  75                  80

Asp Glu Ala Asp Tyr Ser Cys Gln Ala Trp Asp Gly Arg Thr Ala Val
                85                  90                  95

Val Phe Gly Gly Gly Thr Lys Leu Thr Val Leu
            100                 105

<210> SEQ ID NO 3
<211> LENGTH: 364
<212> TYPE: DNA
<213> ORGANISM: Homo sapiens

<400> SEQUENCE: 3
caggtgcagc tacagcagtg gggcgcagga ctcttgaagc cttcggagac cctgtccctc      60
acctgcgctg tctatggtgg gtccttcagt ggttactctt ggacctggat tcgccagccc     120
ccagggaagg ggctggagtg gattggggaa atcaatcata gtggaagcac caactacaac     180
ccgtccctca gagtcgagt caccatatca atagacacgt ccaggaacca gttctccctg      240
aagctgatct ctgtgaccgc cgcggacacg gctgtatatt attgtgcgag aggcgtgcgt     300
ggtggctaca atttgtggca ctttgacgtc tggggccagg gaaccctggt caccgtctcc     360
tcag                                                                  364

<210> SEQ ID NO 4
<211> LENGTH: 322
<212> TYPE: DNA
<213> ORGANISM: Homo sapiens

<400> SEQUENCE: 4
tcctatgagc tgagtcagtc accctcagtg tccgtgtctc caggacagac agccagaatc      60
acctgctctg gagataaatt gggaataaa tatgcttcct ggtatcagca gaaaccaggc      120
cagtcccctg tgctggtcat ctatcaggat gacaagcggc cctcagggat ccctgagcga     180
ttctctggct ccaactctgg gaacacagcc actctgacca tcggcgggac ccaggctatg     240
gatgaggctg actattcctg tcaggcgtgg gacggcagaa ctgctgtggt tttcggcgga     300
gggaccaagc tgaccgtcct ag                                              322

<210> SEQ ID NO 5
<211> LENGTH: 8
<212> TYPE: PRT
<213> ORGANISM: Homo sapiens

<400> SEQUENCE: 5

Gly Gly Ser Phe Ser Gly Tyr Ser
1               5
```

<210> SEQ ID NO 6
<211> LENGTH: 7
<212> TYPE: PRT
<213> ORGANISM: Homo sapiens

<400> SEQUENCE: 6

Ile Asn His Ser Gly Ser Thr
1               5

<210> SEQ ID NO 7
<211> LENGTH: 15
<212> TYPE: PRT
<213> ORGANISM: Homo sapiens

<400> SEQUENCE: 7

Ala Arg Gly Val Arg Gly Gly Tyr Asn Leu Trp His Phe Asp Val
1               5                   10                  15

<210> SEQ ID NO 8
<211> LENGTH: 6
<212> TYPE: PRT
<213> ORGANISM: Homo sapiens

<400> SEQUENCE: 8

Lys Leu Gly Asn Lys Tyr
1               5

<210> SEQ ID NO 9
<211> LENGTH: 3
<212> TYPE: PRT
<213> ORGANISM: Homo sapiens

<400> SEQUENCE: 9

Gln Asp Asp
1

<210> SEQ ID NO 10
<211> LENGTH: 10
<212> TYPE: PRT
<213> ORGANISM: Homo sapiens

<400> SEQUENCE: 10

Gln Ala Trp Asp Gly Arg Thr Ala Val Val
1               5                   10

<210> SEQ ID NO 11
<211> LENGTH: 124
<212> TYPE: PRT
<213> ORGANISM: Homo sapiens

<400> SEQUENCE: 11

Gln Val Gln Leu Val Gln Ser Gly Gly Gly Gly Val Gln Pro Gly Arg
1               5                   10                  15

Ser Leu Arg Leu Ser Cys Ala Ala Ser Gly Phe Ile Phe Ser Asp Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Gln Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Val Glu Asp Thr Ala Val Tyr Tyr Cys
                85                  90                  95

-continued

```
Ala Lys Asp Gln Gly Arg Arg Tyr Tyr Tyr Ser Ser Gly Tyr Leu Asp
            100                 105                 110

Tyr Trp Gly Gln Gly Thr Leu Val Thr Val Ser Ser
        115                 120

<210> SEQ ID NO 12
<211> LENGTH: 108
<212> TYPE: PRT
<213> ORGANISM: Homo sapiens

<400> SEQUENCE: 12

Asp Ile Val Met Thr Gln Ser Pro Ala Ala Leu Ser Val Ser Pro Gly
1               5                   10                  15

Glu Arg Ala Thr Leu Ser Cys Arg Ala Ser His Ser Val Ala Ser Asn
            20                  25                  30

Leu Ala Trp Tyr Gln Gln Lys Pro Gly Gln Ala Pro Arg Leu Leu Ile
        35                  40                  45

Ser Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Arg Trp Pro Pro
                85                  90                  95

Trp Thr Phe Gly Gln Gly Thr Lys Val Glu Ile Lys
            100                 105

<210> SEQ ID NO 13
<211> LENGTH: 372
<212> TYPE: DNA
<213> ORGANISM: Homo sapiens

<400> SEQUENCE: 13
caggtgcagc tggtgcagtc tgggggaggc ggggtccagc ctgggaggtc cctgagactc      60
tcctgtgcag cctctggatt catcttcagt gactatggca tgcactgggt ccgccaggct     120
ccaggcaagg ggctggagtg ggtggcagtt atatcatatg atggaagtaa tcaatactat     180
gcagactccg tgaagggccg attcaccatc tccagagaca attccaggaa cacgctgtat     240
ctgcaaatga acagtctgag agttgaggac acggctgtat attactgtgc gaaagatcaa     300
gggaggaggt actattatag tagtggttat ctagactact ggggccaggg aaccctggtc     360
accgtctcct ca                                                         372

<210> SEQ ID NO 14
<211> LENGTH: 325
<212> TYPE: DNA
<213> ORGANISM: Homo sapiens

<400> SEQUENCE: 14
gacattgtga tgacccagtc tccagccgcc ctgtctgtgt ctccagggga acgagccacc      60
ctctcctgca gggccagtca cagtgttgcc agcaacctgg cctggtacca gcagaaacct     120
ggccaggctc ccaggctcct catctctggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataggt ggcctccgtg gacgttcggc     300
caagggacca agtggaaat caaac                                            325
```

```
<210> SEQ ID NO 15
<211> LENGTH: 8
<212> TYPE: PRT
<213> ORGANISM: Homo sapiens

<400> SEQUENCE: 15

Gly Phe Ile Phe Ser Asp Tyr Gly
1               5

<210> SEQ ID NO 16
<211> LENGTH: 8
<212> TYPE: PRT
<213> ORGANISM: Homo sapiens

<400> SEQUENCE: 16

Ile Ser Tyr Asp Gly Ser Asn Gln
1               5

<210> SEQ ID NO 17
<211> LENGTH: 17
<212> TYPE: PRT
<213> ORGANISM: Homo sapiens

<400> SEQUENCE: 17

Ala Lys Asp Gln Gly Arg Arg Tyr Tyr Tyr Ser Ser Gly Tyr Leu Asp
1               5                   10                  15

Tyr

<210> SEQ ID NO 18
<211> LENGTH: 6
<212> TYPE: PRT
<213> ORGANISM: Homo sapiens

<400> SEQUENCE: 18

His Ser Val Ala Ser Asn
1               5

<210> SEQ ID NO 19
<211> LENGTH: 3
<212> TYPE: PRT
<213> ORGANISM: Homo sapiens

<400> SEQUENCE: 19

Gly Ala Ser
1

<210> SEQ ID NO 20
<211> LENGTH: 10
<212> TYPE: PRT
<213> ORGANISM: Homo sapiens

<400> SEQUENCE: 20

Gln Gln Tyr Asn Arg Trp Pro Pro Trp Thr
1               5                   10

<210> SEQ ID NO 21
<211> LENGTH: 124
<212> TYPE: PRT
<213> ORGANISM: Homo sapiens

<400> SEQUENCE: 21

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ser Phe Ser Asp Tyr
```

-continued

```
                20              25              30
Gly Met Asp Trp Val Arg Gln Ala Pro Gly Lys Gly Leu Glu Trp Val
            35              40              45
Ala Val Ile Ser Tyr Asp Gly Ser Asn Gln Tyr Tyr Ala Asp Ser Val
        50              55              60
Lys Gly Arg Phe Thr Val Ser Arg Asp Asn Ser Lys Asn Thr Val Tyr
65              70              75              80
Leu Gln Met Asn Ser Leu Arg Ala Glu Asp Thr Ala Val Tyr Phe Cys
                85              90              95
Ala Lys Asp Glu Ser Arg Arg Tyr Tyr Tyr Ser Ser Gly Ile His Ser
            100             105             110
His Trp Gly Gln Gly Thr Leu Val Thr Val Ser Ser
            115             120
```

```
<210> SEQ ID NO 22
<211> LENGTH: 108
<212> TYPE: PRT
<213> ORGANISM: Homo sapiens

<400> SEQUENCE: 22
```

```
Asp Ile Val Met Thr Gln Ser Pro Ala Thr Leu Ser Val Ser Pro Gly
1               5               10              15
Glu Arg Ala Thr Leu Ser Cys Arg Ala Ser Gln Ser Val Ser Arg Asn
            20              25              30
Leu Ala Trp Tyr Gln Gln Lys Pro Gly Gln Ala Pro Arg Leu Leu Ile
        35              40              45
Phe Gly Ala Ser Thr Arg Ala Thr Gly Ile Pro Ala Arg Phe Ser Gly
        50              55              60
Ser Ala Ser Gly Thr Glu Phe Thr Leu Thr Ile Ser Ser Leu Gln Ser
65              70              75              80
Glu Asp Phe Ala Val Tyr Tyr Cys His Gln Tyr Asn Tyr Trp Pro Pro
                85              90              95
Gly Thr Phe Gly Gln Gly Thr Arg Leu Glu Ile Lys
            100             105
```

```
<210> SEQ ID NO 23
<211> LENGTH: 372
<212> TYPE: DNA
<213> ORGANISM: Homo sapiens

<400> SEQUENCE: 23
```

```
caggtgcagc tggtgcagtc tggggggaggc gtggtccagc ctgggaggtc cctgagactc      60
tcctgtgcag cctctggatt cagcttcagt gactatggca tggactgggt ccgccaggct     120
ccaggcaagg gactggagtg ggtggcagtt atatcatatg atggaagtaa tcaatactat     180
gcagactccg tgaagggccg attcaccgtc tccagagaca attccaagaa cacggtatat     240
ctgcaaatga acagcctgag agctgaggac acggctgtgt atttctgtgc aaaagatgaa     300
agtcgtaggt attattatag ttcagggatc catagccact ggggccaggg caccctggtc     360
accgtctcct ca                                                         372
```

```
<210> SEQ ID NO 24
<211> LENGTH: 324
<212> TYPE: DNA
<213> ORGANISM: Homo sapiens

<400> SEQUENCE: 24
```

```
gacattgtga tgacccagtc tccagccacc ctctctgtgt ctccagggga aagagccacc       60
ctctcctgca gggccagtca gagtgttagc cgcaacttag cctggtacca gcagaaacct      120
ggccaggctc ccaggctcct catctttggt gcgtccacca gggccactgg tatcccagcc      180
aggttcagtg gcagtgcgtc tgggacagag ttcactctca ccatcagcag cctgcagtct      240
gaagattttg cagtttatta ctgtcaccag tataattact ggcctccggg gactttttggc      300 caggggacca ggctggagat caaa                                              324
```

```
<210> SEQ ID NO 25
<211> LENGTH: 8
<212> TYPE: PRT
<213> ORGANISM: Homo sapiens

<400> SEQUENCE: 25

Gly Phe Ser Phe Ser Asp Tyr Gly
1               5

<210> SEQ ID NO 26
<211> LENGTH: 8
<212> TYPE: PRT
<213> ORGANISM: Homo sapiens

<400> SEQUENCE: 26

Ile Ser Tyr Asp Gly Ser Asn Gln
1               5

<210> SEQ ID NO 27
<211> LENGTH: 17
<212> TYPE: PRT
<213> ORGANISM: Homo sapiens

<400> SEQUENCE: 27

Ala Lys Asp Glu Ser Arg Arg Tyr Tyr Tyr Ser Ser Gly Ile His Ser
1               5                   10                  15

His

<210> SEQ ID NO 28
<211> LENGTH: 6
<212> TYPE: PRT
<213> ORGANISM: Homo sapiens

<400> SEQUENCE: 28

Gln Ser Val Ser Arg Asn
1               5

<210> SEQ ID NO 29
<211> LENGTH: 3
<212> TYPE: PRT
<213> ORGANISM: Homo sapiens

<400> SEQUENCE: 29

Gly Ala Ser
1

<210> SEQ ID NO 30
<211> LENGTH: 10
<212> TYPE: PRT
<213> ORGANISM: Homo sapiens

<400> SEQUENCE: 30

His Gln Tyr Asn Tyr Trp Pro Pro Gly Thr
1               5                   10
```

<210> SEQ ID NO 31
<211> LENGTH: 128
<212> TYPE: PRT
<213> ORGANISM: Homo sapiens

<400> SEQUENCE: 31

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr His Asp
                20                  25                  30

Ser Ile His Trp Val Arg Gln Ala Pro Gly Gln Arg Leu Glu Trp Met
            35                  40                  45

Gly Trp Ile Asn Val Gly Asn Gly Asp Thr Lys Ser Ser Gln Lys Phe
        50                  55                  60

Gln Asp Arg Leu Thr Ile Thr Arg Asp Thr Ser Ala Asn Thr Ala Tyr
65                  70                  75                  80

Met Glu Val Arg Ser Leu Lys Tyr Glu Asp Thr Ala Met Tyr Phe Cys
                85                  90                  95

Ala Arg Val Asp Gln Tyr Cys Ile Gly Gly Val Cys Tyr Gly Gly Lys
                100                 105                 110

Asn Trp Phe Asp Pro Trp Gly Gln Gly Thr Leu Val Thr Val Ser Ser
            115                 120                 125

<210> SEQ ID NO 32
<211> LENGTH: 109
<212> TYPE: PRT
<213> ORGANISM: Homo sapiens

<400> SEQUENCE: 32

Ser Tyr Glu Leu Asn Gln Pro Pro Ser Val Ser Val Ala Pro Gly Gln
1                   5                   10                  15

Thr Ala Met Ile Thr Cys Gly Gly Tyr Tyr Val Gly Val Lys Ser Leu
                20                  25                  30

His Trp Tyr Gln Gln Lys Ala Gly Gln Ala Pro Val Leu Val Val His
            35                  40                  45

Asp Asp Ser Asp Arg Pro Ser Gly Ile Pro Glu Arg Phe Ser Gly Ser
        50                  55                  60

Lys Ser Gly Asp Thr Ala Thr Leu Ile Ile Ser Arg Val Glu Ala Gly
65                  70                  75                  80

Asp Glu Ala Asp Tyr Tyr Cys Gln Val Trp Asp Arg Asp Ser Asp His
                85                  90                  95

Pro Tyr Val Phe Gly Thr Gly Thr Thr Val Thr Val Leu
                100                 105

<210> SEQ ID NO 33
<211> LENGTH: 384
<212> TYPE: DNA
<213> ORGANISM: Homo sapiens

<400> SEQUENCE: 33
caggtgcagc tggtgcagtc tgggggctgag gtgaagaagc ctgggggcctc agtgaaggtt        60 tcctgcaagg cttctggata caccttcact catgattcta tccattgggt gcgccaggcc       120
cccggacaaa ggcttgagtg gatgggatgg atcaacgttg gcaatggtga cacaaaatct       180
tcacagaagt ttcaggacag actcaccatt accagggaca catctgcgaa cacagcctac       240
atggaggtca gaagcctgaa atatgaagat acggctatgt atttctgtgc gagagtggac       300

-continued

```
caatattgta ttggtggtgt ctgctatggg ggaaagaatt ggttcgaccc ctggggccag      360
ggaaccctgg tcaccgtctc ctca                                             384

<210> SEQ ID NO 34
<211> LENGTH: 327
<212> TYPE: DNA
<213> ORGANISM: Homo sapiens

<400> SEQUENCE: 34
tcctatgagc tgaatcagcc accctcggtg tcggtggccc cagggcagac ggccatgatt       60
acctgtgggg gatattatgt cggagttaaa agtttgcact ggtaccaaca gaaggcaggc      120
caggcccctg tgctggtcgt ccatgatgat agcgaccggc cctctgggat ccctgagcga      180
ttctctggct ccaaatctgg cgacacggcc acactgatca tcagtagggt cgaagccggg      240
gatgaggccg actattactg tcaggtgtgg gataggggata gtgatcatcc ttatgtcttc      300
ggaactggga ccacggtcac cgtcctg                                         327

<210> SEQ ID NO 35
<211> LENGTH: 8
<212> TYPE: PRT
<213> ORGANISM: Homo sapiens

<400> SEQUENCE: 35

Gly Tyr Thr Phe Thr His Asp Ser
1               5

<210> SEQ ID NO 36
<211> LENGTH: 8
<212> TYPE: PRT
<213> ORGANISM: Homo sapiens

<400> SEQUENCE: 36

Ile Asn Val Gly Asn Gly Asp Thr
1               5

<210> SEQ ID NO 37
<211> LENGTH: 21
<212> TYPE: PRT
<213> ORGANISM: Homo sapiens

<400> SEQUENCE: 37

Ala Arg Val Asp Gln Tyr Cys Ile Gly Gly Val Cys Tyr Gly Gly Lys
1               5                   10                  15

Asn Trp Phe Asp Pro
            20

<210> SEQ ID NO 38
<211> LENGTH: 6
<212> TYPE: PRT
<213> ORGANISM: Homo sapiens

<400> SEQUENCE: 38

Tyr Val Gly Val Lys Ser
1               5

<210> SEQ ID NO 39
<211> LENGTH: 3
<212> TYPE: PRT
<213> ORGANISM: Homo sapiens

<400> SEQUENCE: 39
```

-continued

```
Asp Asp Ser
1

<210> SEQ ID NO 40
<211> LENGTH: 12
<212> TYPE: PRT
<213> ORGANISM: Homo sapiens

<400> SEQUENCE: 40

Gln Val Trp Asp Arg Asp Ser Asp His Pro Tyr Val
1               5                   10

<210> SEQ ID NO 41
<211> LENGTH: 122
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Val Ser Ser Ser
            20                  25                  30

Tyr Met Ser Trp Val Arg Gln Thr Pro Gly Lys Gly Leu Glu Trp Ile
        35                  40                  45

Ser Val Phe Tyr Ser Gly Gly Thr Thr Tyr Tyr Ala Asp Ala Val Lys
    50                  55                  60

Gly Arg Phe Ser Ile Ser Met Asp Thr Ser Lys Asn Thr Leu His Leu
65                  70                  75                  80

Gln Met Asn Ser Leu Arg Val Glu Asp Thr Ala Ile Tyr Tyr Cys Ala
                85                  90                  95

Arg Val Leu Ser Arg Ala Ser Gly Met Pro Asp Ala Phe Asp Ile Trp
            100                 105                 110

Gly Pro Gly Thr Met Val Thr Val Ser Ser
            115                 120

<210> SEQ ID NO 42
<211> LENGTH: 108
<212> TYPE: PRT
<213> ORGANISM: Homo sapiens

<400> SEQUENCE: 42

Glu Leu Ala Leu Ile Gln Pro Ala Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Thr Leu Thr Val Leu Gly Gln
            100                 105

<210> SEQ ID NO 43
<211> LENGTH: 124
```

```
<212> TYPE: PRT
<213> ORGANISM: Homo sapiens

<400> SEQUENCE: 43

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ala Ser Ser Ser Tyr Ser Asp Tyr Ala Asp Ser Ala
    50                  55                  60

Lys Gly Arg Phe Thr Ile Ser Arg Asp Asn Ala Lys Thr Ser Leu Phe
65                  70                  75                  80

Leu Gln Met Asn Ser Leu Arg Ala Glu Asp Thr Ala Ile Tyr Phe Cys
                85                  90                  95

Ala Arg Ala Arg Ala Thr Gly Tyr Ser Ser Ile Thr Pro Tyr Phe Asp
            100                 105                 110

Ile Trp Gly Gln Gly Thr Leu Val Thr Val Ser Ser
        115                 120

<210> SEQ ID NO 44
<211> LENGTH: 110
<212> TYPE: PRT
<213> ORGANISM: Homo sapiens

<400> SEQUENCE: 44

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Arg Ser
                85                  90                  95

Leu Ser Gly Val Phe Gly Thr Gly Thr Lys Val Thr Val Leu
            100                 105                 110

<210> SEQ ID NO 45
<211> LENGTH: 19
<212> TYPE: PRT
<213> ORGANISM: Homo sapiens

<400> SEQUENCE: 45

Ser Ile Gly Ser Asn Arg Val Gly Ile Ile Lys Gln Leu Asn Lys Gly
1               5                   10                  15

Cys Ser Tyr

<210> SEQ ID NO 46
<211> LENGTH: 19
<212> TYPE: PRT
<213> ORGANISM: Homo sapiens

<400> SEQUENCE: 46
```

```
Thr Ala Ser Asn Lys Asn Arg Gly Ile Ile Lys Thr Phe Ser Asn Gly
1               5                   10                  15

Cys Asp Tyr

<210> SEQ ID NO 47
<211> LENGTH: 21
<212> TYPE: PRT
<213> ORGANISM: Homo sapiens

<400> SEQUENCE: 47

Ala Arg Val Asp Gln Tyr Cys Ile Gly Gly Val Cys Tyr Gly Gly Lys
1               5                   10                  15

Asn Trp Phe Asp Pro
            20

<210> SEQ ID NO 48
<211> LENGTH: 12
<212> TYPE: PRT
<213> ORGANISM: Homo sapiens

<400> SEQUENCE: 48

Gln Val Trp Asp Arg Asp Ser Asp His Pro Tyr Val
1               5                   10

<210> SEQ ID NO 49
<211> LENGTH: 115
<212> TYPE: PRT
<213> ORGANISM: Homo sapiens

<400> SEQUENCE: 49

Gln Gly Lys Leu Val Glu Ser Gly Gly Gly Val Ile Gln Pro Gly Arg
1               5                   10                  15

Ser Leu Arg Leu Ser Cys Ala Ala Ser Gly Phe Asp Phe Ser Arg Tyr
            20                  25                  30

Gly Leu His Trp Val Arg Gln Ala Pro Gly Lys Gly Leu Glu Trp Val
        35                  40                  45

Ala Val Ile Val Tyr Ala Gly Ser Asn Lys Tyr Tyr Ala Asp Ser Val
    50                  55                  60

Lys Gly Arg Phe Thr Ile Ser Lys Asp Asn Ser Lys Asn Thr Met His
65                  70                  75                  80

Leu Gln Met Ser Asp Leu Arg Thr Glu Asp Thr Ala Val Tyr Tyr Cys
                85                  90                  95

Ala Arg Asp Gln Ala Phe Asp Leu Trp Gly Gln Gly Thr Met Val Thr
                100                 105                 110

Val Ser Ser
        115

<210> SEQ ID NO 50
<211> LENGTH: 107
<212> TYPE: PRT
<213> ORGANISM: Homo sapiens

<400> SEQUENCE: 50

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Gly Ile Ser Arg Ser
            20                  25                  30

Val Asn Trp Tyr Gln Gln Lys Pro Gly Lys Ala Pro Lys Leu Leu Ile
        35                  40                  45
```

```
Phe Asp Ala Ser His Leu Glu Arg Gly Val Pro Ser Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Arg Ile
                85                  90                  95

Ser Phe Gly Gln Gly Thr Arg Leu Glu Ile Lys
            100                 105
```

```
<210> SEQ ID NO 51
<211> LENGTH: 345
<212> TYPE: DNA
<213> ORGANISM: Homo sapiens

<400> SEQUENCE: 51
caggggaagt tggtggagtc tgggggaggc gtgatccaac ctggggaggtc cctaagactc        60 tcttgtgcag cctctggatt cgacttcagt cgttatggtc tccactgggt ccgccaggct       120
ccaggcaagg ggctggagtg ggtggcagtt attgtatacg ctggaagtaa taaatattat       180
gcagactccg tgaagggccg attcaccatc tccaaagata attctaagaa cacgatgcat       240
ctgcaaatga gcgacctgag aactgaggac acggctgttt attactgtgc gagagaccag       300
gcttttgatc tctggggcca agggacaatg gtcaccgtgt cctca                       345
```

```
<210> SEQ ID NO 52
<211> LENGTH: 322
<212> TYPE: DNA
<213> ORGANISM: Homo sapiens

<400> SEQUENCE: 52
gacatccaga tgacccagtc tcctgcctcc ctgtctgcat ctgtaggaga cagagtcacc        60
atcacttgcc aggcgagtca gggcattagc aggtctgtaa attggtacca gcagaagcca       120
gggaaagccc ctaaactcct gatcttcgat gcatcccatt tggaaagagg ggtcccatca       180
aggttcagtg gcagtggata tgggacagat tttactttca ccatcagcag cctgcagcct       240
gaagatattg caacatatta ctgtcaacaa tatgataatc tccggatcag cttcggccaa       300
gggacacgac tcgagatcaa aa                                                322
```

```
<210> SEQ ID NO 53
<211> LENGTH: 8
<212> TYPE: PRT
<213> ORGANISM: Homo sapiens

<400> SEQUENCE: 53

Gly Phe Asp Phe Ser Arg Tyr Gly
1               5
```

```
<210> SEQ ID NO 54
<211> LENGTH: 8
<212> TYPE: PRT
<213> ORGANISM: Homo sapiens

<400> SEQUENCE: 54

Ile Val Tyr Ala Gly Ser Asn Lys
1               5
```

```
<210> SEQ ID NO 55
<211> LENGTH: 8
<212> TYPE: PRT
<213> ORGANISM: Homo sapiens
```

<400> SEQUENCE: 55

Ala Arg Asp Gln Ala Phe Asp Leu
1               5

<210> SEQ ID NO 56
<211> LENGTH: 6
<212> TYPE: PRT
<213> ORGANISM: Homo sapiens

<400> SEQUENCE: 56

Gln Gly Ile Ser Arg Ser
1               5

<210> SEQ ID NO 57
<211> LENGTH: 3
<212> TYPE: PRT
<213> ORGANISM: Homo sapiens

<400> SEQUENCE: 57

Asp Ala Ser
1

<210> SEQ ID NO 58
<211> LENGTH: 9
<212> TYPE: PRT
<213> ORGANISM: Homo sapiens

<400> SEQUENCE: 58

Gln Gln Tyr Asp Asn Leu Arg Ile Ser
1               5

<210> SEQ ID NO 59
<211> LENGTH: 128
<212> TYPE: PRT
<213> ORGANISM: Homo sapiens

<400> SEQUENCE: 59

Glu Val Gln Leu Val Glu Ser Gly Gly Gly Val Val Gln Pro Gly Thr
1               5                   10                  15

Ser Leu Arg Leu Thr Cys Val Ala Ser Gly Phe Thr Phe Gly Thr Tyr
                20                  25                  30

Gly Met Tyr Trp Leu Arg Gln Ser Pro Gly Lys Gly Leu Glu Trp Val
            35                  40                  45

Ala Phe Ile Trp Leu Asp Gly Ser Lys Thr Tyr Tyr Ala Asp Ser Val
        50                  55                  60

Lys Gly Arg Phe Thr Val Ser Arg Asp Asn Ser Lys Asn Lys Leu Tyr
65                  70                  75                  80

Leu Glu Met Asn Ser Leu Ser Ala Glu Asp Thr Ala Met Tyr Tyr Cys
                85                  90                  95

Ala Arg Ala Pro Gly Ser Val Trp Tyr Asp Thr Arg Gly His Met Lys
            100                 105                 110

Gly Trp Phe Asp Pro Trp Gly Gln Gly Thr Leu Val Thr Val Ala Ser
            115                 120                 125

<210> SEQ ID NO 60
<211> LENGTH: 110
<212> TYPE: PRT
<213> ORGANISM: Homo sapiens

<400> SEQUENCE: 60

-continued

```
Gln Ser Val Leu Thr Gln Thr Pro Ser Val Ser Gly Thr Pro Gly Gln
1               5                   10                  15

Arg Val Thr Ile Ser Cys Ser Gly Ser Ser Ser Asn Ile Glu Asn Asn
            20                  25                  30

Tyr Leu Tyr Trp Tyr Gln Gln Leu Pro Gly Thr Ala Pro Lys Leu Leu
        35                  40                  45

Ile Tyr Gly Asp Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Asn Leu
            85                  90                  95

Ser Gly Pro Val Phe Gly Gly Gly Thr Lys Val Thr Val Leu
            100                 105                 110
```

<210> SEQ ID NO 61
<211> LENGTH: 385
<212> TYPE: DNA
<213> ORGANISM: Homo sapiens

<400> SEQUENCE: 61

```
gaagtgcagc tggtggagtc tgggggaggc gtggtccagc ctgggacgtc cctgagactc        60
acctgtgtag cgtctggatt cacattcggt acttatggca tgtactggct ccgccagtct       120
ccaggcaagg ggctggagtg ggtggccttt atatggcttg atggaagtaa gacttactat       180
gcagactccg tgaagggccg attcaccgtc tccagagaca attccaagaa taagttgtat       240
ctggaaatga acagcctgag cgccgaggac acggcgatgt actactgtgc gagagcccca       300
ggctcggttt ggtatgacac tcgtggccat atgaaagggt ggttcgaccc ctggggccag       360
ggaaccctgg tcaccgtcgc ctcag                                             385
```

<210> SEQ ID NO 62
<211> LENGTH: 331
<212> TYPE: DNA
<213> ORGANISM: Homo sapiens

<400> SEQUENCE: 62

```
cagtctgtgc tgactcagac accctcagtg tctgggaccc ccgggcagag ggtcaccatc        60
tcttgttctg gaagcagctc caacatcgaa aataattatt tatactggta ccagcagctc       120
ccaggaacgg cccccaaact cctcatctat ggtgataatc ggcggccctc aggggtccct       180
gaccgattct ccggctccaa gtctggcacc tcagcctccc tggccatcag tgggctccgg       240
tccgaagatg aggctgatta ttactgtgca acatgggatg acaacctgag tggtccggtg       300
ttcggcggag ggaccaaggt gaccgtccta g                                      331
```

<210> SEQ ID NO 63
<211> LENGTH: 8
<212> TYPE: PRT
<213> ORGANISM: Homo sapiens

<400> SEQUENCE: 63

```
Gly Phe Thr Phe Gly Thr Tyr Gly
1               5
```

<210> SEQ ID NO 64
<211> LENGTH: 8
<212> TYPE: PRT
<213> ORGANISM: Homo sapiens

<400> SEQUENCE: 64

Ile Trp Leu Asp Gly Ser Lys Thr
1               5

<210> SEQ ID NO 65
<211> LENGTH: 21
<212> TYPE: PRT
<213> ORGANISM: Homo sapiens

<400> SEQUENCE: 65

Ala Arg Ala Pro Gly Ser Val Trp Tyr Asp Thr Arg Gly His Met Lys
1               5                   10                  15

Gly Trp Phe Asp Pro
            20

<210> SEQ ID NO 66
<211> LENGTH: 8
<212> TYPE: PRT
<213> ORGANISM: Homo sapiens

<400> SEQUENCE: 66

Ser Ser Asn Ile Glu Asn Asn Tyr
1               5

<210> SEQ ID NO 67
<211> LENGTH: 3
<212> TYPE: PRT
<213> ORGANISM: Homo sapiens

<400> SEQUENCE: 67

Gly Asp Asn
1

<210> SEQ ID NO 68
<211> LENGTH: 11
<212> TYPE: PRT
<213> ORGANISM: Homo sapiens

<400> SEQUENCE: 68

Ala Thr Trp Asp Asp Asn Leu Ser Gly Pro Val
1               5                   10

<210> SEQ ID NO 69
<211> LENGTH: 6
<212> TYPE: PRT
<213> ORGANISM: Artificial Sequence
<220> FEATURE:
<223> OTHER INFORMATION: cleavage site

<400> SEQUENCE: 69

Lys Lys Arg Lys Arg Arg
1               5

<210> SEQ ID NO 70
<211> LENGTH: 4
<212> TYPE: PRT
<213> ORGANISM: Artificial Sequence
<220> FEATURE:
<223> OTHER INFORMATION: Cleavage site

<400> SEQUENCE: 70

Arg Gln Ser Arg
1

-continued

```
<210> SEQ ID NO 71
<211> LENGTH: 6
<212> TYPE: PRT
<213> ORGANISM: Artificial Sequence
<220> FEATURE:
<223> OTHER INFORMATION: Cleavage site

<400> SEQUENCE: 71

Arg Arg Arg Arg Arg Arg
1               5

<210> SEQ ID NO 72
<211> LENGTH: 22
<212> TYPE: PRT
<213> ORGANISM: Homo sapiens

<400> SEQUENCE: 72

Leu Ile Lys Thr Glu Leu Asp Leu Thr Lys Ser Ala Leu Arg Glu Leu
1               5                   10                  15

Lys Thr Val Ser Ala Asp
            20
```